(12) United States Patent
Higgins et al.

(10) Patent No.: US 12,349,859 B2
(45) Date of Patent: Jul. 8, 2025

(54) TWO-PHASE INSTRUMENT GUIDANCE FOR ACCURATE ENDOSCOPIC SURGICAL PROCEDURES

(71) Applicant: The Penn State Research Foundation, University Park, PA (US)

(72) Inventors: William E. Higgins, State College, PA (US); Wennan Zhao, Emerald Hills, CA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 18/836,573

(22) PCT Filed: Jan. 25, 2023

(86) PCT No.: PCT/US2023/011526
§ 371 (c)(1),
(2) Date: Aug. 7, 2024

(87) PCT Pub. No.: WO2023/146902
PCT Pub. Date: Aug. 3, 2023

(65) Prior Publication Data
US 2025/0134347 A1    May 1, 2025

Related U.S. Application Data

(60) Provisional application No. 63/358,937, filed on Jul. 7, 2022, provisional application No. 63/303,712, filed on Jan. 27, 2022.

(51) Int. Cl.
*A61B 1/00* (2006.01)
*A61B 1/267* (2006.01)
(Continued)

(52) U.S. Cl.
CPC ...... *A61B 1/000095* (2022.02); *A61B 1/2676* (2013.01); *A61B 90/361* (2016.02);
(Continued)

(58) Field of Classification Search
CPC ............ G06T 7/00; G06T 2207/10068; A61B 90/361; A61B 1/2676; A61B 2034/107; A61B 2034/2055
See application file for complete search history.

(56) References Cited

U.S. PATENT DOCUMENTS

2008/0207997 A1    8/2008  Higgins et al.
2010/0185156 A1    7/2010  Kanner et al.
(Continued)

Primary Examiner — Michael T Rozanski
(74) Attorney, Agent, or Firm — DINSMORE & SHOHL LLP

(57) ABSTRACT

A two-stage method for guiding an endoscope and second device toward a target destination near the ROI includes navigation and localization. The endoscope is navigated near the vicinity of the ROI according to a pre-procedure plan. When the ROI location is reached, the second device's tip is pushed far enough through the endoscope so that its tip is outside the endoscope and in the endoscope's video view. Then a two-phase registration mechanism is used: i. Phase 1: Align the endoscope by registering the endoscope's video to a virtual bronchoscope's simulated video stream; ii. Phase 2: Align the second device by registering the second device's shape in the endoscope's video to a virtual second device model.

10 Claims, 34 Drawing Sheets

(51) Int. Cl.
*A61B 34/10* (2016.01)
*A61B 34/20* (2016.01)
*A61B 90/00* (2016.01)
*G06T 7/00* (2017.01)

(52) U.S. Cl.
CPC .......... *G06T 7/00* (2013.01); *A61B 2034/107* (2016.02); *A61B 2034/2055* (2016.02); *G06T 2207/10068* (2013.01)

(56) References Cited

U.S. PATENT DOCUMENTS

| | | |
|---|---|---|
| 2011/0275891 A1 | 11/2011 | Shemi |
| 2015/0257847 A1 | 9/2015 | Higgins et al. |
| 2021/0386491 A1 | 12/2021 | Shmayahu et al. |

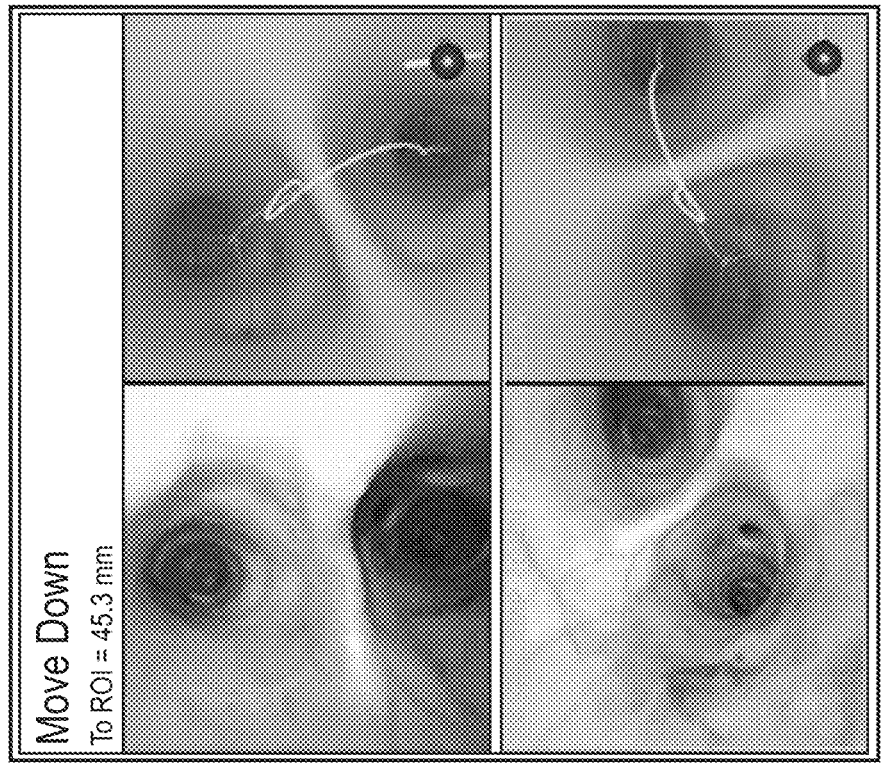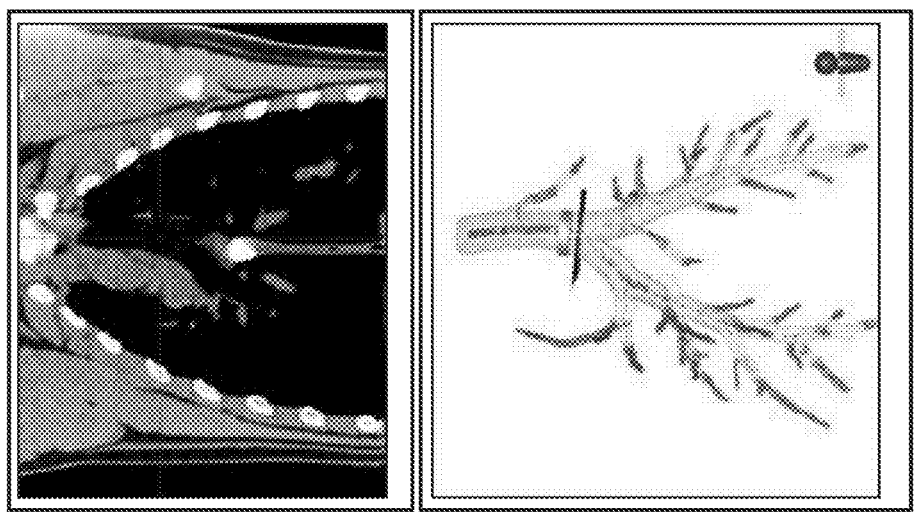
FIG. 3

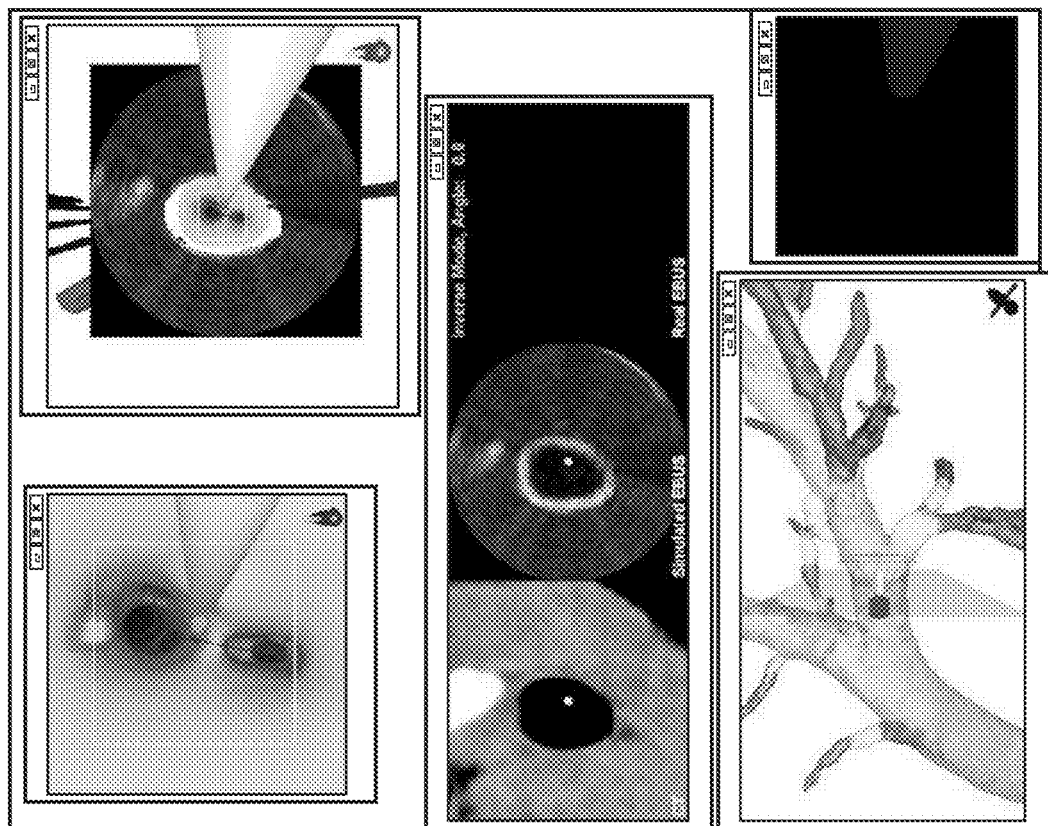
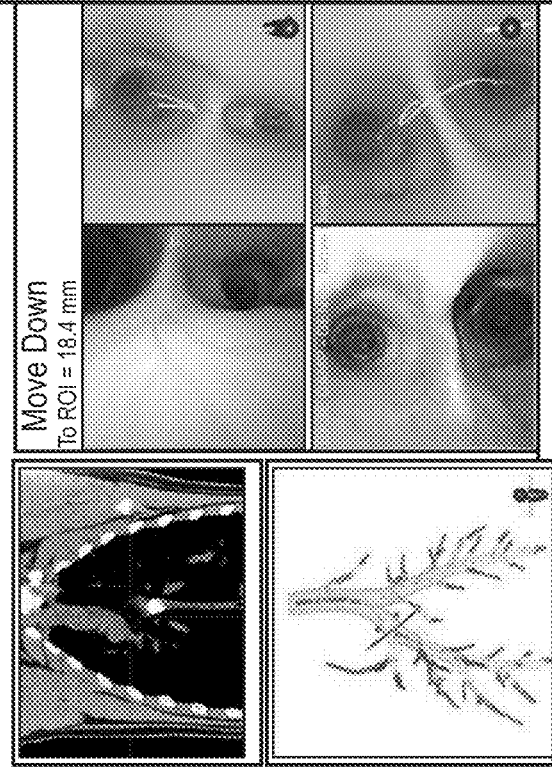
FIG. 4

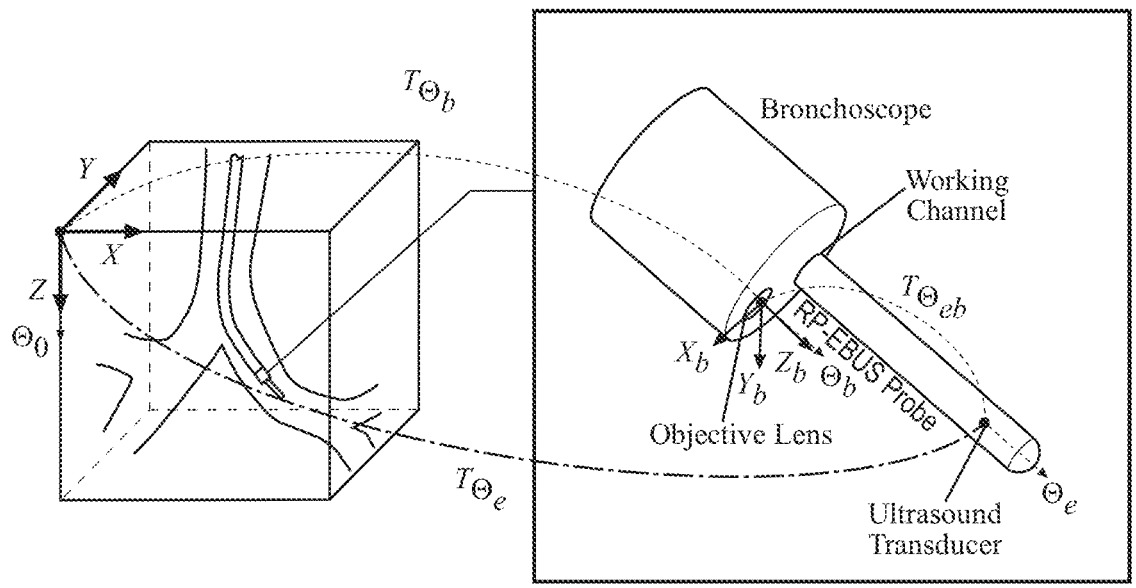
FIG. 10
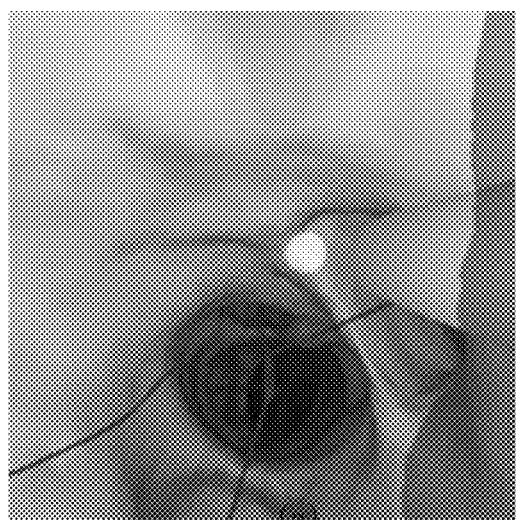 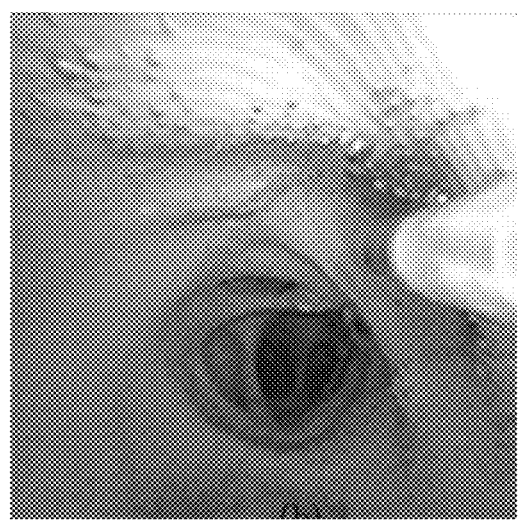
FIG. 11A       FIG. 11B

3D Airway Tree

Peribronchus Renderer

VB View

Video

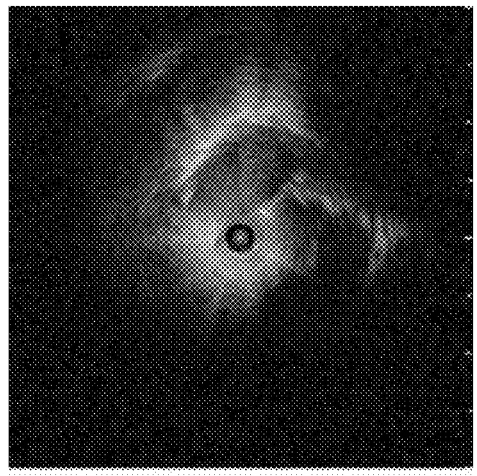
FIG. 35G Real RP-EBUS Frame
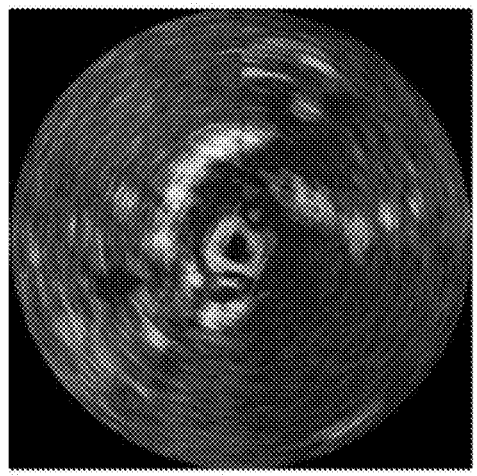
FIG. 35F RP-EBUS Simulation
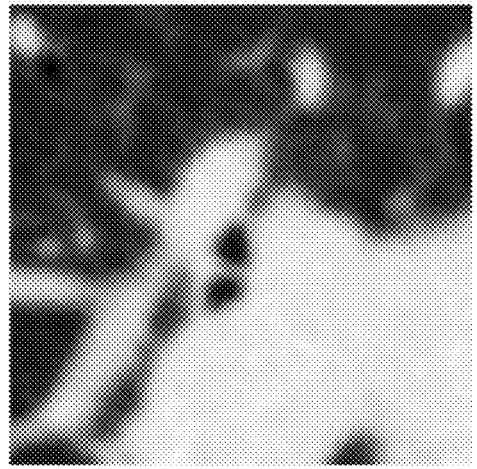
FIG. 35E CT Oblique

TWO-PHASE INSTRUMENT GUIDANCE FOR ACCURATE ENDOSCOPIC SURGICAL PROCEDURES

CROSS-REFERENCE TO RELATED APPLICATION

This application is the U.S. National Stage of PCT/US2023/011526 filed on Jan. 25, 2023, which claims priority from U.S. Provisional Patent Application Ser. No. 63/303,712, filed on Jan. 27, 2022, and U.S. Provisional Patent Application Ser. No. 63/358,937, filed Jul. 7, 2022 the entire content of both are incorporated herein by reference in their entirety.

GOVERNMENT SPONSORSHIP

This invention was made with government support under Grant No. CA151433 awarded by the National Institutes of Health. The Government has certain rights in the invention.

FIELD OF THE INVENTION

This invention relates generally to surgical procedure guidance and, in particular, to the coordinated usage and registration of multiple surgical devices used at the same time, as applicable to endoscopy.

BACKGROUND OF THE INVENTION

Many surgical protocols require the joint use of two complementary devices to perform a given task. Examples of such protocols are discussed in the literature [49, 51, 63, 64] and include:
1. Using bronchoscopy in tandem with an endobronchial ultrasound (EBUS) probe to localize extraluminal peripheral lung sites for the purposes of lung cancer diagnosis, tissue biopsy, or treatment delivery.
2. Using bronchoscopy in tandem with an optical coherence tomography (OCT) probe to localize and identify suspect early cancer lesions of the airway wall.
3. Using an endoscope in tandem with a second device inserted into the endoscope's working channel to perform a local ultrasound examination and/or deliver treatment to a clinical site of interest.

Physicians currently perform such multi-device tasks poorly in general. Two limitations give rise to this situation. First, the physician's skill and dexterity in coordinating the use of the two devices varies greatly. In particular, the physician essentially has to guess where to position the second device, resulting in a blind and frequently unsuccessful procedure. Related to this point is the second issue: while guidance systems exist for navigating an endoscope, no effective tools exist to help the physician coordinate and maneuver two devices. Even robotics-based guidance systems currently have no facility for coordinating the use of two endoscopic devices deployed in tandem. As a result, for lung cancer as an example, the accuracy of diagnosing peripheral nodules is low and varies widely across physicians, while the assessment of suspect early lung cancer lesions developing within the airway mucosa is essentially never done.

Focusing on a particular field, lung cancer remains the largest cause of cancer death in the United States [54]. To achieve effective outcomes for patients suspected of having lung cancer, accurate disease diagnosis and management are essential [49]. To perform these operations, the physician begins by identifying suspicious cancerous lesions on a patient's chest computed tomography (CT) imaging scan. The physician then confirms disease diagnosis via bronchoscopic needle biopsy. To do this for a particular lesion, the physician first navigates the bronchoscope through the airways and then finely localizes the device near the lesion site to collect the requisite tissue biopsies. A bronchoscope, however, only images the airway's endoluminal interior, while most lesions arise outside the airways.

To address this shortcoming, the physician uses a second complementary device, endobronchial ultrasound (EBUS), in concert with the bronchoscope to visualize and localize extraluminal lesions [63, 64]. Thus, to visualize a peripheral lesion, the physician first navigates the bronchoscope to the correct airway nearest the lesion. Next, the physician inserts the EBUS probe into the bronchoscope's working channel and then scans the presumed extraluminal region that contains the lesion. This scanning process gives two-dimensional (2D) 360° cross-sectional images of the scanned anatomy perpendicular to the probe's longitudinal axis, shown in FIG. 1.

Unfortunately, the use of EBUS essentially involves a blind guess-and-check process. To this point, EBUS has a steep learning curve, and the physician skill differences in using EBUS to localize lesions are well documented [19, 46]. As a result, biopsy success rates vary considerably, as confirmed by recent multi-center clinical studies [46]. Several factors influence the physician's ability to use EBUS [19, 20]. First, the physician must mentally translate their anatomical knowledge to imaging observations and live EBUS views. Second, EBUS images do not lie on the orthogonal 2D axial, coronal, or sagittal planes readily observed in an imaging scan. This makes it difficult to manually correlate CT observations to live EBUS views. Third, because of EBUS's limited field of view, the physician may need to sweep the EBUS probe over a broad—and unclear—swath of the airway walls to find suitable extraluminal lesion views. Finally, EBUS images suffer from inherent degradations that lower image quality.

Virtual reality training systems now exist for EBUS training [42, 52]. But these systems are hard-wired for fixed 2D virtual chest-anatomy models having predefined acoustic tissue properties and offer no help during live patient-specific situations. Also, no system considers radial probe EBUS (RP-EBUS), which is used for peripheral airway sites.

On another front, new image-guided bronchoscopy systems have received broad acceptance as effective tools for assisting with bronchoscopy procedure planning and live guidance [11, 18, 48]. Such systems have proven to boost physician performance for bronchoscopic airway navigation [3, 24, 53]. No system, however, offers assistance on how to preplan and later guide a peripheral lesion biopsy procedure entailing the use of both a bronchoscope and an EBUS probe. In particular, no means exists for off-line planning and live guidance of: 1) when to switch devices from bronchoscopy to EBUS; and 2) where precisely to scan using the EBUS probe. Thus, even after using navigation assistance for the bronchoscope, the physician still must perform EBUS using the same guess-and-check approach as ever.

In addition, recent developments of second devices for supplementing bronchoscopy now enable many new methods for treating and examining a suspect peripheral lung lesion or tumor [18]. These include radiofrequency ablation, microwave ablation, photodynamic therapy, brachytherapy, cryoablation, vapor thermal ablation, and direct therapeutic injection using a needle.

Note that in the recent past, most diagnosed lung cancers were advanced stage 3-4 disease, found by serendipitous discovery in patients with obvious symptoms (e.g., huge tumor on CT). Note that disease stage dramatically affects survival. In particular, the 5-year survival rate for stage 0 is >90%, 70% for stage 1A, and <5% for stage 4. Fortunately, the ongoing world-wide roll-out of CT-based lung cancer screening promises a major shift toward early detection of smaller (<10 mm) tumors, resulting in a patient population shifting toward highly-treatable stage-1 disease [58].

Unfortunately, even when physicians use existing image-guided bronchoscopic navigation systems and EBUS for lung cancer diagnosis, a major multi-center study found only a 47% yield for suspect peripheral tumors [46]. Hence, investigators have stressed that this high number of inconclusive bronchoscopies is unacceptable for accurate tumor diagnosis [23]. This poor performance becomes even more problematic in light of the increasing need to biopsy prospective stage-1 patients exhibiting smaller tumors [26].

To emphasize this point, for the management of patients at high risk for lung cancer, early stage lung cancer has a median survival time of only 14 months when left untreated—i.e., such cancers rapidly advance to a higher stage. Thus, follow-up disease surveillance for such patients using repeat CT scans and bronchoscopies is critical. This is compounded by a >30% detection rate for cancer recurrence and secondary cancer during surveillance [56, 61]. Unfortunately, surveillance burdens patients with considerable stress, high costs, extra radiation from repeat CT scans, and, at times, risky surgery—even though 96% of the 1.5 million suspect peripheral cancer lesions detected yearly in the US ultimately prove to be benign [33, 55]. Because CT screening is greatly increasing the population requiring surveillance, more reliable methods are desperately needed to better manage the large number of indeterminate lesions (nodules)—e.g., methods that reduce the number of inconclusive bronchoscopies [65].

On a different note, physicians strongly recognize the value of favoring minimally invasive endoscopic procedures over more invasive surgery, in terms of patient cost, reduction of complications and morbidity, and enabling examinations that an endoscope alone can't accomplish. An endoscope helps the physician look inside a hollow anatomical organ system, such as the lung airways or colon, without invasion. But most important diagnostic ROIs are situated outside a hollow organ system's lumen. Unfortunately, it is well-known that physicians are not able to localize extraluminal ROIs well using bronchoscopy. For example, the study of Merritt et al. showed that, while a physician could reach the correct airway for localizing an ROI in 78% of trials, they could only accurately localize the ROI in 43% of trials [40].

This had led to the development of many highly promising secondary devices, inserted into the endoscope's working channel, that enable visualization of structures outside the lumen—thereby, providing a vital means for diagnosis, treatment, or monitoring of extraluminal ROIs. In addition to EBUS (which is used in many domains besides the lungs), examples of these devices are OCT, Raman spectroscopy, and photo-acoustic probes [4, 5, 38]. Unfortunately, the same difficulty in when and where to use the second device precisely—and the lack of tools to help guide the device's use—arises, similar to EBUS. Finally, new local therapeutic devices, such as endoscopic cryotherapy and others, exist, but remain difficult to administer effectively, limiting their wider usage.

In summary, many surgical procedures that require traversing complex hollow tubular anatomical regions, such as the lung airways, often entail using an endoscope in tandem with a second supplemental device Yet, such procedures are generally very difficult or fraught with poor performance. Unfortunately, no effective tools exist for helping the physician perform such procedures successfully. In particular, no tools give the following assistance: 1) when to invoke the second device; and 2) where the second device should be used.

SUMMARY OF THE INVENTION

The embodiments of the present invention provide a methodology for guiding surgical procedures that take place in a hollow organ system and require an endoscope and a second complementary device used in tandem, where the second device is deployed through the endoscope's working channel.

The present methodology offers an integrated unique approach for managing the deployment of two distinct devices through the hollow organ system and the synchronization of these two devices to a target destination at or near a region of interest (ROI) that must be examined by the second device, as the endoscope (i.e., the first device) does not have the proper capabilities for "seeing" the target destination and for performing the desired surgical task.

The hollow organ system may be lung airways, vasculature in a heart, brain, liver, kidney or hollow areas in a colon, stomach, bladder, pelvis/abdomen.

The endoscope may be a bronchoscope, colonoscope, laparoscope, angioscope or cystoscope.

The ROI may be a suspect tumor or cancer nodule. The target destination may be an optimal biopsy site, a site for anatomical, cytological, or histopathological examination, or a therapeutic site.

Examination of the ROI may involve performing a visual assessment of the ROI, delivering treatment to the ROI, or collecting anatomical tissue from the ROI by the endoscope operator.

The second device may be an EBUS probe, optical coherence tomography probe, confocal laser endomicroscope, radiofrequency ablation device, microwave ablation device, photodynamic therapy device, brachytherapy device, cryoablation device, vapor thermal ablation device, or a needle for direct therapeutic intervention such as extracting a tissue sample or injection.

To help guide the procedure, we draw on virtual anatomical views and graphical cues derived from a patient's imaging scan. An example of such a procedure is the examination of a peripheral lung lesion using a bronchoscope and an EBUS probe, where a patient's chest CT scan is used to derive the necessary virtual data and cues.

Using the patient's imaging scan, a planning and guidance protocol can be derived. First, a pre-operative procedure plan is computed. The procedure plan contains information pertinent for maneuvering both devices.

A precomputed procedure plan may include a virtual model of the hollow organ system's surfaces to define the virtual endoscope, a guidance route leading to the ROI and guidance cues indicating the distance of various 3D locations from the ROI for optimal examination via the second device. An optimal examination implies that the designated task is performed at its maximal effectiveness; e.g., maximal view of the extraluminal ROI, maximal delivery of therapy to the designated ROI, maximal biopsy tissue sample extraction from an ROI. For guiding the endoscope, the plan contains a route terminating at a target destination near a region of interest (ROI). For navigating the endoscope and deploying the second device, the plan contains guidance cues. The guidance cues may include graphical visualization views, suggested device instructions including how to maneuver each device, when to switch modes from the endoscope to the second device, the position of the endoscope with respect to the ROI, when a preplanned pose near the ROI is reached so that the second device can be invoked to examine the ROI, etc. An optimal examination of the ROI can be performed at the preplanned pose.

When a live procedure is performed, the procedure takes place in two stages: 1. Navigate the endoscope through a complex, hollow tubular organ system until it is near the diagnostic ROI; 2. Localize the endoscope and second device together about the ROI.

In particular, to navigate the endoscope towards the ROI, simulated virtual video views of the hollow organ system from a virtual endoscope defined within a 3D virtual space constructed based on the 3D pre-operative imaging scan are provided along the guidance route, which enable an endoscope operator to maneuver the endoscope toward the target destination.

When the ROI is reached at the end of navigation, localization now begins. For localization, we need a new set of possible maneuvers for moving the endoscope. The goal of these maneuvers is to help the physician position the endoscope within the hollow organ so that the second device can be invoked effectively.

Localization of the endoscope and second device at a preplanned pose about the ROI takes place in a few steps:
 i. providing guidance cues for maneuvering the endoscope in preparation for invoking the second device;
 ii. aligning the endoscope by registering the video view from the endoscope to the virtual video view from the virtual endoscope in the 3D virtual space;
 iii. providing an alert for insertion of the second device into the working channel until a tip of the second device appears in the endoscope's video view; and
 iv. registering the second device's shape in the endoscope's video view to a virtual second device model visible in the virtual view of the virtual endoscope.

Steps (ii.) and (iii.) can occur in either order.

The endoscope and second device are now in position for optimal examination of the ROI with the second device.

It is through the information provided by the guidance strategy that facilitate proper deployment and usage of the two devices, thereby enabling accurate examination, diagnosis, biopsy, and/or treatment of a diagnostic ROI.

The planning and guidance methodologies are implemented as a coordinated suite of computer-based subsystems. One subsystem facilitates pre-operative procedure planning. The second subsystem interfaces to the surgical hardware (e.g., the EBUS/bronchoscopy hardware) to provide live real-time guidance in the surgical suite.

In one embodiment, a complete planning and guidance software system for multimodal image-guidance of bronchoscopy and RP-EBUS is developed. The system is especially tailored to coordinating the use of two endoscopic devices for examining peripheral sites in the lungs. The system synchronizes RP-EBUS data with other imaging modalities and enables more accurate peripheral pulmonary nodule diagnosis. In particular, a real-time CT-based EBUS simulation method is developed and tailored to image-guided bronchoscopy that can produce simulated EBUS views for any orientation within the airways. A 2-phase RP-EBUS registration method is also developed to synchronize the RP-EBUS probe with CT and bronchoscopy during image-guided bronchoscopy. At the system level, RP-EBUS-related cues are integrated into the image-guided bronchoscopy system and a CT-based procedure planning method is developed that enables optimal RP-EBUS invocation, localization, preview, and RP-EBUS video simulation.

Based on the 2-phase RP-EBUS registration method, an intra-operative guidance system is derived consisting of many graphical tools tailored to RP-EBUS invocation and peripheral pulmonary lesion diagnosis. The software runs on a Windows-based PC equipped with a Matrox video frame grabber. The software and methodology could also be adapted to many other clinical applications that require the examination, biopsy, diagnosis, monitoring, and treatment of extraluminal sites outside a hollow organ system.

BRIEF DESCRIPTION OF THE DRAWINGS

FIG. 3 shows an example of a completed maneuver during the navigation stage; (The lower right Base Camp illustrates a frozen live bronchoscopy video frame and guidance VB view after completing a "Rotate CCW" maneuver. The upper left box indicates the next maneuver for the physician to complete ("Move Down"), with the physician having just completed the maneuver before saving as the next Base Camp; the guidance system is also 45.3 mm from the ROI as shown. The blue line in all views denotes the preplanned guidance path to an ROI. Other indications of the current guidance position are given by the 2D coronal CT section view (top left) with red cross hairs and by the 3D airway tree viewer by the yellow cylinder (denoting the bronchoscope tip);

FIG. 4 shows an example guidance display during localization for the same case as FIG. 3; (The left side views are as in FIG. 3, but the system is now only 18.4 mm from the ROI. The right side of the display shows many new views to assist with imminent RP-EBUS invocation: 1) Top left—Peripheral Panorama Renderer; 2) Top right—Peribronchus Renderer—Forward; 3) middle—Peripheral EBUS Match [left view: 2D CT section at the virtual RP-EBUS probe's location; middle view: simulated RP-EBUS view at the same pose; right view: Real EBUS view]; 4) Bottom left—Peripheral Local Renderer; 5) Bottom right—Probe Tracking Viewer);

FIG. 10 shows bronchoscope and RP-EBUS probe geometry in 3D CT chest space; (Red: 2 consecutive rigid transforms from $\Theta_0$, at origin to bronchoscope camera pose $\Theta_b$, and then to RP-EBUS probe pose $\Theta_e$. Blue: the final global rigid transform from $\Theta_0$, at origin to RP-EBUS probe pose $\Theta_e$);

FIG. 11A shows Phase 1—Bronchoscope and CT registration (case 20349.3.48) (the CT-based VB view with integrated virtual RP-EBUS probe);

FIG. 11B shows Phase 1—Bronchoscope and CT registration (case 20349.3.48) (the real bronchoscopic video view with visible real RP-EBUS probe);

FIG. 21A shows a 3D surface under the default mode);

(FIG. 27A shows the tool during RP-EBUS probe segmentation. The gray silhouette represents the real RP-EBUS segmentation mask. The blue silhouette represents the virtual RP-EBUS probe at the current position);

(FIG. 28A shows starting from one side of the probe, mouse left click within 10 pixels from the boundary will automatically adhere the clicked point to the closest point on the border);

(FIG. 29A shows the plot properties dialog controls the type of data plotted for which path and a specified offset and length of viewing sites. The user can point to plot points (a point corresponds to a viewing site) to see visual views of the point in other tools. The plot can be output as an image file. Note that since the Reach Capacity checkbox is checked, the Peripheral 2D Plot Tool will use the diameter value in Device Diam box to calculate Cornish's reach capacity);

FIGS. 35A-35G show the Image-guided RP-EBUS bronchoscopy system example (case 21405-169); (All views synchronized to a peripheral lesion site in the left upper lobe. FIG. 35A: global 3D airway tree rendering showing preplanned blue guidance route; FIG. 35B: more focused parabronchus renderer; black arrows point to a virtual bronchoscope tip, orange object represents the lesion in CT, and the square planes perpendicular to the virtual tip denote the RP-EBUS probe's scan plane. FIG. 35C: registered pair of CT-based VB view; FIG. 35D: live videobronchoscopic view; virtual and real RP-EBUS probes appear in these views. FIGS. 35E-35F: CT oblique section and simulated RP-EBUS view; Figure G: real RP-EBUS frame #5163).

DETAILED DESCRIPTION OF THE INVENTION

According to embodiments of the present invention, a complete planning and guidance system and a method are provided for guiding surgical procedures that take place in a hollow organ system and require an endoscope and a second complementary device used in tandem, where the second device is deployed through the endoscope's working channel. The endoscope is guided to navigate through the hollow organ system to reach a region of interest (ROI). A target destination at or near the region of interest (ROI) must be examined by the second device, as the endoscope (i.e., the first device) does not have the proper capabilities for "seeing" the target destination and for performing the desired surgical task.

The present invention offers an integrated unique approach for managing the deployment of two distinct devices through the hollow organ system and the synchronization of these two devices before examining the target destination.

Before the procedure in the operating room, a procedure plan is developed by processing the patient's imaging plan (e.g., CT scan) to examine a surgical site, where the surgical site is outside (extraluminal to) the hollow organ system (e.g., airways).

During the live surgical procedure in the operating room, the guidance strategy and the procedure plan are used to guide the physician's use of the two surgical devices.

The surgical procedure requires two devices. The main device is an endoscope (e.g., bronchoscope), which is a long, thin, tubular device, that the physician navigates through the hollow organ system (e.g., airways) close to desired surgical site that is outside the organ system. Since the endoscope cannot see outside the organ system, it cannot help localize the desired surgical site. A second thin device might be a probe (EBUS or some similar device) and is then inserted into the endoscope's working channel. This second device is able to see—i.e., localize—surgical sites situated outside the organ system.

Figure 1A:
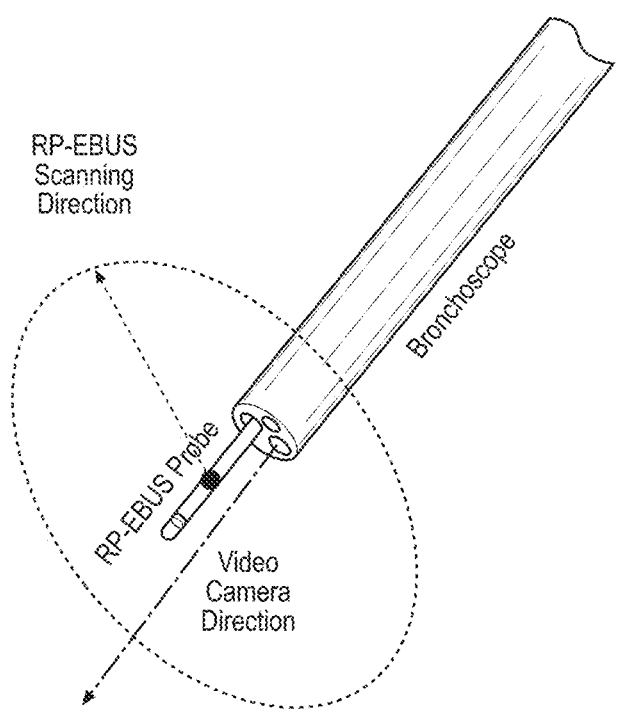
FIG. 1A shows an Olympus UM-S20-17S radial-probe endobronchial ultrasound (RP-EBUS) extended from the bronchoscope's working channel; (the orientation and form of the EBUS scan plane is shown relative to the bronchoscope's tip)
Figure 1B:
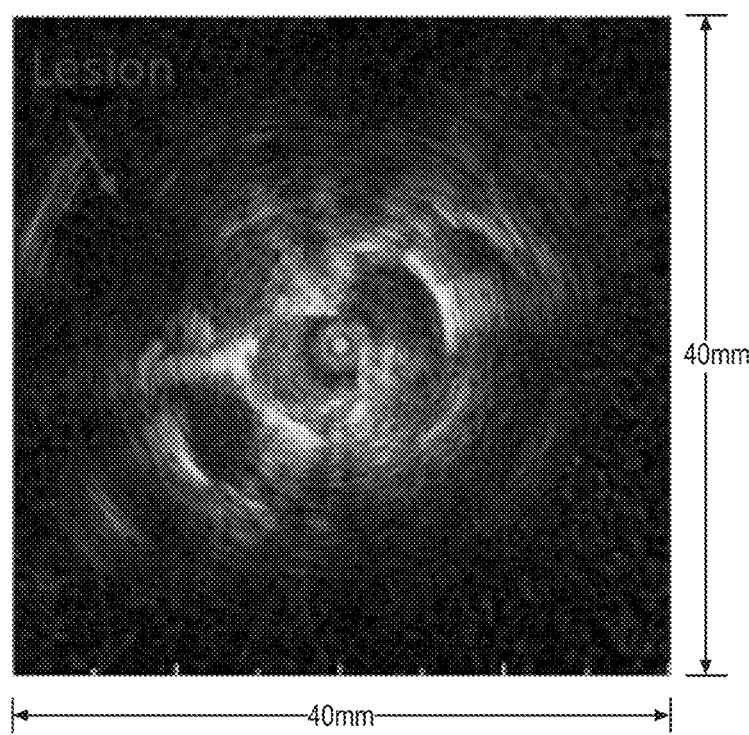
FIG. 1B shows an example RP-EBUS image and real dimensions; (a lesion appears as a darker mass)

For an example of the lung cancer problem, a goal is to examine peripheral ROIs (suspect cancer lesions) using bronchoscopy and radial probe EBUS, shown in FIG. 1. It is easy to accurately navigate the bronchoscope into the correct airway branch closest to the surgical site. Once the physician gets the bronchoscope into the final branch, they have a hard time using the second device accurately: how far out should the physician push the device? Where precisely should the physician probe with the device? The device also flops around, etc.

The present invention therefore provides a two-stage method for guiding an endoscope and second device toward a target destination near the ROI. The endoscope is navigated near the vicinity of the ROI, using i. A guidance route; ii. Simulated video views of the endoluminal organ system, drawn from a virtual endoscope; iii. Visual cues indicating the endoscope's position with respect to the ROI. Then, a guidance strategy is used during the live procedure that provides graphical visualization views, suggested device instructions, and quantitative measures to help guide how to maneuver each device, when to switch modes from the endoscope to the second device and when an optimal ROI location is reached.

When the ROI location is reached, the endoscope and second device are localized at optimal poses about the ROI. The localization happens by pushing the probe against the wall of the hollow organ system. The second device's tip has to be pushed far enough through the endoscope so that its tip is outside the endoscope and in the endoscope's video view. For the two-device problem, a two-phase registration mechanism is used:
  i. Phase 1: Align the endoscope by registering the endoscope's video to a virtual bronchoscope's simulated video stream;
  ii. Phase 2: Align the second device by registering the second device's shape in the endoscope's video to a virtual second device model.

Figure 2:
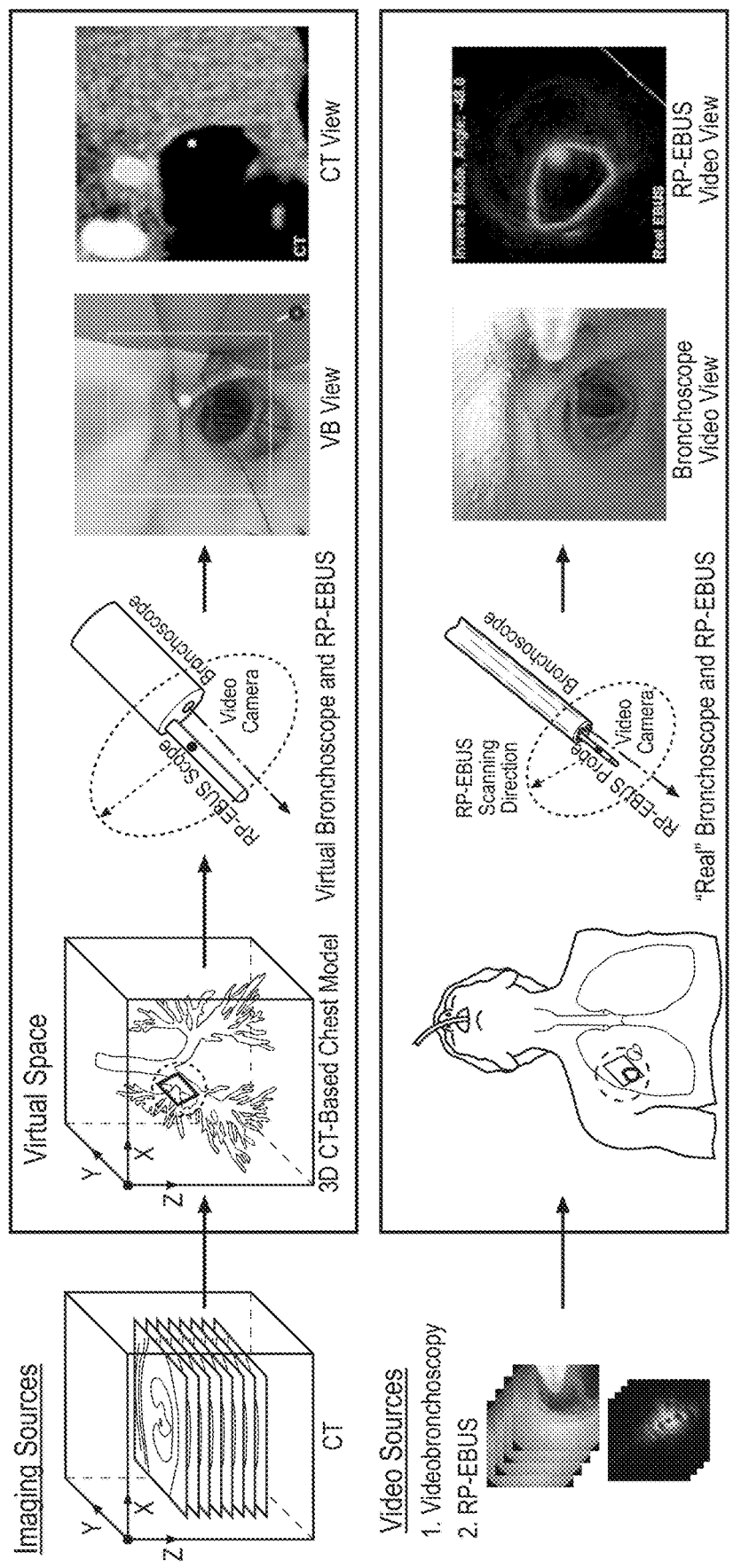
FIG. 2 shows virtual and real spaces applicable to image-guided EBUS bronchoscopy.

Returning to the example of the lung cancer problem, a goal is to examine peripheral ROIs (suspect cancer lesions) using bronchoscopy and radial probe EBUS, shown in FIG. 1. A patient's high-resolution 3D CT chest scan serves as the main radiologic imaging input to our methodology. The methodology considers the patient's physical chest space with two distinct multimodal 3D data spaces, as shown in FIG. 2:
  1. A virtual space, established by the 3D CT chest scan, serves as the reference space and provides anatomical cues for both procedure planning (pre-operative analysis) and later image-guided bronchoscopy (intra-operative device guidance).
  2. A real space, derived from the live bronchoscopic and EBUS video sources in the operating room, supplies live intraluminal and extraluminal airway information for image-guided bronchoscopy.

For bronchoscopy, the aforementioned "virtual endoscope" is referred to as a virtual bronchoscope (VB). To enable interactive live bronchoscopy guidance, a linkage between the two spaces is devised during the live procedure. In particular, the real-space bronchoscope and EBUS probe is aligned to their CT-based virtual-space counterparts.

Using the present methodology requires two main steps: 1) pre-operative procedure planning; followed by 2) live intra-operative image-guided bronchoscopy. Section 1 first summarizes procedure planning. Next, Section 2 discusses the two-stage guidance strategy, while Section 3 focuses on the crucial two-phase bronchoscope/probe registration method. Continuing, Section 4 then describes the software systems that give implementations of the methods, while Section 5 gives validation results for our methods. Finally, Section 6 offers a discussion.

1. Pre-Operative Procedure Planning

Pre-operative procedure planning is performed off-line prior to the live procedure and usually involves four steps:
  1. Compute a 3D chest model from a patient's high-resolution 3D CT chest scan. The model, derived from existing methods, includes the airway tree, airway centerlines and endoluminal surfaces, lungs, vasculature, and thoracic cavity [12, 27, 36, 57].
  2. Identify and define ROIs in the CT scan, using existing automatic and semi-automatic methods [13, 34, 35].
  3. Compute an optimal airway navigation route to each ROI that maximizes potential biopsy yield and avoids major vasculature [24, 67]. The computation draws upon the constructed 3D chest model and ROIs.
  4. Derive bronchoscope and EBUS device maneuvers that instruct how to maneuver each device along the navigation route [62, 69]. It is these maneuvers that dictate when to navigate the bronchoscope and when and where to invoke EBUS to visualize the ROI.

During procedure planning, we added RP-EBUS-related geometry and bronchoscope maneuvers to the optimal route for an ROI.

Step 4 entails methods for deriving specific device maneuvers for maneuvering the bronchoscope and second device during both the navigation and localization phases. For navigation, we use existing methods as discussed in to derive device maneuvers. Using the algorithm discussed in [30], we use a method that uses the optimal airway route combined with the 3D CT-based airway tree model and centerline structure to derive a sequence of maneuvers for navigating the bronchoscope through each airway branch traversed by the optimal route. Possible maneuvers include "Move UP," "Move DOWN", "Rotate Clockwise," and "Rotate Counterclockwise." These maneuvers instruct the physician how to move the bronchoscope during navigation.

When the final planned airway branch is reached (signaling the end of navigation), localization now begins. For localization, we need a new set of possible maneuvers for moving the bronchoscope. The goal of these maneuvers is to help the physician position the bronchoscope within the final airway branch so that the EBUS probe (second device) can be invoked effectively. The necessary maneuvers always require the following sequence: 1) "Rotate clockwise [or counterclockwise]", 2) "Flex up [or down]", and 3) "Push probe and sweep." These new instructions are derived by using the airway centerline structure, ROI shape and location, predefined major vessel shapes, and optimal ROI biopsy information. "Flex up [or down]" means to flex the bronchoscope's tip up or down. "Push probe and sweep" tells the physician to invoke the EBUS probe and sweep the airway wall to examine the ROI.

For each ROI, a pre-bronchoscopy report is also generated that enables the physician to preview and gain knowledge of the nuances specific to a case before the live bronchoscopic procedure, similar to our previous efforts at generating reports [62, 66]. The report also serves as an archive for the planned live guided procedure.

2. Intra-Operative Image-Guided Bronchoscopy

Given the procedure plan, live intra-operative image-guided bronchoscopy can now occur in the surgical suite. Before beginning the procedure, the guidance strategy receives the live bronchoscopic and RP-EBUS video streams as inputs, shown in FIG. 2.

The guided procedure then proceeds in two distinct stages. First (Navigation), CT-based VB image guidance helps the physician navigate the bronchoscope close to the target ROI along the preplanned airway route. Next (Localization), the method employs a synchronization of a simulated RP-EBUS probe view and a CT-based virtual RP-EBUS view, both residing in virtual CT space, to help guide RP-EBUS invocation at the desired final site. More detail appears below:

1. Navigation: Starting in the trachea, the method presents step-by-step graphical VB views, other graphical cues, and suggested device maneuvers to help the physician navigate the bronchoscope along the preplanned airway navigation route toward the ROI.
2. Localization: When the bronchoscope becomes near the ROI as measured by the proximity of the VB's current guidance position relative to the ROI's location (e.g., <40 mm from the ROI), two steps occur:
   (a) As indications of entering the localization phase, additional guidance cues that specify the ROI's distance from the current guidance pose and a graphical model of a virtual RP-EBUS probe now appear on the graphical display. The physician uses all available graphical information and suggested device maneuvers to make final endoscope movements toward the ROI.
   (b) Upon reaching the preplanned location along the guidance route for invoking the RP-EBUS probe, the guidance system alerts the physician to insert the RP-EBUS probe into the bronchoscope's working channel until the probe's tip appears in the bronchoscopic video. A two-phase registration process now occurs:

Using the bronchoscopic video and VB video sources, the bronchoscope and virtual bronchoscope are registered. This synchronizes the 3D position of the guidance system to the bronchoscope's "real" current pose.

Given the registered bronchoscope's pose as an initialization, the RP-EBUS probe's shape, visible in the bronchoscopic video, and a graphical model of the probe, existing in virtual space, are registered.

The 3D positions of the guidance system's virtual bronchoscope and probe model are now synchronized to the real bronchoscope and EBUS probe at the final planned location for probing the ROI. The physician can now scan the airway wall at the designated location to visualize the ROI.

The method according to the embodiments of the present invention provides the following:

1. The two-phase registration process, which accomplishes the synchronization of the two real devices to the analogous two virtual-space devices.
2. An extensive set of graphical tools and cues, beyond existing graphical tools used by existing image-guided bronchoscopy systems, for facilitating the guidance of this two-device procedure.
3. The complete two-stage process for guiding a procedure using an endoscope and a second complementary device deployed through the endoscope's working channel through a hollow organ system toward an extraluminal ROI.

The remainder of this section describes the two-stage guidance strategy. Section 3 highlights the two-phase registration process used during Localization, while Section 4 gives more detail on the graphical tools.

2.1. Navigation Stage

With the bronchoscope situated in the trachea and the guidance system's display initialized, the physician performs the step-by-step bronchoscope maneuvers suggested by the guidance system so that the bronchoscope's video view approximately mimics the provided planned VB views. Examples of bronchoscope maneuvers are "Move Down" (move the bronchoscope through the airways) and "Rotate CCW" (rotate the bronchoscope counter-clockwise). An optional precise registration between the bronchoscope and VB can then be performed, using previously suggested techniques such as those by Merritt or Khare [30, 39]. This first completed maneuver is then frozen and saved as a "base camp" view to indicate guidance progress.

This process then continues for each successive suggested maneuver. For example, FIG. 3 illustrates the guidance display after completing a "Rotate CCW" maneuver for a live pig study. The frozen Base Camp view shows the real bronchoscope video frame (left) and guidance VB view (right). The next suggested maneuver is "Move Down" (which the physician had just completed before the system freezes it). Other graphical viewers indicate the current guidance position: 1) the 2D coronal CT section view by red cross-hairs and the multi-colored 3D airway tree view by a yellow tin can and blue guidance path.

The methods for this phase were adapted from existing image-guided bronchoscope navigation methods [30, 39], with adaptations made for the guidance instructions for our peripheral guidance problem.

2.2. Localization Stage

When the bronchoscope gets within a prescribed distance from the ROI, the method enters the localization phase. For the case of invoking the EBUS probe, the prescribed distance to trigger this mode switch is on the order of one or two airways from the final preplanned site; we have used the threshold of 40 mm in our tests. At this point, a number of new cues begin to appear on the guidance display to help the physician ascertain how an RP-EBUS probe would be situated with respect to the ROI. FIG. 4 illustrates this new guidance information:

Peripheral Panorama Renderer: An expanded VB view that shows more endoluminal surface area. The green region indicates the upcoming ROI, with greener locations indicating better places to biopsy the ROI (more tissue). A simulated RP-EBUS probe, situated in the position of how a real RP-EBUS probe would enter the bronchoscope's video field of view, also appears. A spotlight indicates where the probe would hit the airway wall if it was pushed further forward.

Peribronchus Renderer—Forward: A view that combines the VB view (in the center), nearby orthogonal tissue, as it would appear to a real RP-EBUS probe, and the simulated probe model.

Peripheral EBUS Match: A view that gives various manifestations of both simulated RP-EBUS views and the real RP-EBUS view, when the real device is invoked. Left view: 2D CT section at the virtual RP-EBUS probe's location; middle view: simulated RP-EBUS view at the same pose; right view: Real EBUS view.

Peripheral Local Renderer: A local airway tree view which also gives a complete graphical model of the combined bronchoscope and RP-EBUS devices. For the model, the black cylinder indicates the bronchoscope tip, the pyramid indicates the video camera's field of view, the small white cylinder indicates the invoked RP-EBUS probe, and the transparent gray plane gives the RP-EBUS probe's 2D scan plane, situated within a plane orthogonal to the bronchoscope tip.

Probe Tracking Viewer: Focuses on the 3D graphical RP-EBUS probe model, used later during probe registration.

The physician continues to follow the guidance system's suggested device maneuvers, using the new display information to assist in maneuvering the bronchoscope appropriately. As in the Navigation Stage, precise registrations can be done if desired, and Base Camp views are frozen and saved.

Figure 5:
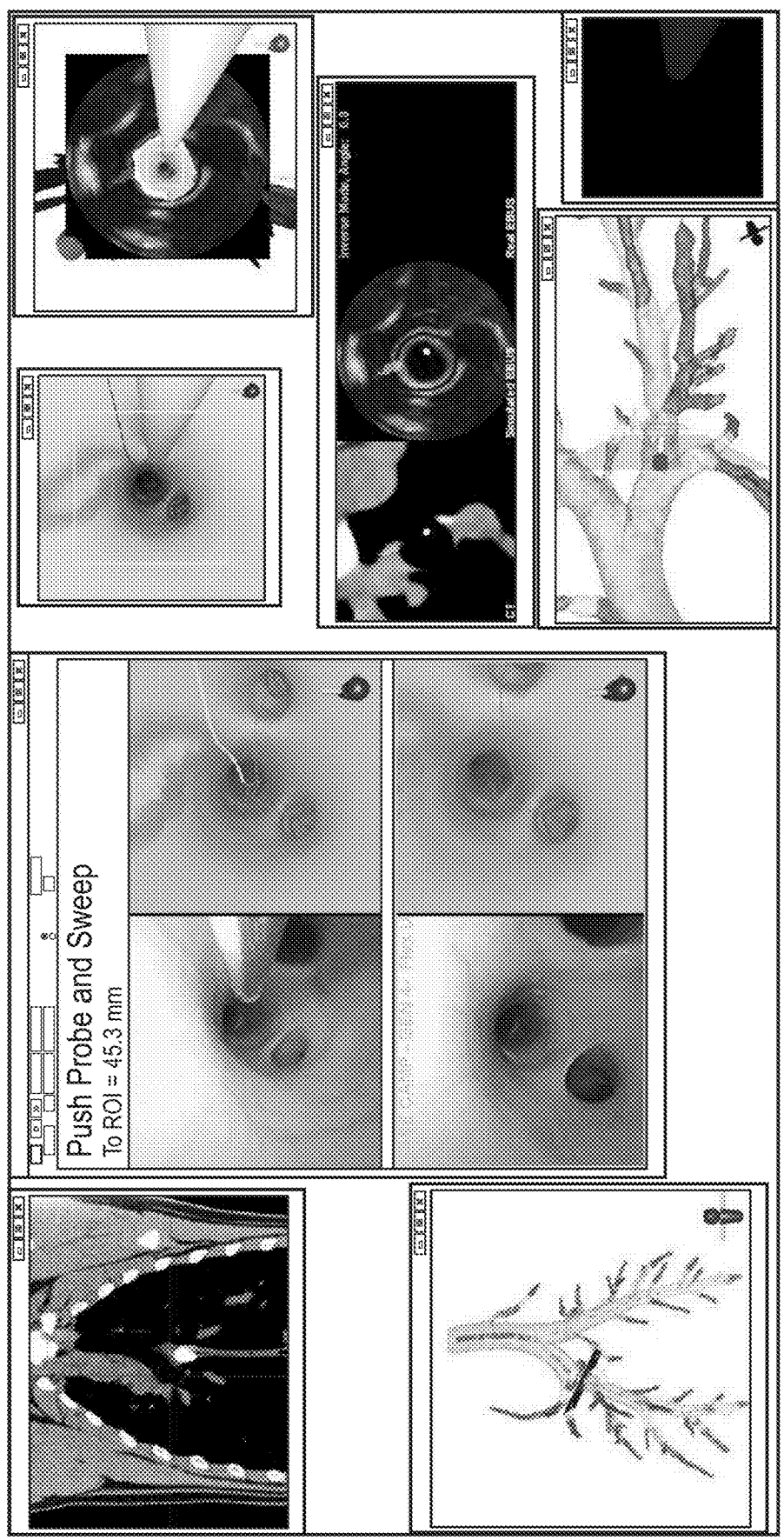
FIG. 5 shows an example guidance display during the end of the first step of localization of the same case as FIGS. 3-4; (The physician has just completed a "Flex Up" maneuver, per the Base Camp view, and has inserted the RP-EBUS probe (seen in the real RP-EBUS video view)

The final suggested bronchoscope maneuver before the second step of Localization is either "Bend Up" ("Flex Up") or "Bend Down" ("Flex Down") to indicate that the device tip should be articulated either up or down. After completing this maneuver, the next maneuver, entails a "Push Probe and Sweep." FIG. 5 gives an example of this situation for the example of FIGS. 3-4. As shown in the figure, the physician completed a "Flex Up" maneuver and then inserted the RP-EBUS probe about 10 mm until it is visible in the bronchoscope's video. Note the similarity of the real probe's shape to the simulated RP-EBUS probe model. The Peri-bronchus Forward Renderer and the simulated RP-EBUS views also show the vestiges of the ROI impinging on the virtual bronchoscope/probe assembly's viewers, and the system is within 11.1 mm of the ROI.

At this point, the second step, two-phase device registration, occurs. In phase 1, the bronchoscope and guidance system's virtual bronchoscope are aligned. Next, drawing upon this alignment of the complete two-device assembly, phase 2 registers the RP-EBUS probe to a probe model residing in virtual space. With these two joint registrations now completed, the physician can now immediately knows where to sweep the EBUS probe to examine the ROI.

Note that it is this two-phase process, described next, which triggers the final positioning of the bronchoscope and the invocation of the RP-EBUS probe.

3. Two-Phase Registration Process

Figure 6:
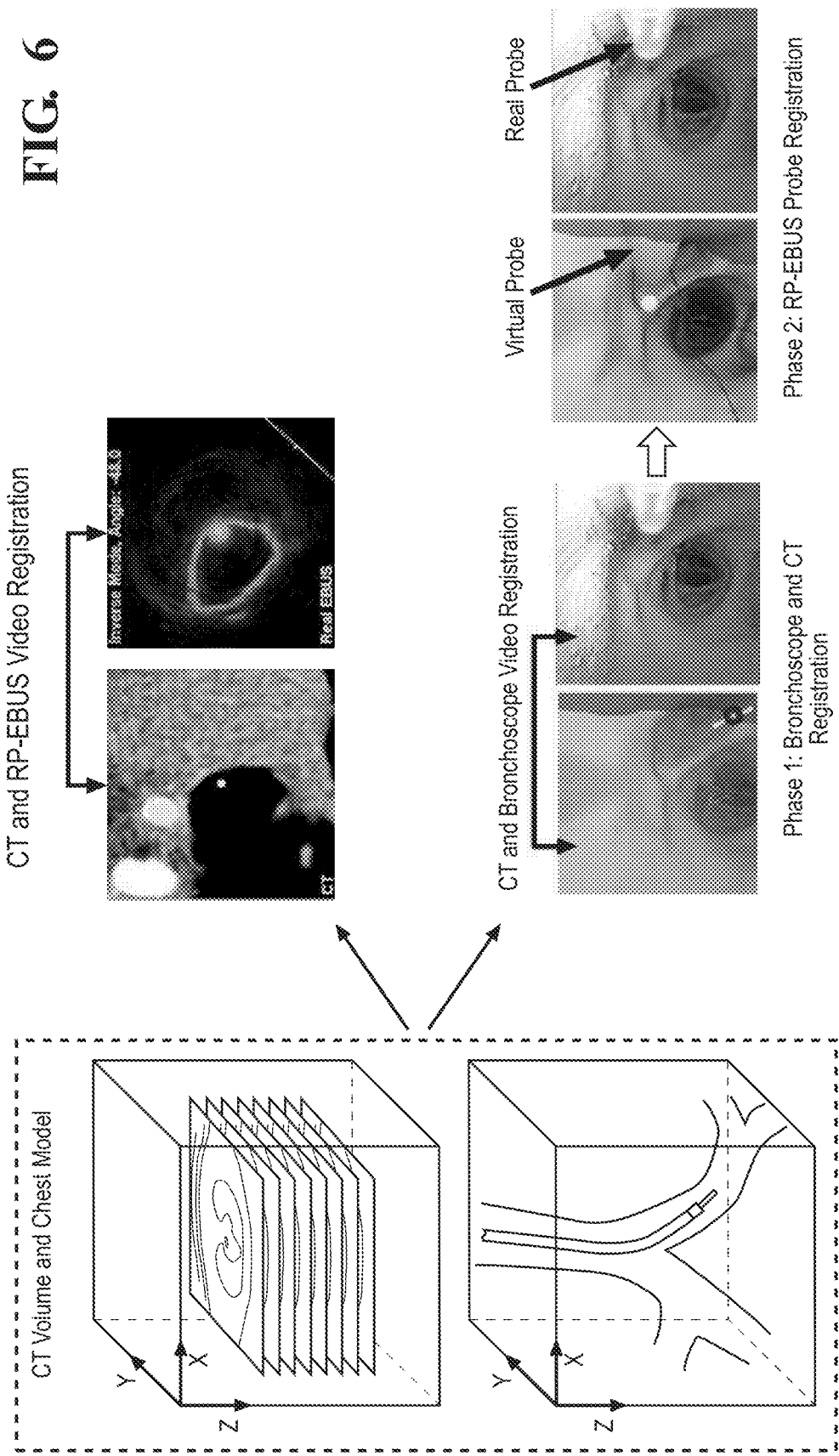
FIG. 6 shows two strategies for CT and RP-EBUS registration; (Top Right: direct 2D-to-3D registration between the 2D RP-EBUS video (right view) and 3D CT volume (left view). Bottom Right: The proposed two-phase registration mechanism to register the bronchoscope and RP-EBUS probe to the reference 3D CT volume)

Beginning at the point when the physician has inserted the RP-EBUS probe during Localization, a two-phase registration method helps guide the final two-device alignment. This involves a coordinated two-phase registration of the real bronchoscope and EBUS probe with the corresponding virtual bronchoscope and virtual EBUS probe model, as shown in FIG. 6. Phase 1 registration of the real and virtual bronchoscopes can be readily accomplished, as discussed below.

Regarding Phase 2 registration of the real and virtual probes, as illustrated in FIG. 6, one natural solution for registering RP-EBUS and CT is to perform a direct 2D to 3D registration between RP-EBUS video and CT volume as done for CP-EBUS and CT registration [68]. However, the ultrasound requires good contact with the airway wall to capture good EBUS views since air will reflect nearly all the ultrasound waves before they arrive at the airway wall [21]. The RP-EBUS uses a direct contact method and usually has poor contact with the airway wall. This fact often results in poor image quality or partially informative EBUS video. Therefore, it is challenging to register the RP-EBUS probe to the CT directly using the RP-EBUS video.

Meanwhile, the RP-EBUS probe is always visible in bronchoscopic video field of view (FOV) upon advancing against the airway wall for sweeping. Therefore, we can find the RP-EBUS probe pose relative to the bronchoscope by tracking the RP-EBUS probe's pose in the bronchoscope's camera view. We also know the pose of the virtual model in 3D CT volume (virtual space). Thus, for this two device problem, we use a two-phase registration mechanism (FIG. 5 bottom right):

1. Phase 1—bronchoscope and CT registration: In the first phase, we register the real bronchoscope pose to the virtual chest CT volume by aligning the VB view to the real bronchoscopic video view [39]. The bronchoscope and CT registration is a standard step for image-guided navigational bronchoscopy, as we used for the earlier Navigation Stage, 2. Phase 2—RP-EBUS probe registration: After Phase 1, the bronchoscope is registered to the CT volume. We then perform two steps to localize the RP-EBUS probe relative to the bronchoscope's camera:
   (a) Segment the RP-EBUS probe from a current bronchoscopic video frame.
   (b) Virtual-to-real RP-EBUS probe registration to find the RP-EBUS pose relative to the bronchoscope.

Upon completion, we can then find the RP-EBUS probe pose in 3D CT volume by forming two consecutive rigid transformations.

The following describes the two-phase registration method in detail. Subsection 3.A first lays out the pertinent 3D chest-to-probe geometry. Subsections 3.B and 3.C then describe each of the two phases of the registration method. Subsection 3.D then describes probe segmentation, while Subsection 3.E summarizes implementation of the guidance strategy and two-phase algorithm.

3.A. RP-EBUS Probe Geometry

Figure 7A:
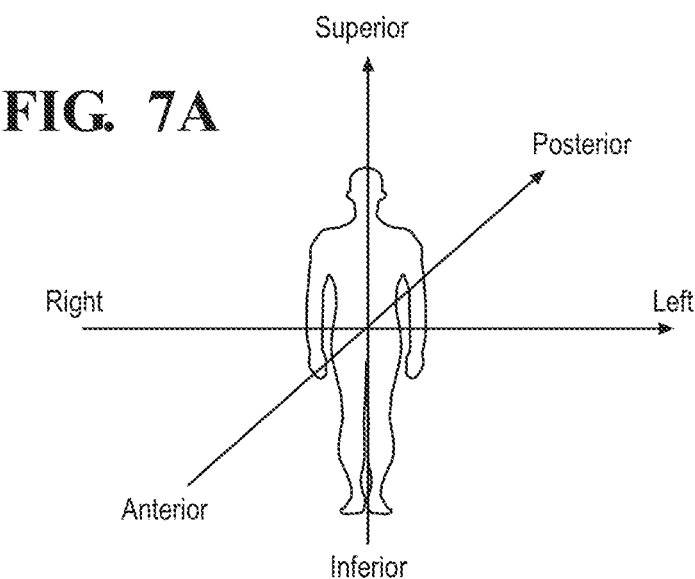
FIG. 7A-7C show 3D CT chest space and chest model.

First, the relevant coordinate system and related geometric transformations that help represent a view site in a 3D CT-based virtual space are defined. As illustrated in FIG. 7A, a Left, Posterior, Superior (LPS) 3D coordinate system is used for the virtual space. The positive Z-axis extends downward along the page, the positive X-axis extends toward the page's right border, and the positive Y-axis extends directly into the page. A view site is defined as a view/navigation pose within the 3D image space. Therefore, a view site consists of a 3D position and a 3D view direction. The position of a view site in the CT volume is defined as $$p = (x, y, z), \qquad (1)$$

where x, y, and z refer to coordinate values for the X, Y, and Z axes, respectively. Three standard Euler angles can describe the direction of a view site as $$d = (\theta, \phi, \psi), \qquad (2)$$

where θ, ϕ, ψ represent the rotations about the X, Y, and Z axes, respectively. Therefore, the pose of a view site in virtual space can be defined by $$\Theta = (p, d) = (x, y, z, \theta, \phi, \psi). \qquad (3)$$

Figure 7B:
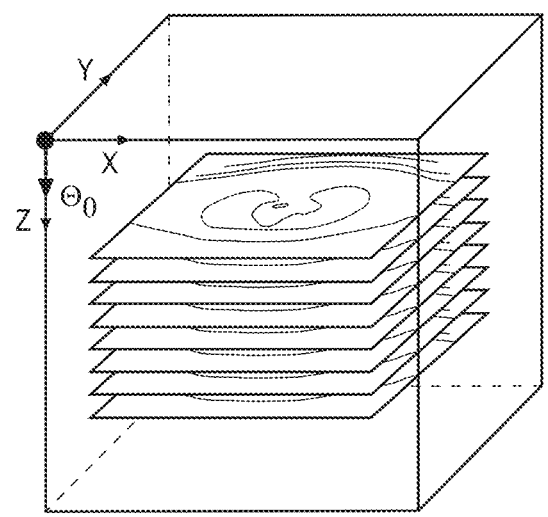
Figure 7C:
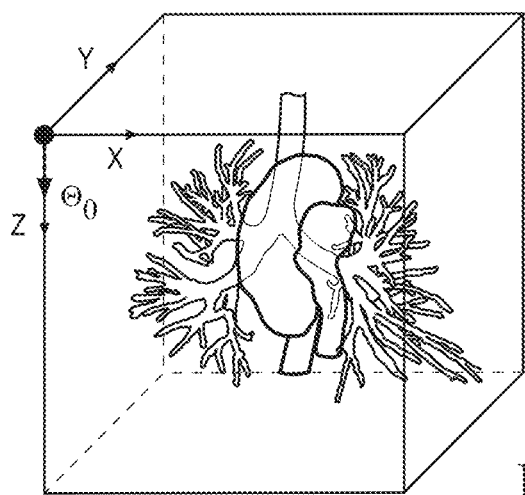
Figure 8:
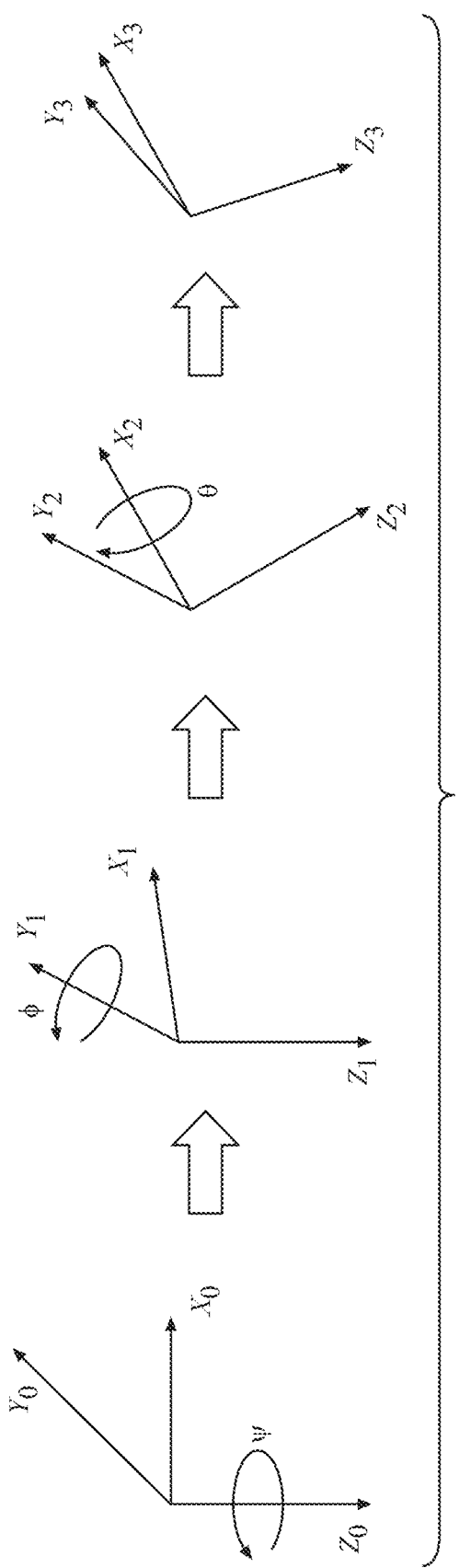
FIG. 8 shows Euler angle rotation sequence; (Rotations begin about the Z-axis, $Z_0$, followed by the newly rotated Y-axis, $Y_1$, and ending with the twice rotated X-axis, $X_2$)
Figure 9:
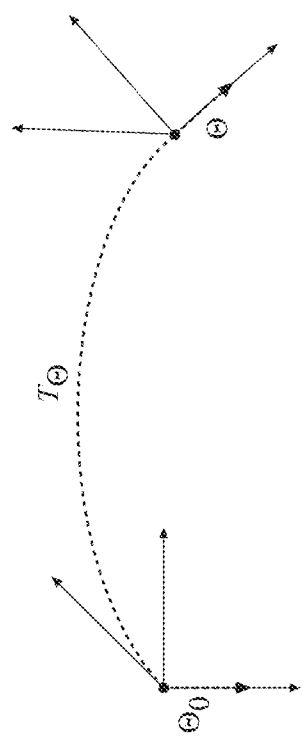
FIG. 9 shows a rigid body transform from $\Theta_0$, at origin to a pose $\Theta$.

The present method employs view orientation using Euler angles and three intrinsic rotations, performed in a specific order with regard to the set of three orthogonal volume axes. Rotations begin about the Z-axis, followed by the newly rotated Y-axis, and ending with the twice rotated X-axis. For transformations, we still need to define an initial pose $$\Theta_0 = (p_0, d_0) = (0, 0, 0, 0, 0, 0) \qquad (4)$$

at origin $p_0=(0,0,0)$ with canonical view direction. The view site at the initial pose is represented by the red arrow extending from $\Theta_0$ in FIG. 7B. FIG. 8 demonstrates the correct order of Euler angle rotations with regard to 3D space axes. FIG. 7C depicts the 3D chest model, derived from the patient's 3D scan, rendered in 3D virtual chest space. It consists of the airway tree, aorta and pulmonary artery.

Given these definitions, the bronchoscope and RP-EBUS probe's location can now be described using a view site and its pose in the virtual space.

The pose can be treated as rigid body transformation and described with a 4×4 homogeneous matrix 1.

$$T = \begin{bmatrix} R & t \\ 0^T & 1 \end{bmatrix} = \begin{bmatrix} r_{11} & r_{12} & r_{13} & t_x \\ r_{21} & r_{22} & r_{23} & t_y \\ r_{31} & r_{32} & r_{33} & t_z \\ 0 & 0 & 0 & 1 \end{bmatrix} \qquad (5)$$

To apply a full rigid body transform, we append 1 to any 3D points $X=[x, y, z]^T$ in 3D CT chest space to obtain a point in homogeneous coordinates:

$$X = \begin{bmatrix} X \\ 1 \end{bmatrix} = \begin{bmatrix} x \\ y \\ z \\ 1 \end{bmatrix} \qquad (6)$$

with this homogeneous matrix, the pose can be expressed as $$X_\Theta = T_\Theta X_{\Theta_0} = \begin{bmatrix} R_\Theta & t_\Theta \\ 0^T & 1 \end{bmatrix} \begin{bmatrix} X_{\Theta_0} \\ 1 \end{bmatrix} = \begin{bmatrix} R_\Theta X_{\Theta_0} + t_\Theta \\ 1 \end{bmatrix}, \qquad (7)$$

where X and $X_{\Theta_0}$, are the representations of current 3D points $X=[x, y, z]^T$ and initial 3D points $X_{\Theta_0}=[0,0,0]^T$ in homogeneous coordinates by appending 1, respectively. FIG. 6 illustrates the rigid transform from $\Theta_0$ at origin to a pose $\Theta$.

In addition, twists can be used to represent a rigid body transform. The twist set can be represented as $$\xi = \begin{bmatrix} w & v \\ 0 & 0 \end{bmatrix} \in \mathfrak{se}(3), \text{ with } w \in \mathfrak{so}(3) \text{ and } v \in \mathbb{R}^3, \qquad (8)$$

where w is the angular velocity and indicates the rotational part of the rigid body motion. v is the linear velocity and indicates the transnational part of the rigid body motion. All twists ξ form a the tangent space (or Lie-algebra) $\mathfrak{se}(3)$ corresponding to the Lie-group $\mathbb{SE}(3)$. Each twist can be parameterized by a 6D vector of twist coordinates $$\xi = \begin{bmatrix} w \\ v \end{bmatrix} = [\omega_1, \omega_2, \omega_3, v_1, v_2, v_3]^T \in \mathbb{R}^6. \qquad (9)$$

The homogeneous matrix of a pose Θ in (7) can be represented using twists ξ as $$T_\Theta = \exp(\xi(\Theta)) \in \mathbb{SE}(3) \qquad (10)$$

More details of the twist can be found in [37, 60].

Therefore, as shown in FIG. 10, in the 3D CT chest space, the pose of bronchoscope camera $\Theta_b$ can be represented on a pre-planned path within the airway as $$\Theta_b = (x_b, y_b, z_b, \theta_b, \phi_b, \psi_b). \qquad (11)$$

We can estimate $\Theta_b$ with any CT-bronchoscope registration algorithm during the image-guided bronchoscopy and then find the bronchoscope's pose in 3D CT chest space from $\Theta_0$ at origin as [30, 39]

$$X_{\Theta_b} = T_{\Theta_b} X_{\Theta_0}, \qquad (12)$$

Now, assuming we can obtain the bronchoscope camera pose $\Theta_b$ from the image-guided bronchoscopy procedure, the next step is to model the relative geometry between the bronchoscope camera and the RP-EBUS probe. Using the pose of bronchoscope camera $\Theta_b$ and its homogeneous matrix $T_{\Theta_b}$ similar to (5) can bring us from the 3D chest coordinate (X, Y, Z) to a local coordinate $(X_b, Y_b, Z_b)$ at current bronchoscope camera pose $\Theta_b$, as shown in FIG. 10.

Moreover, after navigating the bronchoscope into the final airway of interest, the physician now inserts and advances an RP-EBUS probe through the bronchoscope's working channel, e.g., as illustrated in FIG. 5. While the working channel end and the objective lens are both on the distal end of the bronchoscope, they still have a relative geometry to consider between the bronchoscope camera and the RP-EBUS probe transducer. Also, even though this relative geometry can be constrained, the RP-EBUS probe is non-rigid in practice. To account for this, we need to consider another 6 DOF transformation $\Theta_{eb}$ between bronchoscope and RP-EBUS probe in this local coordinate $(X_b, Y_b, Z_b)$ at bronchoscope camera pose $\Theta_b$, as shown in FIG. 10. In the implementation of the two-phase registration mechanism, we use a region-based pose estimation algorithm to find this relative pose $\Theta_{eb}$ from the RP-EBUS probe segmentation mask [59].

Now, with the known bronchoscope camera pose $\Theta_b$ and the RP-EBUS probe pose relative to the bronchoscope camera $D_{eb}$, we can find the RP-EBUS probe pose $\Theta_e$ in 3D chest coordinates (X, Y, Z) as (FIG. 10)

$$X_{\Theta_e} = T_{\Theta_e} X_{\Theta_0} = T_{\Theta_{eb}} X_{\Theta_b} = T_{\Theta_{eb}} T_{\Theta_b} X_{\Theta_0}, \quad (13)$$

where $X_{\Theta_b}=[x_b, y_b, z_b, 1]^T$ and $X_{\Theta_e}=[x_e, y_e, z_e, 1]^T$ are the representations of the current 3D locations of the bronchoscope and RP-EBUS probe respectively, written as 4×1 column vectors in homogeneous coordinates by appending 1, respectively. $\Theta_e$ gives the pose of the RP-EBUS probe transducer and represents a vector in 3D CT chest space. The RP-EBUS probe transducer captures a 360° scanning plane, which is perpendicular to the probe. Therefore, the probe transducer pose $\Theta_e$ is located at the center of the scanning plane and is normal to it.

Given known RP-EBUS probe specifications (distal end diameter and scanning range), we can derive the virtual RP-EBUS probe's pose and the corresponding 2D cross-section scanning area (e.g., FIG. 6, top right, left view). To compute a 2D cross-section view, we find all 3D positions within the scanning area and interpolate their HU values from the CT volume [69].

3.B. Phase 1—Bronchoscope and CT Registration

We now describe the first phase of our two-phase registration method, shown in FIGS. 11A and 11B. The purpose of the first phase is to estimate $\Theta_b$ in (13), the bronchoscope pose in 3D CT chest space. As stated earlier, several strategies can be used to find the bronchoscope pose in the CT volume. We used the VBN methods of [30, 39].

Note that other techniques can be used to find the bronchoscope pose in 3D CT chest space. For example, electromagnetic navigation-based guidance systems can find the bronchoscope pose $\Theta_b$ through an attached dedicated sensor in the electromagnetic field [25]. Similarly, systems drawing on bronchoscope shape-sensing technology can track the location, shape, and orientation information through the embedded fiber optic shape sensor [1].

3.C. Phase 2—RP-EBUS Probe Registration

After phase 1, the real bronchoscope is registered to the CT-based virtual bronchoscope with a known bronchoscope pose $\Theta_b$. We next must register the virtual RP-EBUS probe model to the real RP-EBUS probe, which has been inserted into the bronchoscope's working channel. Per FIG. 10, both probes abide by the same bronchoscope tip configuration (working channel). To facilitate registration, we use the real probe's shape as it appears in the bronchoscopic video, shown in FIG. 12. Phase 2 now accomplishes this registration to give $\Theta_{eb}$ in (13), the RP-EBUS probe pose relative to the bronchoscope camera.

There are two popular solutions for instrument pose estimation in a minimally invasive procedure. The first solution considers a simplified model and utilizes a projective model of the instrument to estimate the 3D pose from a 2D video frame [9, 10, 44]. This method requires good line borders for the device in the scene, which is difficult to extract for the RP-EBUS probe, which has transparent boundaries. Therefore, we did not choose this method to find the pose of the RP-EBUS probe.

We use a second solution, which involves a region-based alignment method. Such methods consider the object's shape and find an object's pose with object region alignment in video frames [2, 47, 59]. These methods define a level set function, which handles the shape model and curve evolution [45].

Figure 12:
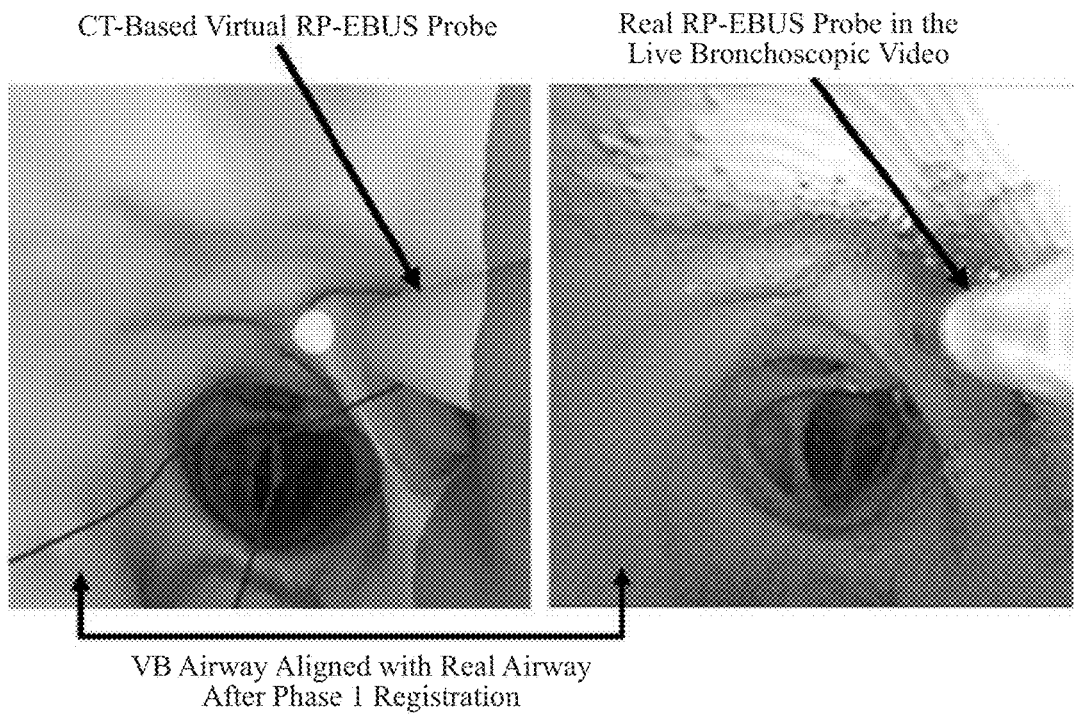
FIG. 12 shows Phase 2—RP-EBUS probe registration (case 20349.3.48); (Left: CT-based VB view after phase 1 bronchoscope and CT registration (VB airway aligned with real airway after phase 1 registration); Right: Real bronchoscopic video view)

Two region-based forms of the RP-EBUS probe are taken into account for the alignment method:

1. Real probe: appears in the captured bronchoscopic video frame (FIG. 12 right). As discussed Section 2.3.D, we use a semantic segmentation method to segment the probe.
2. Virtual probe-abides by the bronchoscope tip's geometry/model (FIG. 12 left). Using the real known specifications of the RP-EBUS probe, we create a computer graphics model that gives a shape identical to the real probe's shape. This 3D probe model resides in the known virtual space of the CT-based VB view. We can freely move this probe model with virtual space to accomplish registration using the bronchoscope camera's parameters during the probe registration.

Figure 13:
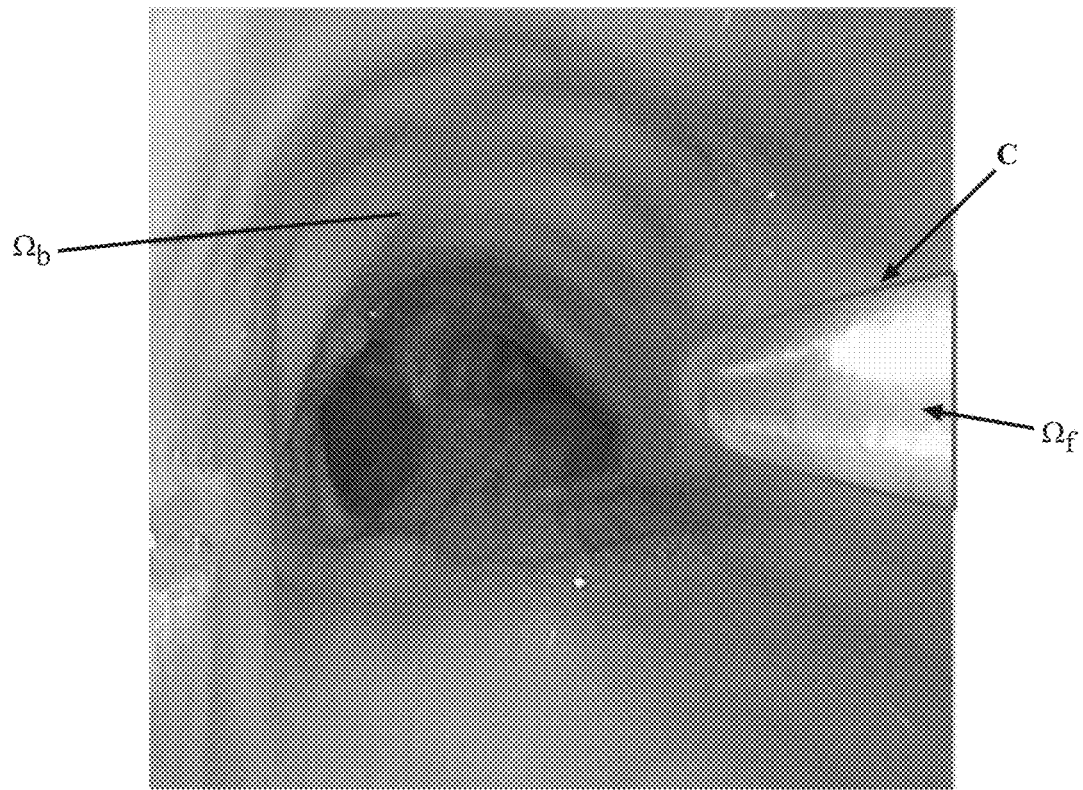
FIG. 13 shows representation of the closed curve C, the foreground RP-EBUS probe $\Omega_f$, and the background airway $\Omega_b$ (case 21405.168)

Regarding the alignment method, we denote a bronchoscopic video image by I in the color image domain $\Omega \in \mathbb{R}^2$. A pixel location $x=[x,y]^T \in \mathbb{R}^2$ has a RGB value of $I(x)=y$. Assuming known calibration parameters for the bronchoscope, we can project the 3D virtual probe model into the 2D image plane and obtain a silhouette. Given this probe silhouette region in the 2D image plane, we can define a 2D closed curve of the object in the image as C, as illustrated in FIG. 13. The image domain $\Omega$ can separate the image into two regions: an interior region representing the foreground $\Omega_f$ and an exterior region $\Omega_b$ representing the background. In our case, the boundary between the RP-EBUS probe and the airway background form the 2D closed curve C. The interior region of the probe forms the foreground $\Omega_f$ and the exterior region, which represents the airway, forms the background $\Omega_b$, as shown in FIG. 13.

A level set function $\Phi$ is a Lipschitz continuous function, which defines the curve C as the zero level [2, 47]

$$C = \{x \in \mathbb{R}^2 \mid \Phi(x) = 0\} \quad (14)$$

We can define a level set function to measure the Euclidean distance between any pixel location to the contour C [47]

$$\Phi(x) = \begin{cases} d(x, C) & \forall x \in \Omega_b \\ -d(x, C) & \forall x \in \Omega_f \end{cases} \quad (15)$$

with a signed distance function $$d(x, C) = \min_{x_C \in C} \|x - x_C\| \quad (16)$$

where d(x, C) represents the minimum distance from a pixel location x to a location on the probe's boundary curve $X_c$.

The region-based alignment for a 2D closed curve tries to find the difference between the foreground and background region statistics. The level set function $\Phi$ captures the random point-by-point differences of the desired contour. The following posterior probability function can represent the shape of the complete contour [6, 47]

$$P(\Phi \mid I) = \prod_{x \in \Omega} (H_e(\Phi(x))P_f(x) + (1 - H_e(\Phi(x)))P_b(x)), \quad (17)$$

where $H_e$ is a smoothed Heaviside step function, and $P_f(x)$ and $P_b(x)$ are per-pixel foreground and background region membership probability density functions. (17) describes the posterior probability of the level set function Φ give a bronchoscopic video image I. Here, the Heaviside function is defined as [59]

$$H_e(\Phi(x)) = \frac{1}{\pi}\left(-\text{atan}(s \cdot \Phi(x)) + \frac{\pi}{2}\right), \quad (18)$$

where s is a parameter to control the pitch of the smoothed transition.

During the 2D region-based alignment, the closed curve C evolves to maximize P(Φ|I) in (17), constrained by the shape prior in the form of the 3D probe model. Because the level set function Φ depends only on the pose, i.e., Φ(x(Θ)), therefore the algorithm can evolve the probe contour C and update the probe pose.

Assume $\Theta_{crb}$ is the initial virtual probe pose relative to the bronchoscope camera, to find the real RP-EBUS probe pose relative to the bronchoscope camera $\Theta_{eb}$, the algorithm maximizes P(Φ|I) to find $\Theta_{ec}$, the pose difference between the virtual and real probe. However, instead of updating a 6D pose $\Theta_{ec}$ directly, the algorithm updates the twist $\xi_{ec}$, of a rigid body motion in twist coordinates (9), i.e. $\Phi(X(\xi_{ec}))$.

Assuming pixel-wise independence, we can describe the energy function by the negative log of (17) given the image $$E(\xi_{ec'}) = -\sum_{x\in\Omega}\log(H_e(\Phi(x(\xi_{ec'})))P_f(x) + (1 - H_e(\Phi(x(\xi_{ec'}))))P_b(x)). \quad (19)$$

The region-based method can estimate the pose parameters with respect to twist coordinate $\xi_{ec}$, by finding the optimal solution to separate the foreground and background regions.

The localized appearance model can better capture spatial variations of the probe's contour during the region-based alignment [29, 31]. The global membership probabilities $P_f(x)$ and $P_b(x)$ are further replaced with the average posteriors from local region membership probabilities as $$\overline{P}_f(x) = \frac{1}{\sum_{i=1}^n B_i(x)}\sum_{i=1}^n P_{f_i}(x)B_i(x) \quad (20)$$

$$\overline{P}_b(x) = \frac{1}{\sum_{i=1}^n B_i(x)}\sum_{i=1}^n P_{b_i}(x)B_i(x) \quad (21)$$

where $P_{f_i}(x)$ and $P_{b_i}(x)$ are the local region membership probabilities from a local histogram i. Here, $B_i$ is the masking function to indicate whether a pixel x lies within a local region or not $$B_i(x) = \begin{cases} 1, & x \in \Omega_i \\ 0, & x \notin \Omega_i \end{cases} \quad (22)$$

With this modification, the energy function in (19) becomes $$E(\xi_{ec'}) = -\sum_{x\in\Omega}\log(H_e(\Phi(x(\xi_{ec'})))\overline{P}_f(x) + (1 - H_e(\Phi(x(\xi_{ec'}))))\overline{P}_b(x)), \quad (23)$$

(23) is not directly applicable to the Gaussian-Newton optimization. We can rewrite (23) by $$E(\xi_{ec'}) = \sum F(x, \xi_{ec'}), \quad (24)$$

where $$F(x, \xi_{ec'}) = -\log(H_e(\Phi(x(\xi_{ec'})))\overline{P}_f(x) + (1 - H_e(\Phi(x(\xi_{ec'}))))\overline{P}_b(x)) \quad (25)$$

They can then be expressed in the form of a re-weighted nonlinear least-squares estimation and solved with a Gaussian-Newton algorithm $$E(\xi_{ec'}) = \frac{1}{2}\sum_{x\in\Omega}\psi(x)F^2(x, \xi_{ec'}), \text{ with } \psi(x) = \frac{1}{F(x, \xi_{ec'})} \quad (26)$$

More details of the optimization of (26) are described in Tjaden's paper [59].

In each step, the algorithm update a corresponding twist as $\Delta\hat{\xi}_{ec}$, and the current probe pose can be calculated as the composition of the matrix exponential of $\Delta\hat{\xi}_{ec}$, with the previous pose estimate $$T_{\Theta_{ec'}} \leftarrow \exp(\Delta\hat{\xi}_{ec'})T_{\Theta_{ec'}}. \quad (27)$$

With the estimated bronchoscope pose $X_{\Theta_b}$, we can calculate the final RP-EBUS probe pose as $$X_{\Theta_e} = T_{\Theta_{eb}}X_{\Theta_b} = T_{\Theta_{ec'}}T_{\Theta_{crb}}X_{\Theta_b} = T_{\Theta_{ec'}}T_{\Theta_{crb}}T_{\Theta_{bc}}T_{\Theta_c}X_0 \quad (28)$$

Figure 14:
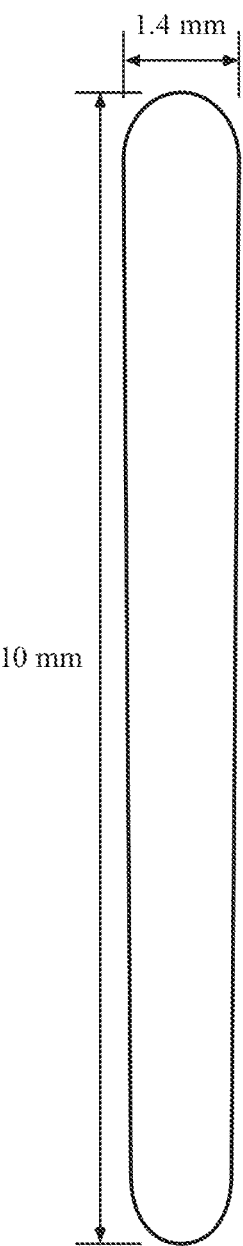
FIG. 14 show an Olympus UM-S20-17S RP-EBUS probe mesh model generated from the Blender software [7]; (The virtual RP-EBUS has a length of 10 mm and a diameter of 1.4 mm)

The region-based pose estimation draws on a 3D mesh model for the virtual RP-EBUS probe. We generate a round-capped cylinder in actual dimensions of an Olympus UM-S20-17S RP-EBUS probe using the Blender software package to mimic a real RP-EBUS probe [7]. In particular, the RP-EBUS mesh model has a diameter of 1.4 mm, which has the same diameter as the distal end of an Olympus UM-S20-17S RP-EBUS probe. Note that the entire length of an RP-EBUS probe (2150 mm) is not necessary for RP-EBUS probe registration. Therefore, as shown in FIG. 14, we use a length of 10 mm for the probe mesh model. The round-capped end is added to mimic the shape of a probe distal end for better registration results.

The virtual RP-EBUS probe model has dense 2382 vertices equally sampled across the visible surface to ensure the best performance of region-based pose estimation. Note that this model can also be applied to a needle. However, a more specific mesh model for the needle may work better.

Tjaden's region-based pose estimation includes a template matching strategy for pose detection [59]. The template matching can help re-locate the target object in the scene to its best matching location and provide a good pose initialization before the algorithm refine the object's pose. In our case, the RP-EBUS probe is always advanced from the bronchoscope's working channel, which is on the right side of the bronchoscope's camera. Therefore, its location is constrained to the right side of the bronchoscopic video frame, and we did not need to use template matching in our case.

Another difference between our implementation and Tjaden's algorithm is the object boundary condition. In Tjaden's algorithm, the vertices of the mesh object near the object boundaries are used to calculate temporally consistent local color (TCLC) histograms for pose estimation [59]. In our case, the probe object is always from the right side of a bronchoscopic video frame and is partially visible in the scene. Therefore, in our implementation, we omit those vertices near the video frame boundary to prevent a "false" probe boundary cut by the bronchoscope's FOV.

3.D. RP-EBUS Probe Segmentation

The following describes how the segmentation of the RP-EBUS probe is implemented as it appears in a typical bronchoscopic video frame. For the present work, we implemented two approaches. The first one, focused on here, entails automatic deep-learning-based segmentation. The second approach is a simple interactive drawing approach we implemented as a fail-safe approach; this method is part of the Peripheral Segmenter tool. Reference gives complete detail on these methods.

Unlike a surgical scenario, during live bronchoscopy, the background scene can change rapidly as the physician moves the bronchoscope. On the other hand, the Olympus UM-S20-17S radial miniature probe (1.4 mm distal-end diameters; 20-MHz transducer) has a transparent catheter around the transducer. It is difficult to discriminate the transparent catheter of the probe from the airway background because they can refract the airway colors behind them. This fact can make it confusing to find the true boundary of the RP-EBUS probe. Therefore, it is challenging to directly apply the region-based pose estimation to the bronchoscopic videos. Instead, to obtain robust pose estimation results in our work, we first segment the RP-EBUS probe in the bronchoscopic video and then apply the region-based pose estimation method to the segmentation result.

Because the transparent catheter of an RP-EBUS probe can refract the airway colors behind it, it is challenging to apply low-level image processing techniques to segment the RP-EBUS probe from the bronchoscopic videos. Therefore, we adopt a deep learning approach in our work; i.e., semantic segmentation. Unlike a general classification/detection task, semantic segmentation understands images at the pixel level: assigning the object classes at each pixel in the image, or "background" otherwise [16, 22, 41]. Among all the state-of-the-art deep learning models for semantic image segmentation, we chose the popular Deeplab v3+ because of its high performance on benchmarks: PASCAL VOC2012 dataset (89.0%) and Cityscapes dataset (82.1%) measured in terms of pixel intersection-over-union averaged across all classes (mIOU) [14, 16, 22]. The Deeplab v3+ further improves upon the performance of Deeplab v3 by introducing a decoder module to refine the segmentation results with an emphasis on object boundaries [14].

Figure 15:
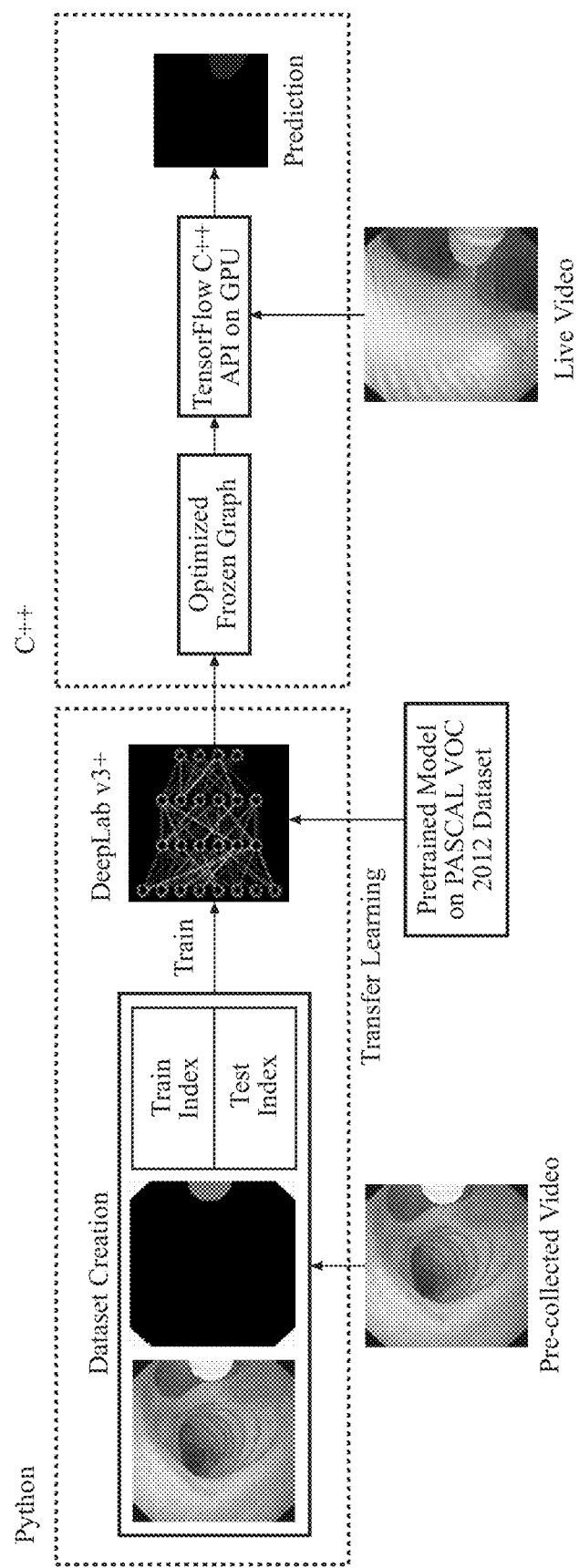
FIG. 15 shows semantic segmentation workflow on bronchoscopic video data.

To use Deeplab v3+ semantic segmentation, we started with a pre-trained model trained on ImageNet [50], MS-COCO [32], and PASCAL VOC 2012 datasets with a Xception network backbone [15]. This pre-trained model has a segmentation performance of 87.8% in terms of mIOU on the PASCAL VOC test set. We then applied transfer learning, replaced the last layer of the network for our RP-EBUS probe data sets, and then improved the network's weights for our task during our training process. We drew on a data set from pre-collected bronchoscopic videos with a visible RP-EBUS probe using our devices and video centers. The data set includes annotate images from phantom patient cases and animal studies. Under python, we then trained the Deeplab v3+ model using our data set with to arrive at the best mIOU score over all images in the data set. Finally, we loaded this pre-trained model into our C++ software system and used it to predict the RP-EBUS probe segmentation mask for a live bronchoscopic video frame during image-guided bronchoscopy. FIG. 15 summarizes the work flow for implementing semantic segmentation.

For human studies, the videos were collected from two human patients using Olympus BF-H190 and BF-1TH190 bronchoscopes on two human cases with an Olympus CV-190 video center at the Penn State Milton S. Hershey Medical Center. The full video output size for the Olympus CV-190 video center is 1920×1080. Both Olympus BF-H190 and BF-1TH190 bronchoscopes capture HD videos (1920×1080) and an actual bronchoscopic video frame size of 1069×1098 after distortion correction. We used an Olympus UM-S20-17S RP-EBUS probe for all the studies for all phantom, animal, and human cases. We trained all the Deeplab v3+ models with TensorFlow 13.2+CUDA 10.0 on a Dell Precision 7920 tower (64-bit Windows 10, 64 GB RAM, Intel Xeon Gold 6138 20-core 2.0 GHz), including an NVIDIA RTX 2080 Ti graphics card and a Matrox Clarity HD frame grabber.

We used the best mIOU score model to achieve better segmentation results during later predictions for all the phantom, animal, and human cases. The best Deeplab v3+ model for the phantom data set had an mIOU of 96.4%, for animal data set the best mIOU was 97.0%, and for the human data set the best mIOU was 93.8%. The detailed training and testing procedures, including all parameters for this process, are in [69].

3.E. Algorithm for Two-Phase RP-EBUS Registration

Algorithm 1 gives a summary of the proposed two-phase RP-EBUS registration mechanism. The algorithm initializes with the following elements:

1. Real bronchoscopic video frame with visible RP-EBUS probe at: a) an unknown bronchoscope pose $\Theta b$; and b) an unknown RP-EBUS probe local pose $\Theta_{eb}$ as well as a corresponding global pose $\Theta_e$. This bronchoscopic video frame view is our target bronchoscope and RP-EBUS probe poses to align to.

2. Virtual models: a) a CT-based airway tree surface model [27]; and b) a 3D RP-EBUS probe mesh model. Both phases of the registration method require image-based rendering for image alignment. Therefore, we need to generate and load the image-based rendering models for the airway tree and RP-EBUS probe before registration.

3. Bronchoscope camera parameters: To project the 3D rendering models to the 2D image plane, we also must calculate the bronchoscope's calibration parameters before registrations [8].

During the first phase of registration, we first initialize virtual bronchoscope view at the known bronchoscope pose $\Theta_c$. Our method then updates bronchoscope pose $\Theta_b$ using bronchoscopic video frame and virtual bronchoscope view until convergence.

After phase 1, the estimated bronchoscope pose $\Theta_b$ can bring the camera from origin to the bronchoscope camera location. Our method now apply the second phase of registration. We first use the bronchoscopic video frame to compute the segmentation mask ($\Omega_f$ and $\Omega_b$). Our method then estimates RP-EBUS probe local pose $\Theta_{eb}$ using this bronchoscopic video frame segmentation mask and virtual RP-EBUS probe view until convergence. Finally, we can calculate the RP-EBUS global pose $\Theta_e$ using the estimated bronchoscope pose $\Theta_b$ and RP-EBUS probe local pose $\Theta_{eb}$ from the two phases.

---
Algorithm 1 Two-phase RP-EBUS registration
---
Initializations:
  1) Real bronchoscopic video frame with visible RP-EBUS probe at:
    a) unknown bronchoscope pose $\Theta_b$
    b) unknown RP-EBUS probe local pose $\Theta_{eb}$ and global pose $\Theta_e$
5:  2) Virtual models:
    a) CT-based airway tree surface model
    b) 3D RP-EBUS probe mesh model
  3) Bronchoscope camera parameters
10:  // Phase 1 - Bronchoscope and CT registration
  Initialize virtual bronchoscope view at known bronchoscope pose $\Theta_c$
  repeat
    Using bronchoscopic video frame and virtual bronchoscope view to update bronchoscope pose $\Theta_b$
  until convergence
15:  // Phase 2 - RP-EBUS probe registration
  Using bronchoscopic video frame to compute the segmentation mask ($\Omega_f$ and $\Omega_b$)
  Initialize virtual RP-EBUS probe view at known local pose $\Theta_{c,b}$
  repeat
    Using video frame segmentation mask and virtual RP-EBUS probe view to update RP-EBUS probe local pose $\Theta_{eb}$
20: until convergence
  Compute the RP-EBUS global pose $\Theta_e$ using bronchoscope pose $\Theta_b$ and RP-EBUS probe local pose $\Theta_{eb}$
  return RP-EBUS probe global pose $\Theta_e$
---

During the first phase, The bronchoscope-CT registration method reduces the repeated VB rendering process to only once by mapping the real bronchoscopic video frame to VB inversely [39]. Also, the method does not require a large image resolution for successful registration. Therefore, it always down-scales image size to smaller than 300×300 before registration. The method can run continuously at >300 frames/s, which is well beyond the bronchoscopic video frame rate of 30 frames/s.

During the second phase, our RP-EBUS probe registration method speeds up the pose estimation using a three-level image pyramid scheme from coarse to fine and an OpenCV parallel data processor to further speed up the optimization with multi-threading [43]. For a video frame size of 500×500, the overall runtime performance is 75-110 frames/s depending on the RP-EBUS probe's distance to the bronchoscopic camera. For an HD video frame size of 1224×1224, the overall runtime is 16-20 frames/s.

For probe segmentation during the second phase, we use TensorFlow and NVIDIA CUDA to run the Deeplab v3+ prediction on the GPU. Because an invocation of a Tensor-Flow session tends to require a relatively slow initialization, the request will have high latency during the first run of prediction. Therefore, the first prediction is always slow. However, the prediction request will be magnitude faster after the warm up. For a 500×500 color bronchoscopic video frame, the first run can take 5-10 seconds. However, from the second prediction, the runtime is 25-50 frames/s. Similarly, for a 1224×1224 video frame, the first prediction takes 7-11 seconds. From the second prediction request, the average runtime is 16-20 frames/s.

The whole two-phase registration procedure takes 70-80 seconds on average, including user interactions.

4. System Implementation

A planning and image-guided bronchoscopy system is prototyped, tailored to examining peripheral ROIs in the lungs. The complete system consists of the tools needed to execute the two-part work flow of pre-operative procedure planning, followed by live image-guided bronchoscopy system. The software resides on a standard Windows PC and interfaces readily to the surgical suite's endoscopy hardware during live guidance.

Figure 16:
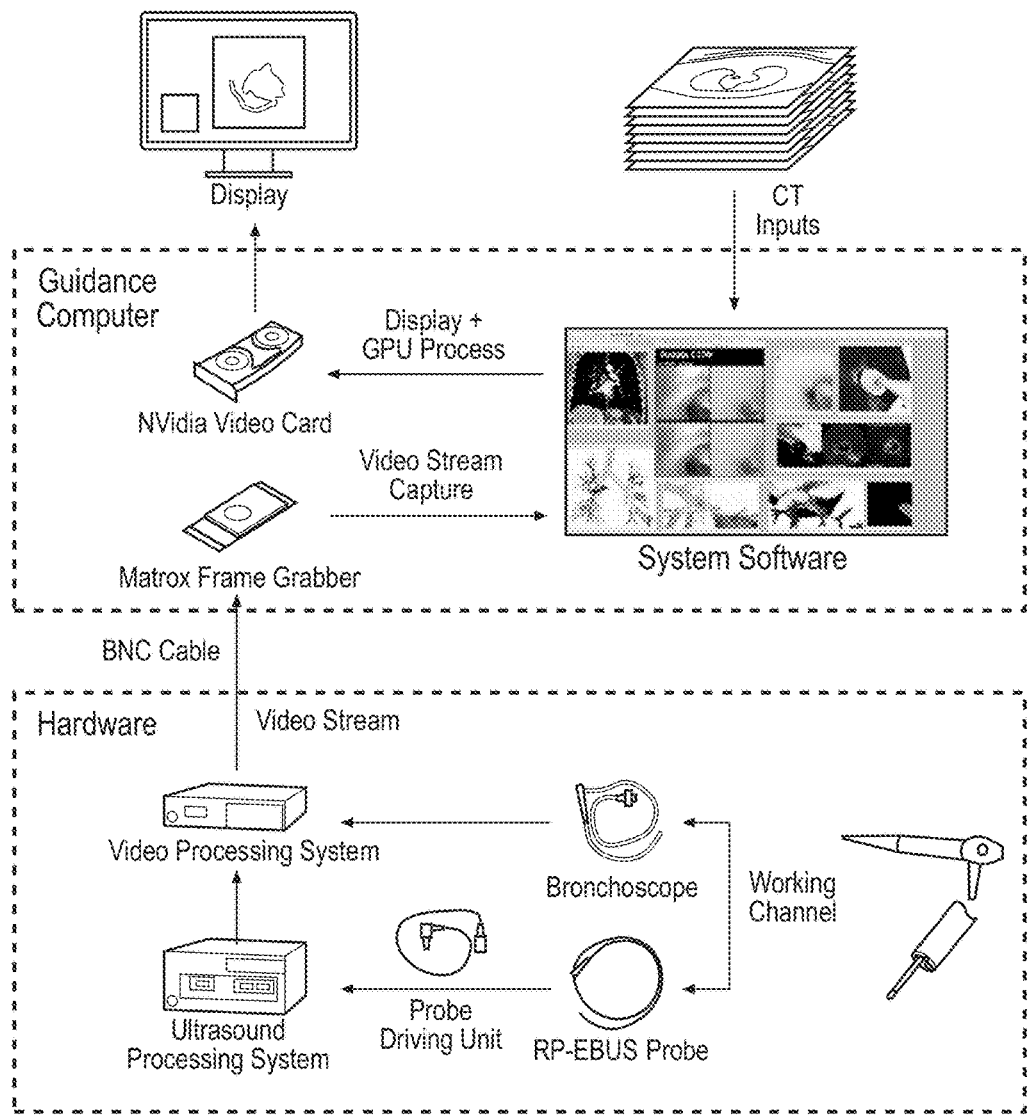
FIG. 16 shows system hardware.

In particular, the system was developed in C++ using Microsoft Visual Studio 2015. We developed and tested the system on a Dell Precision 7920 tower (64-bit Windows 10, 64 GB RAM, Intel Xeon Gold 6138 20-core 2.0 GHz), including an NVIDIA RTX 2080 Ti graphics card and a Matrox ClarityUHD frame grabber, as shown in FIG. 16. The software utilizes several external libraries including VTK, Qt, and OpenCV. Other details on the hardware used to conduct all tests appear in Section 3.E, Section 3.D give additional software details and our use of CUDA and the GPU, while gives exhaustive detail.

FIG. 16 presents the video and ultrasound configuration for the system. The guidance computer collects the video in real-time through a Matrox frame grabber. We use a multi-modal channel configuration; the ultrasound processing system is connected to the video processing system instead of the Matrox frame grabber directly. This configuration enables the system to grab multimodal imaging frames from a single input channel at 30 frames/second sampling rate. This channel integrates two video sources in a picture-in-picture form, videobronchoscopy and EBUS, into one screen. Only one of these two sources is presented in high resolution at any given time. The videobronchoscope and RP-EBUS probe are connected to their corresponding processors within the bronchoscopy suite.

The guidance protocol, which builds on our existing image-guided bronchoscopy platform [24, 30, 39, 67], involves a considerable amount of new software development. During the live procedure, the system display presents a series of graphical tools to assist with guidance, as partially described in Section 2 and illustrated by FIGS. 3-5. We now give a complete introduction to the wide range of available tools available. We use the phantom human case 20349.3.48 (ROI 11) as the illustrative example case to follow throughout this discussion. For case 20349.3.48, the dimensions of the Siemens CT scan are 512×512×373 with resolutions of $\Delta X = \Delta Y = 0.709$ mm, and $\Delta Z = 0.8$ mm. This target ROI is near the left inferior lobar bronchi and has a volume of 324.08 mm$^3$.

Figure 17A:
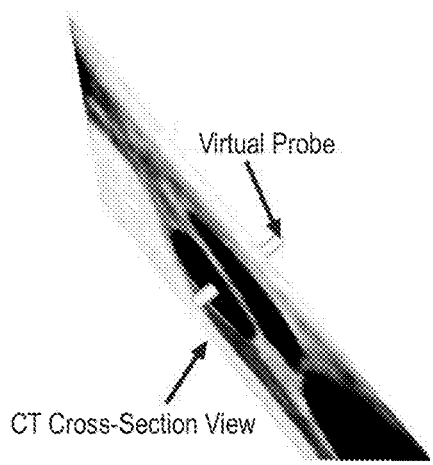
FIG. 17A shows virtual RP-EBUS probe model visualization; (virtual RP-EBUS probe model showing CT section view)
Figure 17B:
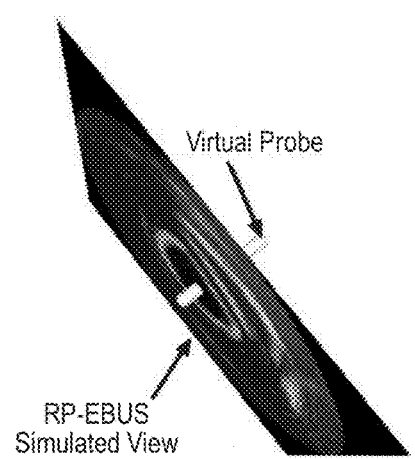
FIG. 17B shows virtual RP-EBUS probe model showing CT-based EBUS simulated view.

Because all the associated system tools are related to a proposed virtual RP-EBUS probe model, we start by introducing this model. This virtual RP-EBUS probe model consists of two parts, shown in FIGS. 17A and 17B:

1. A virtual probe, modeled by a rigid cylinder mesh model with round caps.
2. A 2D cross-section view, modeled by a 2D cross-section plane orthogonal to the virtual probe.

For the present system, we assume the use of an Olympus UM-S20-17S RP-EBUS probe. The virtual probe mimics a real RP-EBUS probe extending from a bronchoscope's working channel. The 2D cross-section view is a CT-based digital image array giving a simulated 360° radial circular view "observed" by the virtual RP-EBUS probe. It models the RP-EBUS video and its scan region at the virtual probe's current position in 3D CT chest space. It is designed to show either the current CT section or the CT-based EBUS simulated view. The form of the virtual RP-EBUS probe and its relation to the real RP-EBUS frame is exemplified by FIGS. 17A and 17B.

Rendered with other visualization tools, the virtual RP-EBUS probe model can mimic a real RP-EBUS probe and allow RP-EBUS integrated visualization and planning in the image-guided bronchoscopy system. Also, the virtual RP-EBUS model allows synchronization of the real RP-EBUS probe and videos to the 3D CT chest space during bronchoscopy. During live guidance, the present system registers the virtual probe to the real probe in the bronchoscopic video.

We incorporate this virtual RP-EBUS probe model into the existing VB and 3D surface visualizations to add RP-EBUS cues into our system (FIGS. 21A, 21B and 23-25). The virtual probe and its 2D cross-section view are rendered together with the 3D airway tree to provide a global view of the probe in the virtual chest space. We also render the virtual probe in VB views, which resembles the probe view observed in a real bronchoscopic video, shown in FIGS. 19A, 19B, 20A, 20B. This probe view in VB allows us to perform a probe registration using bronchoscopic video during guidance. In addition, we have incorporated reach capacity information into the visualization and rendered the airway tree with different colors, which indicates whether the current airway diameter can accommodate the scope, shown in FIGS. 21A, 21B, 25A and 25B.

The remainder of this section summarizes all of the visualization tools we designed for the system. These tools fall into two sets: a) tools modified from pre-existing tools; and b) all new tools. A reference manual gives complete details on these tools.

Figure 18:
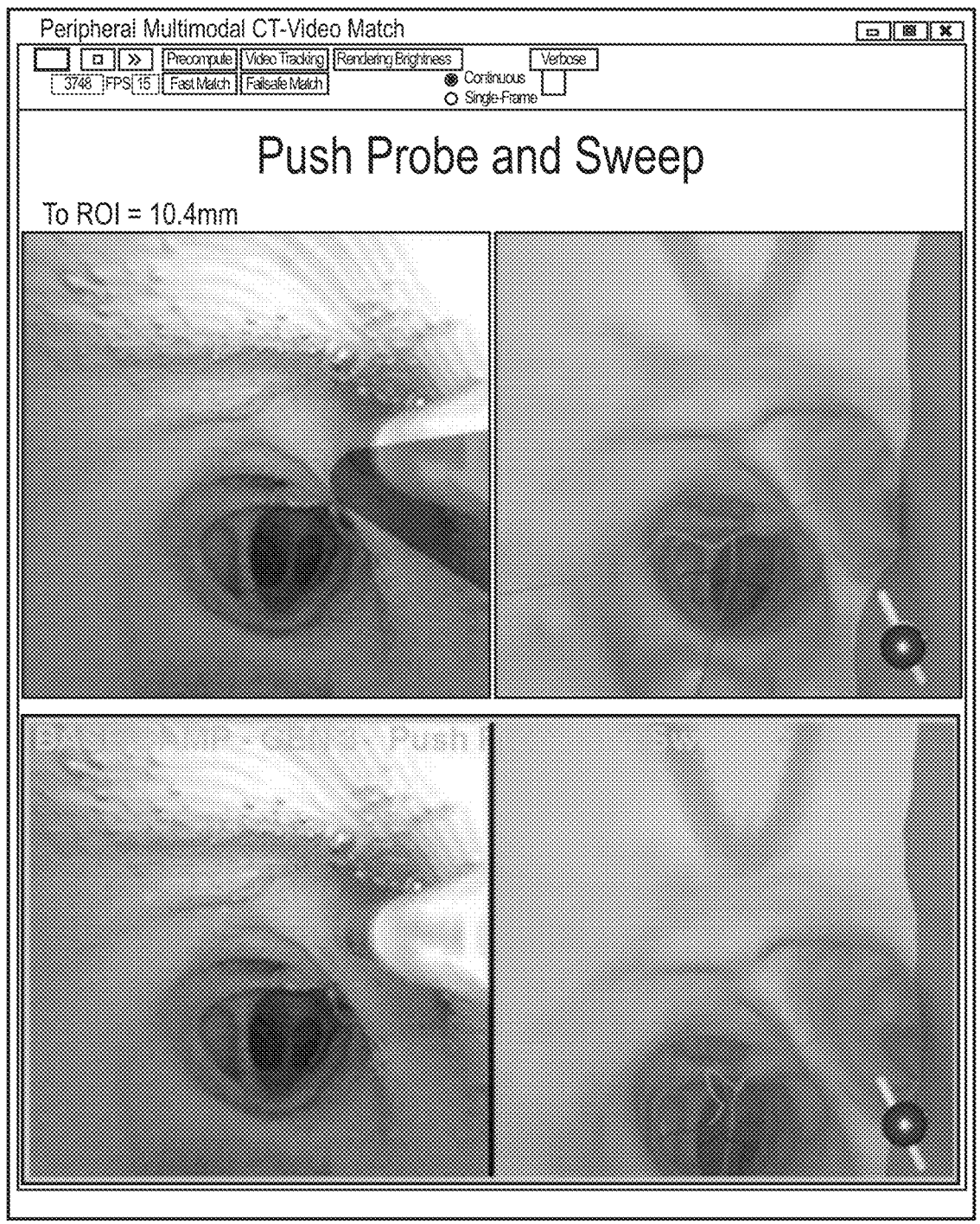
FIG. 18 shows a Peripheral Multimodal CT-Video Match example for case 20349.3.48 ROI 11; (The left side displays the bronchoscopic video. The right side shows the VB view rendered from the CT data and camera calibration parameters. The virtual RP-EBUS probe appears as a blue transparent round end cylinder on top of the bronchoscopic video. The lower section of the tool displays the frozen real bronchoscopy and VB views at the last location)
Figure 19A:
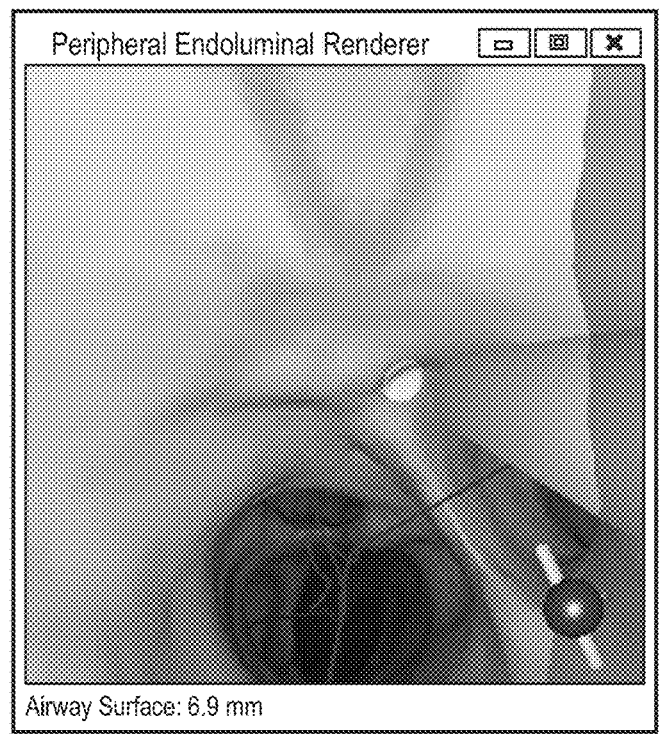
FIG. 19A shows the Peripheral Endoluminal Renderer example for case 20349.3.48 ROI 11; (This viewer contains all visual cues, ROI depth of samples (green), and regular VB view obstacles (red). Also, the virtual RP-EBUS probe is rendered as a gray round end cylinder from the right side of the VB view. The tool can also cast an indicator light from the virtual probe's tip and highlight the airway surface location it is pointing to)
Figure 19B:
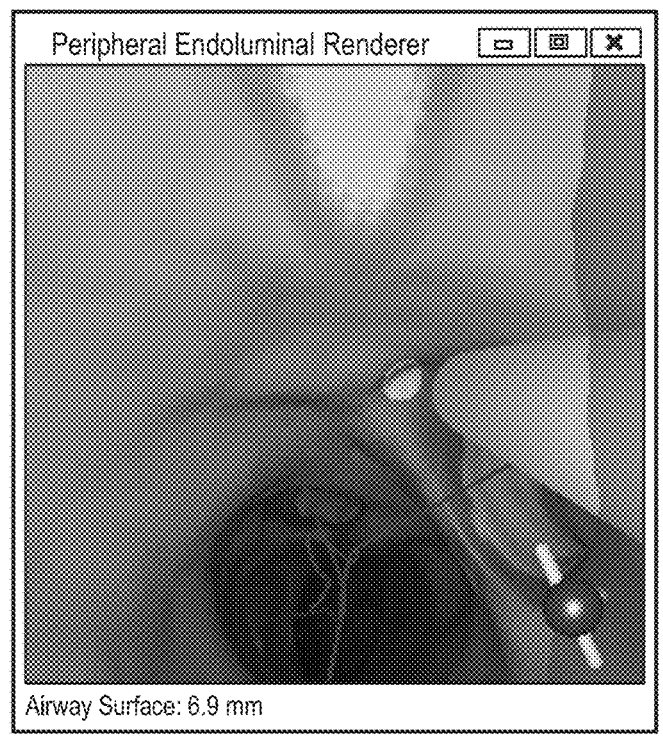
FIG. 19B shows the tool of FIG. 19A in reach capacity mode; ("Yellow" color for the next bronchi at 2 o'clock behind the virtual probe indicates it will tight fit the current 4.9 mm bronchoscope)
Figure 20A:
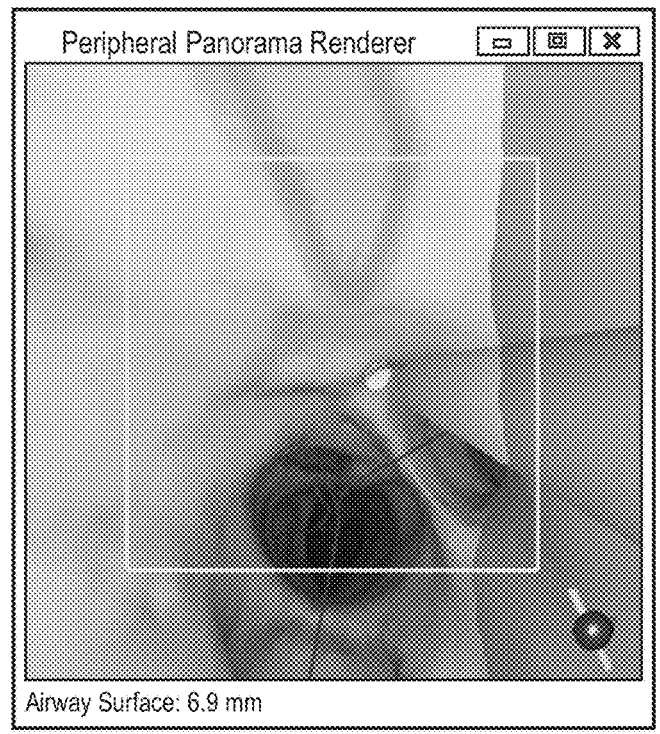
FIG. 20A shows the Peripheral Panorama Renderer example for case 20349.3.48 ROI 11; (The yellow rectangle represents the virtual camera's FOV in a regular VB viewer, corresponding to the view in Peripheral Endoluminal Renderer in FIG. 19. On each side of the rectangle, the expanded view shows a 25% larger view beyond the virtual camera's FOV. This allows this tool to show beyond the actual camera view to better show RP-EBUS probe location, target ROI, and obstacles)
Figure 20B:
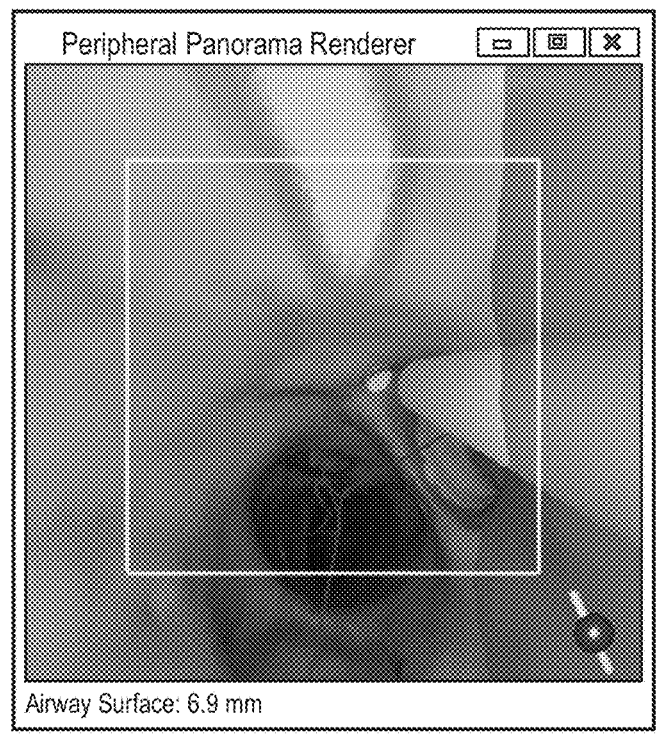
FIG. 20B shows the tool of FIG. 20A in reach capacity mode; ("Yellow" color for the next bronchi at 2 o'clock behind the virtual probe indicates it will tight fit the current 4.9 mm bronchoscope)
Figure 21A:
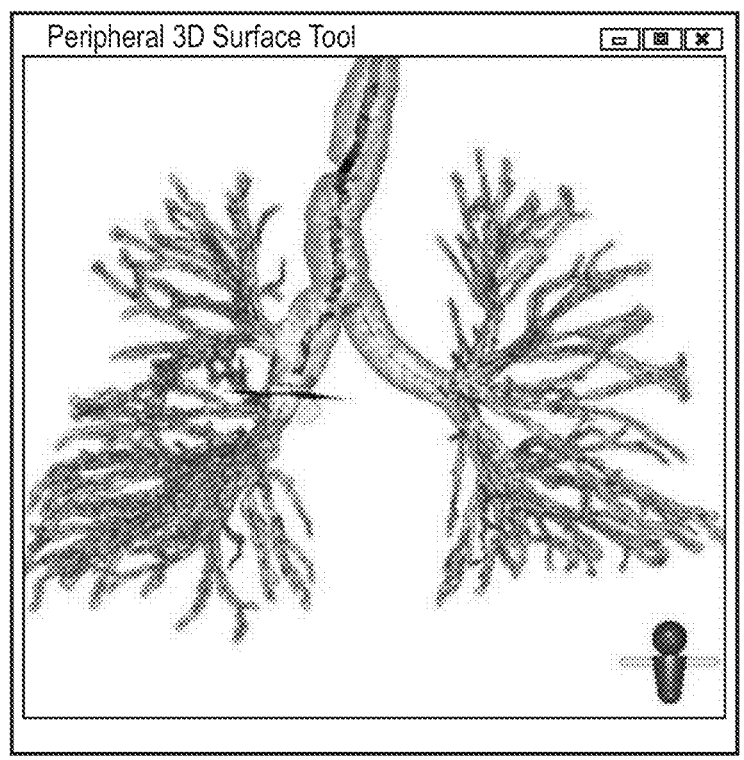
FIG. 21A shows the Peripheral 3D Surface Tool example for case 20349.3.48 ROI 11; (The blue route displays the pre-planned optimal route to the target ROI (blue). The yellow marker shows the current location of the VB camera. The gray round end cylinder shows the current virtual RP-EBUS probe location in 3D chest space. The 2D plane represents the corresponding scanning region of the virtual RP-EBUS probe at the current location.
Figure 21B:
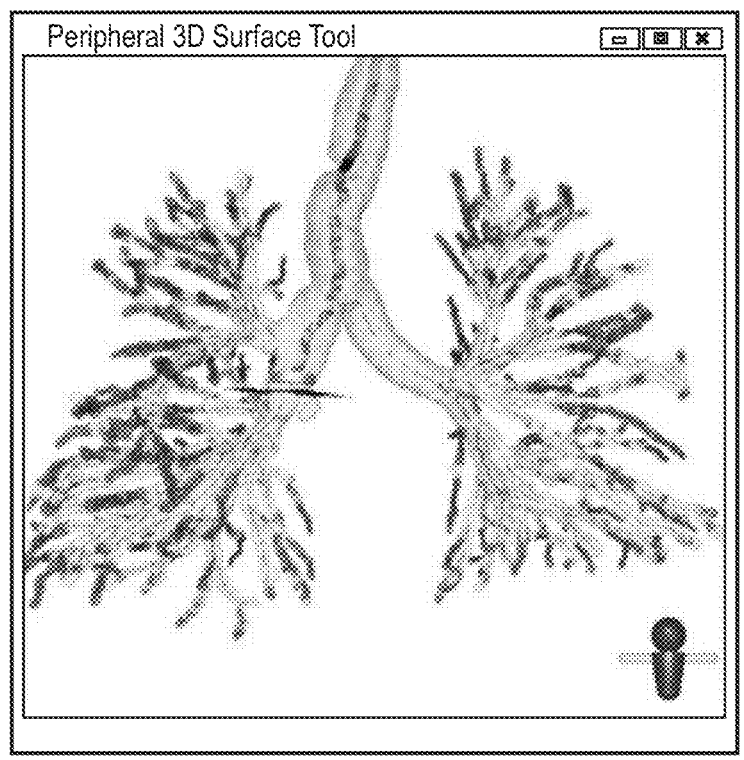
FIG. 21B shows the 3D surface rendering of the example in FIG. 21A under Cornish's reach capacity.

We first describe those tools derived from existing tools. These tools are designed for image-guided bronchoscopy drawing on three modalities: 3D chest CT, bronchoscopic video, and RP-EBUS video. To enable RP-EBUS-guided bronchoscopy, we added new RP-EBUS elements into these tools as follows:

Peripheral Multimodal CT-Video Match: This tool acts as the master tool during the image-guided bronchoscopy. During the procedure, most of the commands are invoked from this tool during live guidance. This tool shows bronchoscopic video and rendered images of the CT data and is designed to locate the video frame's viewpoint regarding the CT coordinate system. We also use this tool during the bronchoscopy to perform the RP-EBUS probe pose registration after the bronchoscope pose is registered. The tool also includes some useful controls to change bronchoscopic video and RP-EBUS video modes and is the core tool during image-guided bronchoscopy, shown in FIG. 18.

Peripheral Endoluminal Renderer: This viewer renders the airway surface VB view inside the airway and uses the same extracted surface as the Peripheral Multimodal CT-Video Match. In addition, unlike the VB view in the Peripheral Multimodal CT-Video Match, the VB is rendered with the new modern OpenGL pipelines and shaders. The modern OpenGL implementation empowered the existing VB view with a few new features, including the mesh model-based probe rendering, the light indicator from the virtual RP-EBUS probe tip, and the visualization of bronchoscope reach capacity, shown in FIGS. 19A and 19B.

Peripheral Panorama Renderer: This viewer renders an expanded VB view from the virtual camera's FOV. The expanded VB view allows better visualization of the virtual RP-EBUS probe's location, target ROI, and obstacles. This viewer uses the same modern OpenGL implementation in the Peripheral Endoluminal Renderer and allows advanced visualizations of the virtual RP-EBUS probe and the bronchoscope's reach capacity, shown in FIGS. 20A and 20B. The viewer displays the expanded view shows a 25% larger view beyond the virtual camera's FOV and a virtual RP-EBUS probe from the right side of the VB view.

Peripheral 3D Surface Tool: This tool shows a global exterior 3D rendering of the airway tree, pre-defined ROIs, and the pre-computed optimal airway routes. This tool is also rendered with the new modern OpenGL pipelines and shaders. The virtual RP-EBUS probe and its associated scanning region are also displayed during the image-guided bronchoscopy, shown in FIGS. 21A and 21B. The 2D scanning region can display either the corresponding 2D CT view or the CT-based RP-EBUS simulation view. In addition, this tool can render the 3D PET volume together with the global 3D rendering of the airway tree when PET data is loaded in the VNS.

Figure 22:
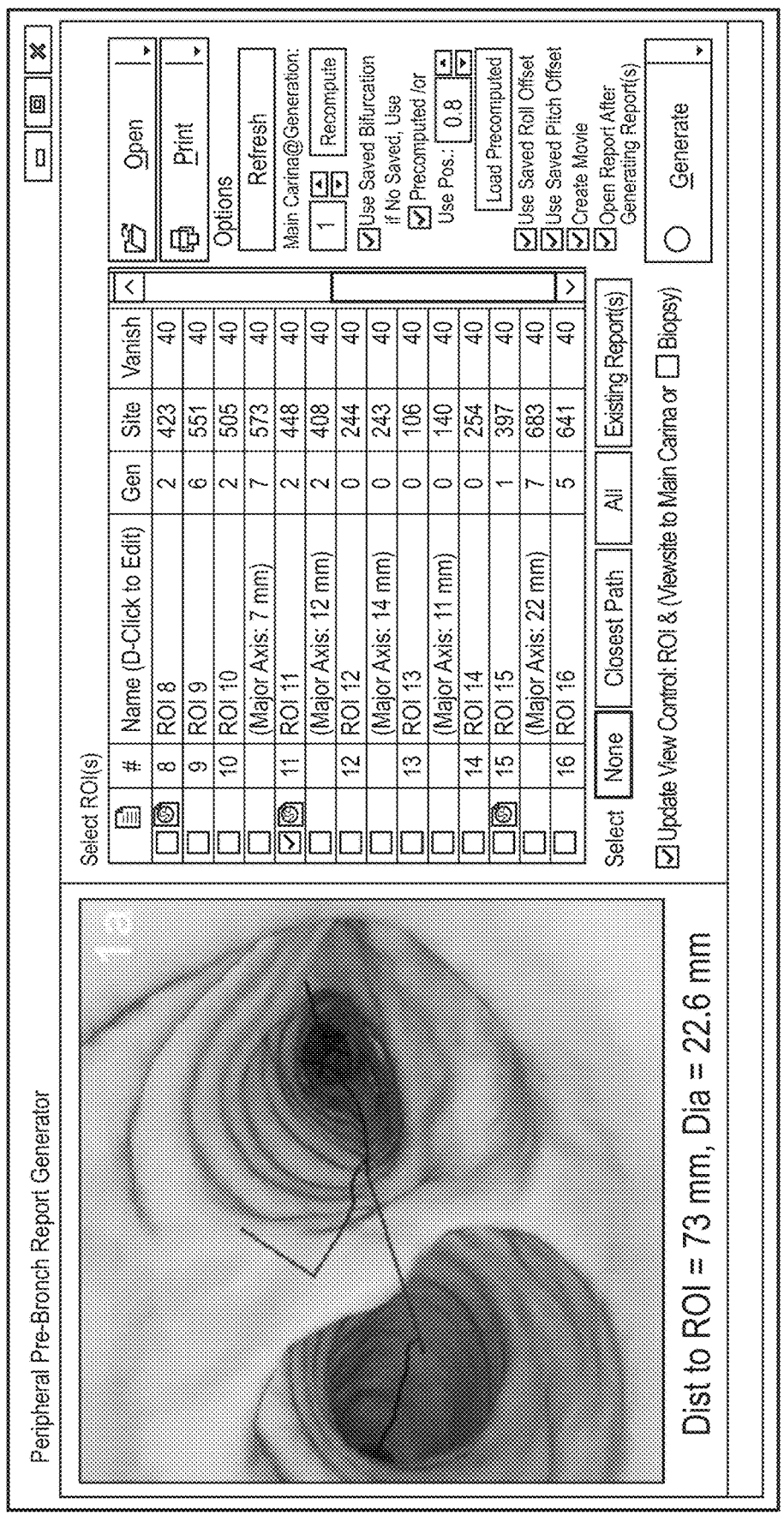
FIG. 22 shows the Peripheral Pre-Bronch Report Generator for case 20349.3.48 ROI 11; (This tool has the new modern OpenGL implementation of VB rendering. It can display a virtual RP-EBUS probe, a light indicator from the probe tip, and visualization of bronchoscope reach capacity information. This tool also added a Pitch angle offset control for the "Flex" maneuver of the bronchoscope)
Figure 23:
FIG. 23 shows the PeriBronchus Renderer—Forward example for case 20349.3.48 ROI 11; (This tool displays a VB view and its surrounding airway structure scanned by the virtual RP-EBUS probe. The yellow rectangle represents the virtual camera's FOV in a regular VB viewer as the Peripheral Endoluminal Renderer (FIG. 10). The gray round end cylinder shows the current virtual RP-EBUS probe location relative to the virtual bronchoscope camera. The 2D plane visualizes the corresponding scanning region view of the virtual RP-EBUS probe in CT or CT-based RP-EBUS simulation)
Figure 24:
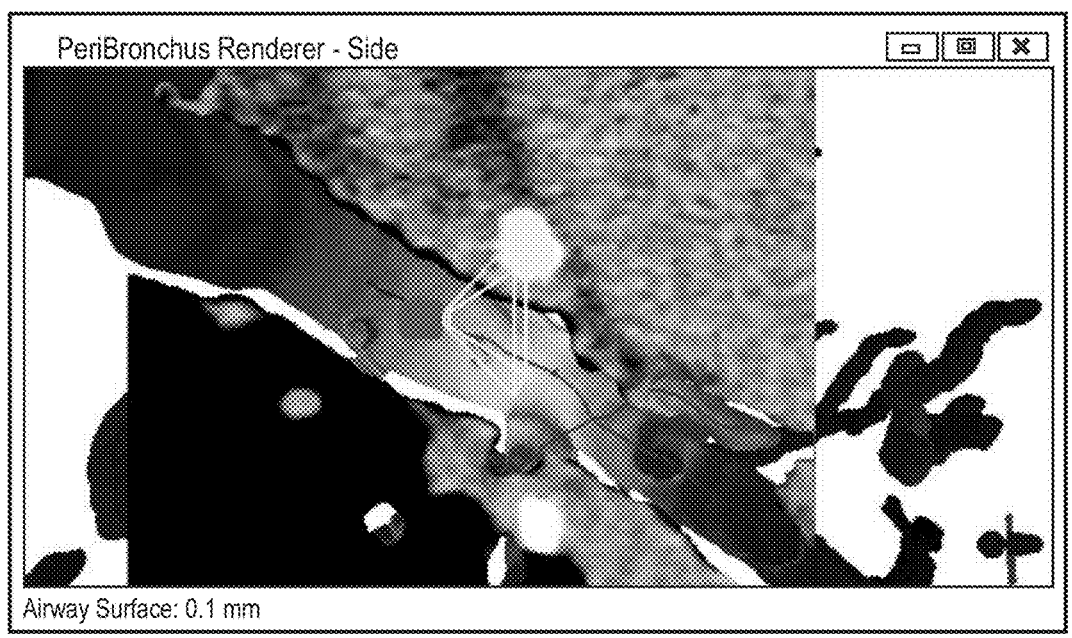
FIG. 24 shows the PeriBronchus Renderer—Side example for case 20349.3.48 ROI 11; (This tool visualizes the intraluminal VB and extraluminal airway structures from a side camera view. The yellow rectangles outline the actual virtual camera's FOV at the current location. The black cylinder represents the virtual bronchoscope and its current position within the airway. The gray round end cylinder represents the current virtual RP-EBUS probe's location relative to the virtual camera FOV. The 2D plane is parallel to the longitudinal axis of the current VB camera location and shows the surrounding CT airway structures along the longitudinal axis)

Peripheral Pre-Bronch Report Generator: This tool generates a pre-bronchoscopy report presenting relevant visual and quantitative data along the pre-computed optimal route. The previews consist of virtual bronchoscopic endoluminal renderings at bifurcations encountered along the route, renderings of the airway tree and ROI at the suggested biopsy location, and three-dimensional cues as to the location for the biopsy. This tool also replaced the legacy OpenGL-based visualization with the new modern OpenGL implementation. It improved a few visualizations for RP-EBUS, including the mesh model-based probe rendering, the light indicator from the virtual RP-EBUS probe tip, and the visualization of bronchoscope reach capacity, shown in FIG. 22. We use this tool to generate a pre-bronchoscopy report during procedure planning.

We next introduce the collection of new tools developed for RP-EBUS-guided bronchoscopy:

PeriBronchus Renderer—Forward: This tool is a novel visualization tool to enable advanced simultaneous visualization of intraluminal VB view and extraluminal airway structures from a forward camera. The VB view can display the interior airway structures but lacks the extra information surrounding the airways. RP-EBUS enables excellent visualization of the bronchial wall and surrounding airway structures [21]. As presented in FIG. 23, this tool enables a forward camera view of the virtual RP-EBUS probe and its associated scanning region while keeping the current VB view at the current bronchoscope location. The scanning region can display either the corresponding 2D CT view or the CT-based RP-EBUS simulation view as the Peripheral 3D Surface Tool. This tool allows physicians to preview the expected RP-EBUS scans at the current airway location before RP-EBUS-guided bronchoscopy.

PeriBronchus Renderer—Side: This tool is a novel visualization to enable advanced simultaneous visualization of intraluminal VB view and extraluminal airway structures looking from a side camera. This tool is a side version of the Peribronchus Renderer—Forward and enables a different visualization of the current VB view and its surrounding airway structures. This tool displays the current VB camera FOV and the virtual RP-EBUS probe inside the VB airway. It visualizes the current VB camera and probe location at the current airway branch, shown in FIG. 24. Moreover, this tool shows a 2D plane parallel to the longitudinal axis of the current VB camera location and displays the CT airway structures along the longitudinal axis. This tool can provide excellent views for RP-EBUS-based procedure planning preview and live image-guided bronchoscopy.

Figure 25A:
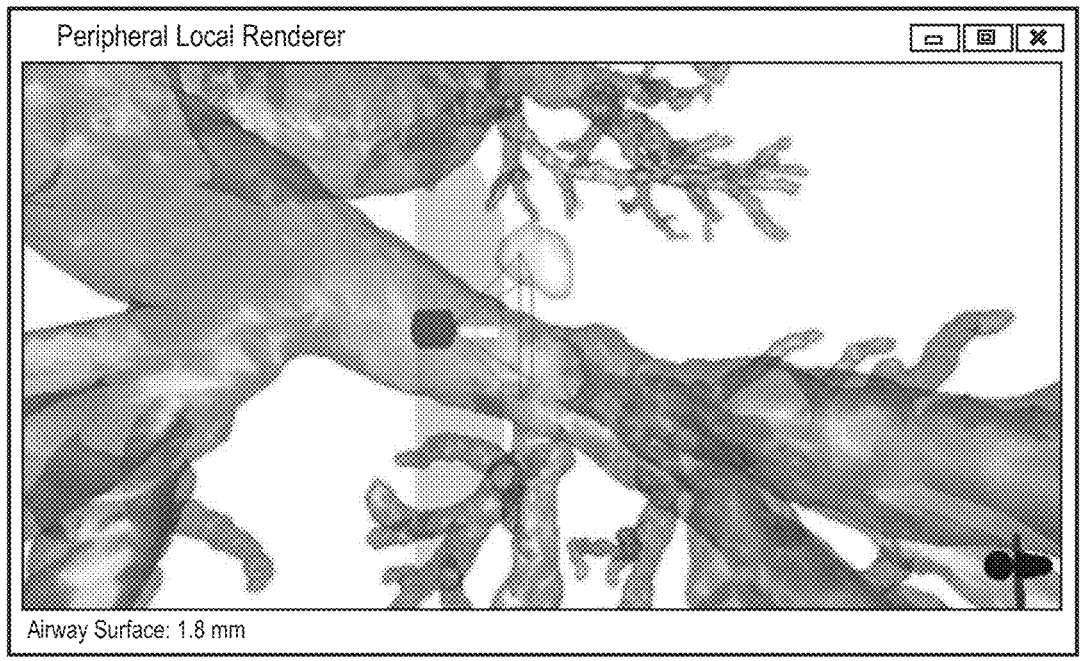
FIG. 25A shows a Peripheral Local Renderer example for case 20349.3.48 ROI 11; (The black cylinder represents the virtual bronchoscope and its current position within the airway. The magenta rectangles depict the corresponding FOV of the virtual bronchoscope. The white round end cylinder shows the current virtual RP-EBUS probe relative to the virtual bronchoscope. The gray transparent plane presents the corresponding scanning region view of the virtual RP-EBUS probe at the current location. The airway tree (gold) and ROI (Magenta) in FIG. 25A depicts the 3D local anatomical structures surrounding the virtual devices (virtual bronchoscope and virtual RP-EUBS probe)
Figure 25B:
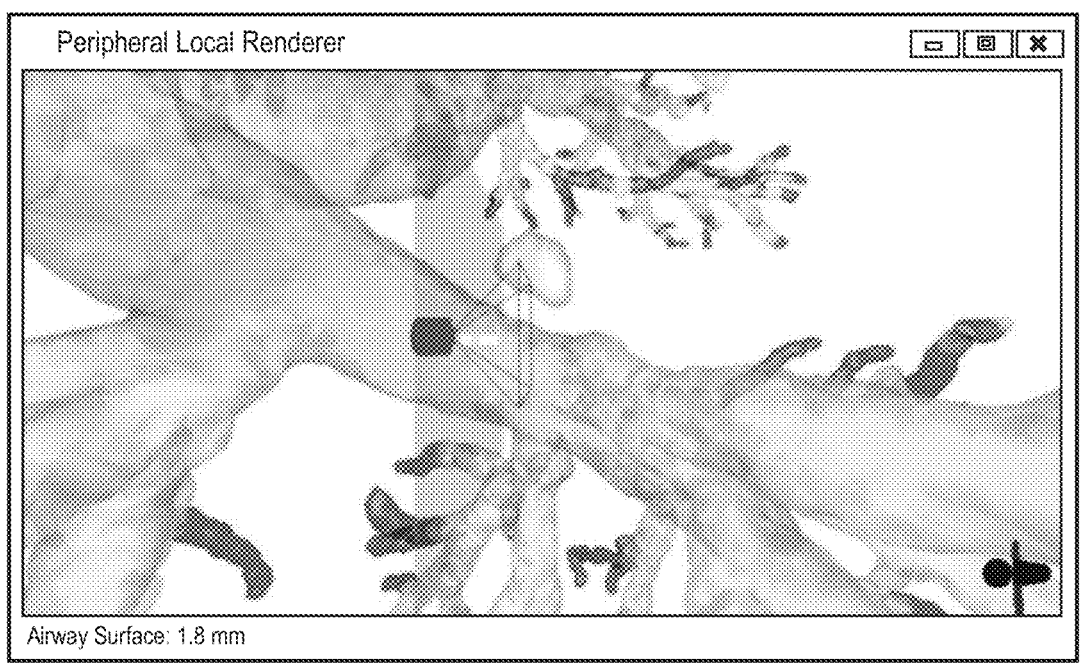
FIG. 25B shows the airway of the example in FIG. 25B with Cornish's reach capacity.

Peripheral Local Renderer: This tool offers the side view showing the virtual bronchoscope and its FOV, virtual RP-EBUS probe and its scanning region, target ROI, and 3D surface at the local area. While the virtual bronchoscope moves toward the target ROI, this tool will provide visual cues for the relative positions between the target ROI and virtual devices (virtual bronchoscope and virtual RP-EUBS probe). As shown in FIGS. 25A and 25B, the Local Renderer can visualize the virtual bronchoscope and RP-EBUS probe and the surrounding airway surface and ROI.

Figure 26:
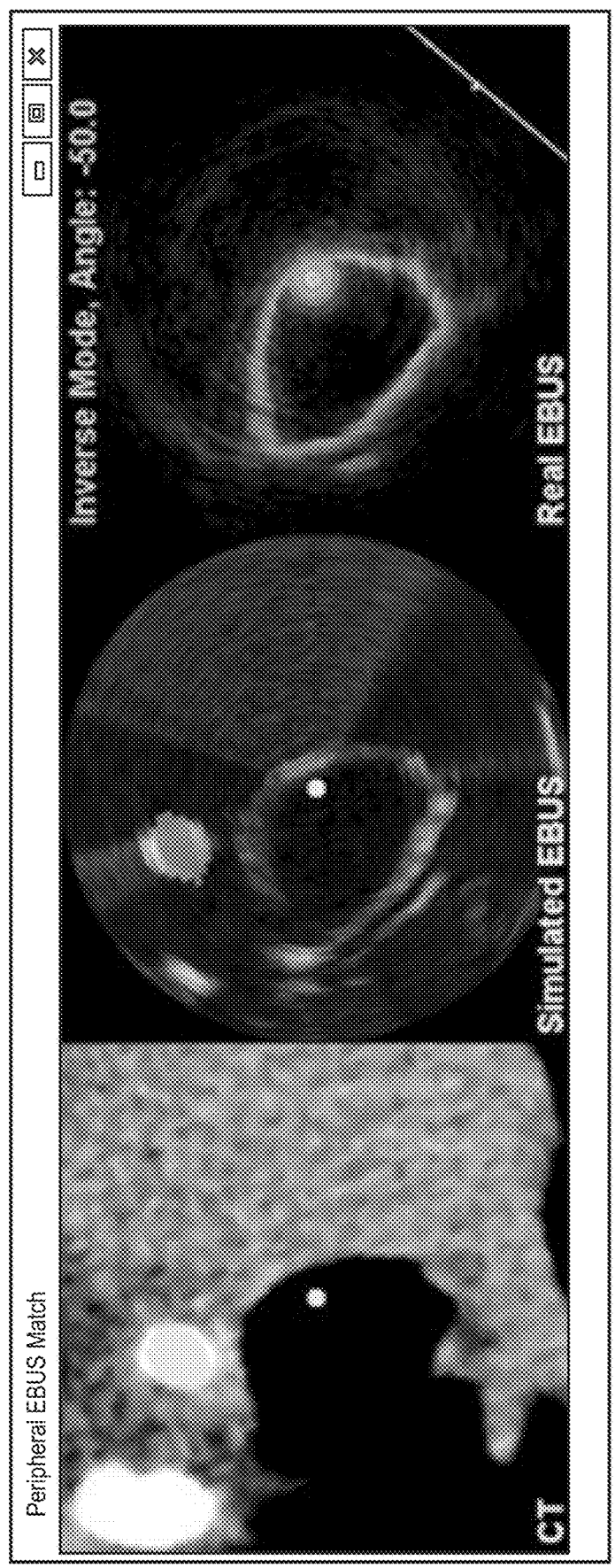
FIG. 26 shows a Peripheral EBUS Match example for case 20349.3.48 ROI 11; (The left view shows the CT section view corresponding to the associated scanning region of the virtual RP-EBUS probe. The middle view shows the RP-EBUS simulation from the CT section view. The right view shows the live RP-EBUS video frame after alignment)

Peripheral EBUS Match: This tool displays the CT section view, CT-based RP-EBUS simulated view, and live RP-EBUS video frame side-by-side. The CT section and CT-based RP-EBUS simulation correspond to the associated scanning region of the virtual RP-EBUS probe. As shown in FIG. 26, this tool can also blend the target ROI intersection region on the CT and simulation views. In addition, the tool displays the image display mode and direction offset information on the RP-EBUS video frame.

Figure 27A:
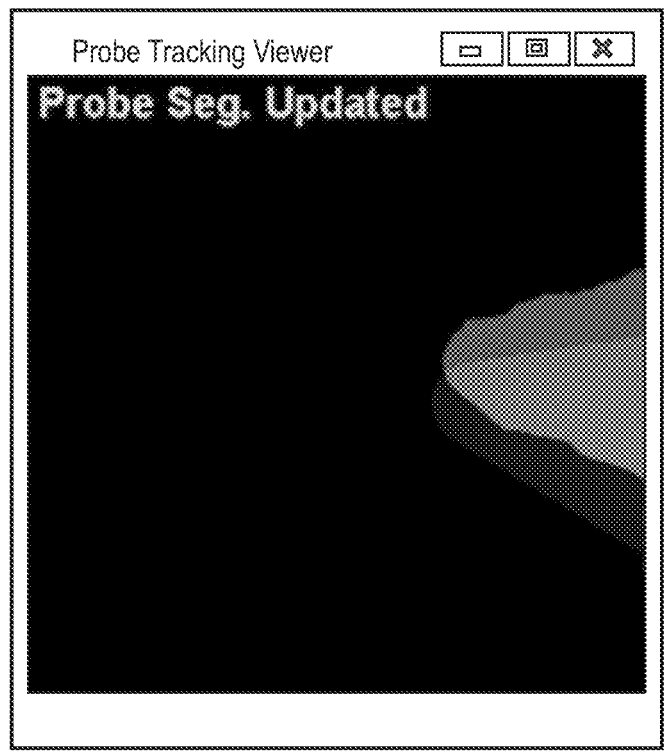
FIG. 27A shows the Probe Tracking Viewer example for case 20349.3.48 ROI 11.
Figure 27B:
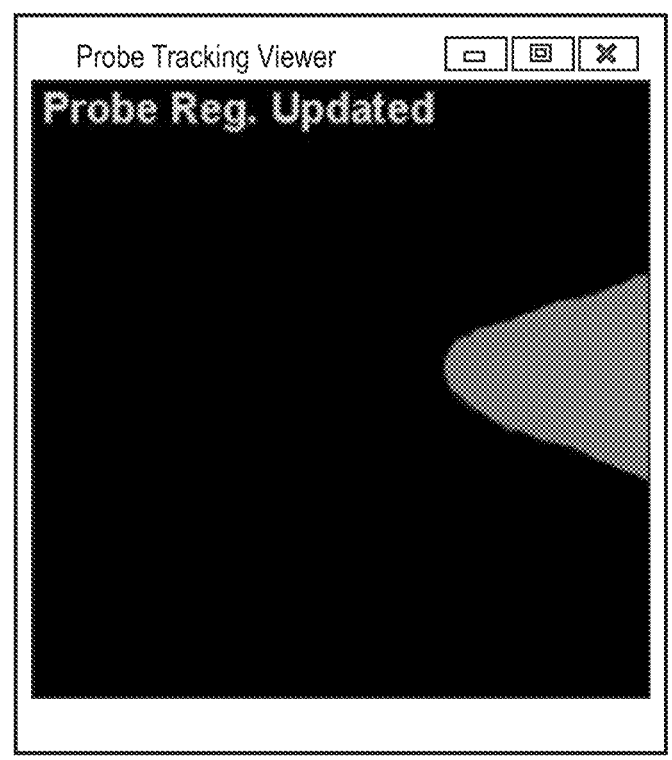
FIG. 27B shows the tool of FIG. 27A after RP-EBUS probe registration; (The blue and gray silhouettes are aligned to indicate a successful virtual to real RP-EBUS registration)
Figure 28A:
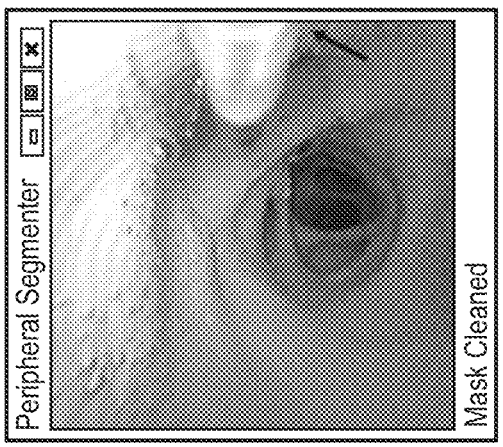
FIG. 28A shows a Peripheral Segmenter Interactive Drawing example for case 20349.3.48 ROI 11.
Figure 28B:
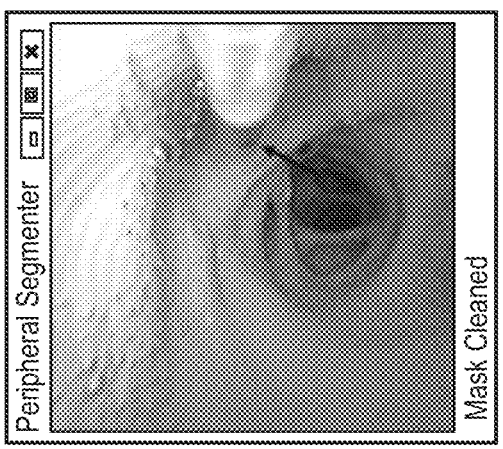
FIG. 28B shows that because the probe's body is mostly straight, choose the second point with mouse left click somewhere before the rounded end.
Figure 28C:
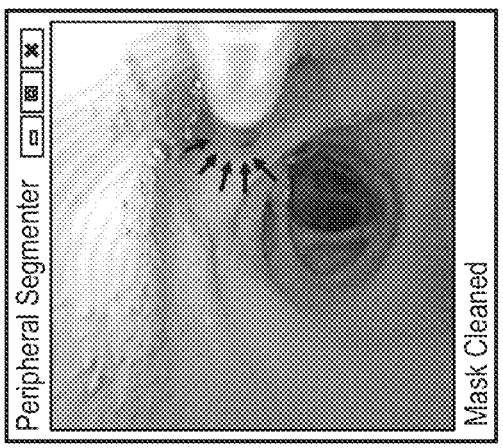
FIG. 28C shows that mouse left click to mark a few points around the probe's rounded end to make a few short line segments around the probe's distal end.
Figure 28D:
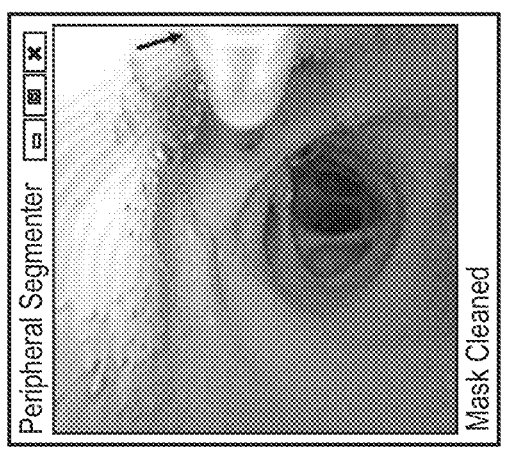
FIG. 28D shows that after the line segments pass the rounded end and reach the other side of the probe's body, like the first point, mouse right-click within 10 pixels from the boundary will automatically adhere the clicked point to the closest point on the border.
Figure 28E:
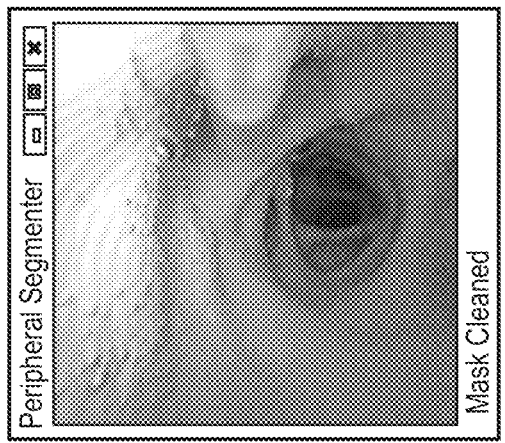
FIG. 28E shows that the mouse right-click will indicate the tool that the drawing is finished, and the tool will fill the mask with blue color.

Probe Tracking Viewer: This viewer shows the alignment of the real RP-EBUS segmentation mask and the virtual RP-EBUS probe during the RP-EBUS probe registration process. As shown in FIGS. 27A and 27B, the viewer displays the RP-EBUS segmentation mask for the bronchoscopic video frame either from TensorFlow-based semantic segmentation using the Deeplab v3 plus or the interactive segmentation using the Peripheral Segmenter below. The viewer also blends the virtual RP-EBUS probe on the segmentation mask at the current position of the virtual RP-EBUS probe to provide intuitive probe alignment visualization.

Peripheral Segmenter: This tool allows users to draw the real RP-EBUS probe mask on the selected bronchoscopic video frame. The tool uses mouse interactions to draw the probe segmentation mask and send the segmentation result to the system for RP-EBUS probe registration, shown in FIGS. 28A-28E. It offers a fail-safe method for obtaining the RP-EBUS probe mask from the bronchoscopic video when TensorFlow-based semantic segmentation is unavailable or unsatisfactory. The segmentation methods like live-wire and region growing cannot produce probe segmentation with even boundaries. Therefore, we chose the consecutive line drawing to label a probe segmentation quickly during the live bronchoscopy. An example of interactive probe segmentation is illustrated in FIGS. 28A-28E:

Starting from one side of the probe, mouse left click within 10 pixels from the boundary will automatically adhere the clicked point to the closest point on the border.

Because the probe's body is mostly straight, choose the second point with mouse left click somewhere before the rounded end.

Mouse left click to mark a few points around the probe's rounded end to make a few short line segments around the probe's distal end.

After the line segments pass the rounded end and reach the other side of the probe's body, like the first point, mouse right-click within 10 pixels from the boundary will automatically adhere the clicked point to the closest point on the border. The mouse right-click will indicate the tool that the drawing is finished, and the tool will fill the mask with blue color.

Figure 29A:
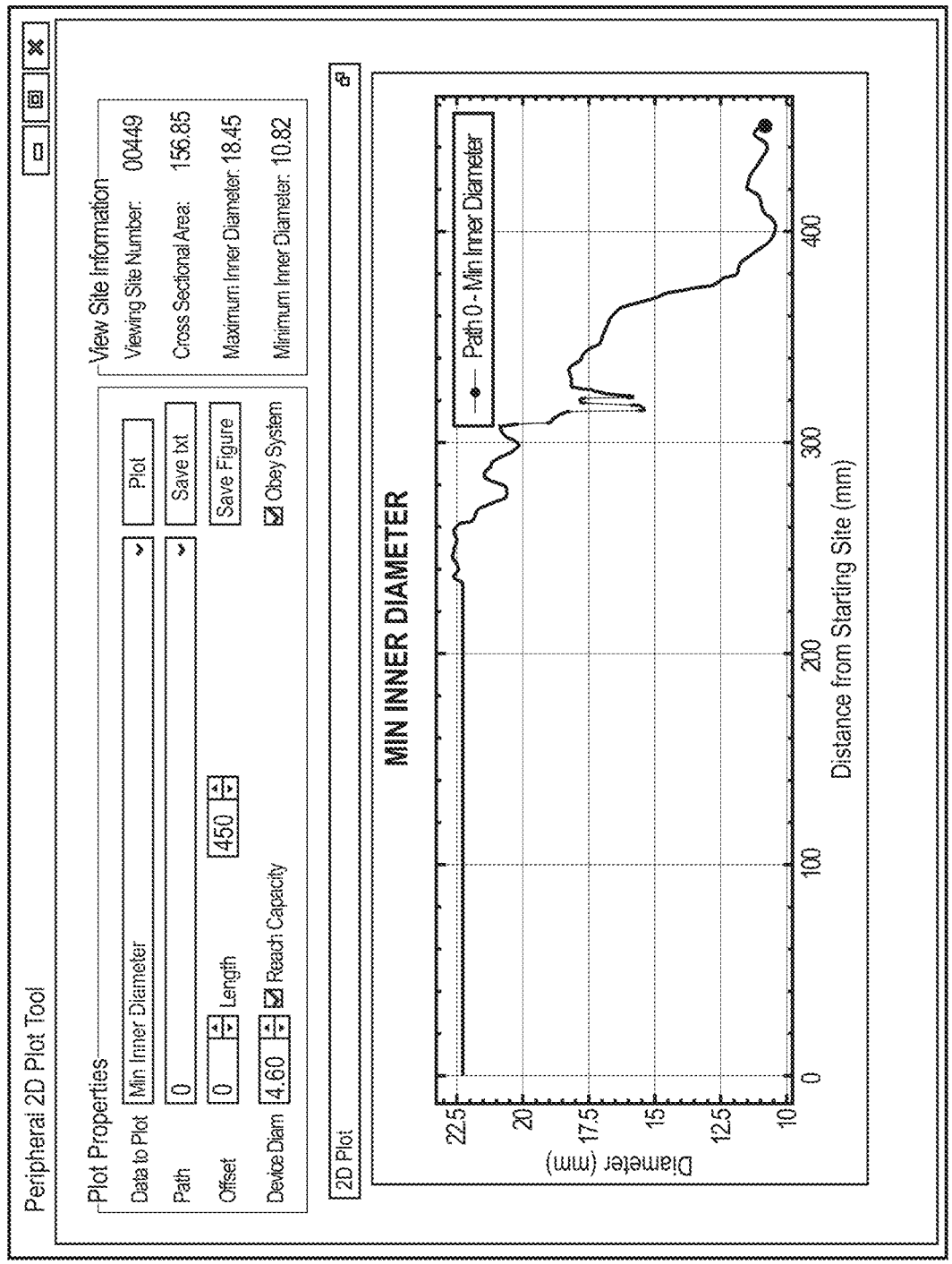
FIG. 29A shows the Peripheral 2D Plot Tool example for case 20349.3.48 ROI 11.
Figure 29B:
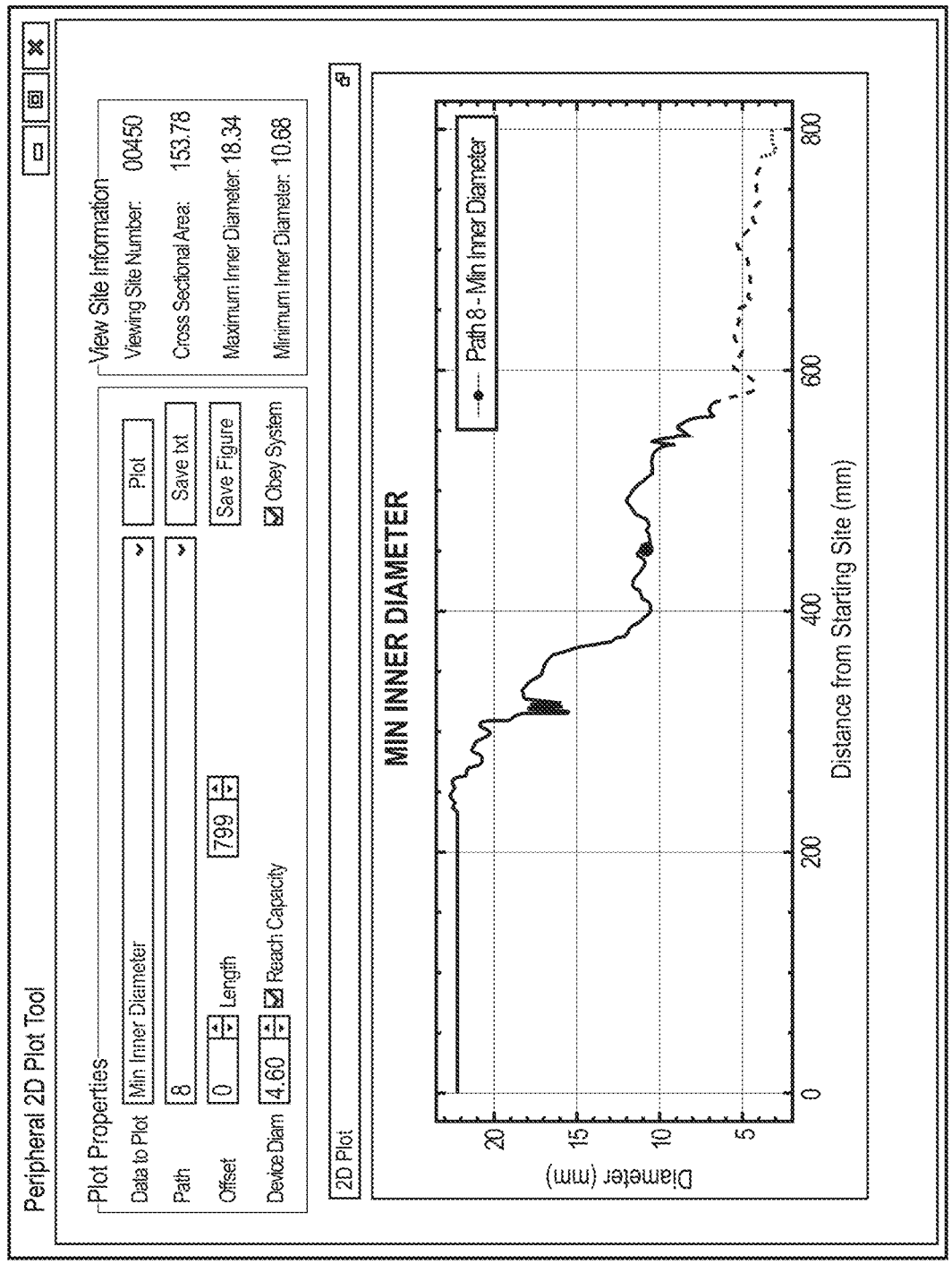
FIG. 29B shows Path 8 that contains the optimal route of ROI 11.

Peripheral 2D Plot Tool: This tool plots the quantitative measurements associated with an optimal route for the ROI. The available quantitative measurements are the cross-sectional area, minimum inner diameter, orthogonal to the minimum inner diameter, maximum inner diameter, minimum outer diameter, and maximum outer diameter. The tool can also visualize bronchoscope reach capacity with different colors in the plot, shown in FIGS. 29A and 29B. This tool provides an intuitive way to visualize the reach capacity and other quantitative measurements during the procedure planning.

Figure 30:
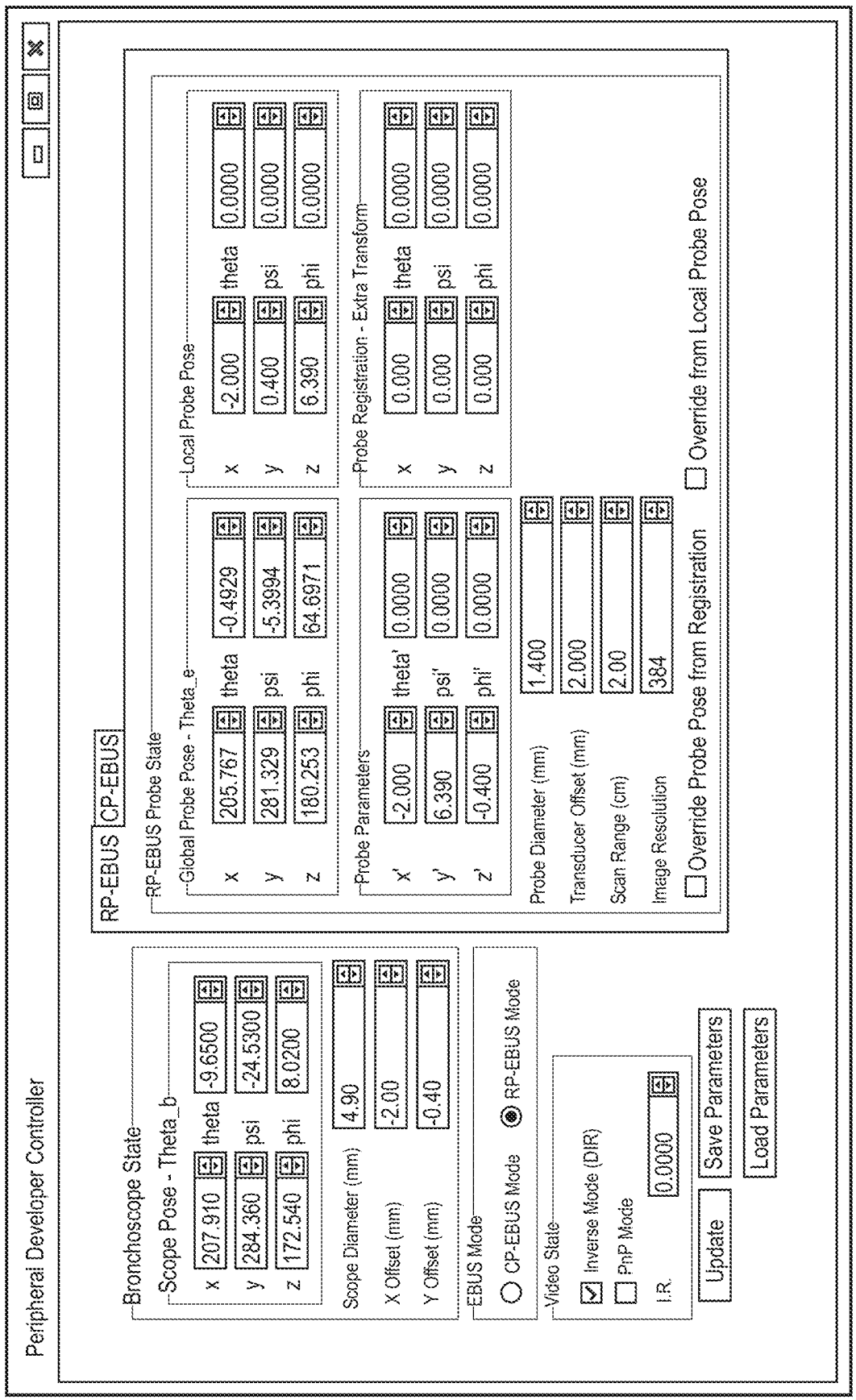
FIG. 30 shows the Peripheral Developer Controller example for case 20349.3.48 ROI 11; (The left part provides the bronchoscope-related information including the current VB pose, the bronchoscope diameter, distal end geometry, and image display controls. The right part provides the EBUS-related information, including the current virtual RP-EBUS global pose in 3D chest space, the local pose relative to the VB camera, and EBUS image display controls)
Figure 31A:
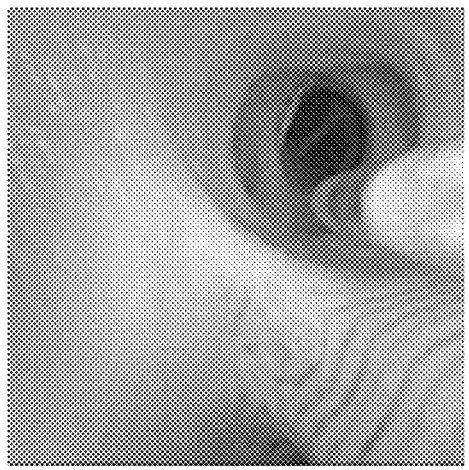
FIG. 31A shows a bronchoscopic video frame with visible RP-EBUS probe for two-phase RP-EBUS registration example for case 21405.3a ROI 2.
Figure 31B:
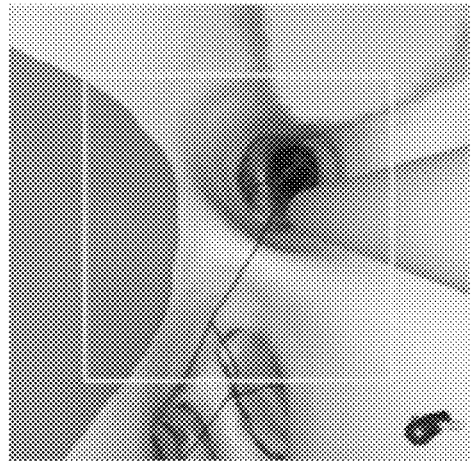
FIG. 31B shows a corresponding VB and virtual RP-EBUS probe for the example in FIG. 31A.
Figure 31C:
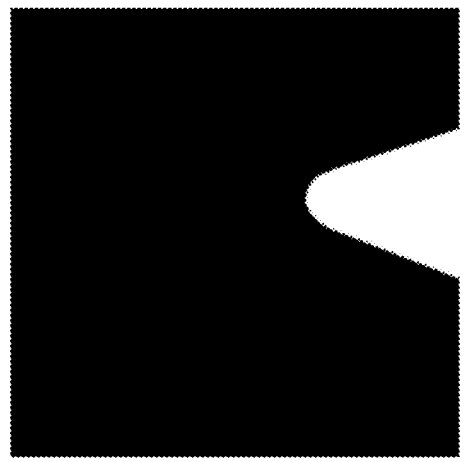
FIG. 31C shows ground truth segmentation for the example in FIG. 31A.
Figure 31D:
FIG. 31D shows the semantic segmentation result for the example in FIG. 31A.
Figure 31E:
FIG. 31E shows a CT cross-section view at the registered RP-EBUS probe pose, CT-based RP-EBUS video simulation, and real RP-EBUS video at a nearby location for the example in FIG. 31A.

Peripheral Developer Controller: This tool is a developer tool to display and control bronchoscope and RP-EBUS related parameters and functions. This tool is not displayed during the image-guided bronchoscopy but can provide developers with an overview of current VB and virtual RP-EBUS status, shown in FIG. 30.

In summary, we introduced the modern OpenGL pipeline and OpenGL Shading Language (GLSL) into VB and related tools, including:

1. A complete virtual RP-EBUS probe model and advanced light indicator in VB to show the current targeting airway point.
2. Novel PeriBronchus Renderer tools, which enable advanced simultaneous visualization of intraluminal VB view and extraluminal airway structures from a forward or side camera.
3. Introduced and modified Cornish reach capacity during airway tree visualization for both pre-operative procedure planning and intra-operative image-guided bronchoscopy [17].

5. Validation

We tested our methodology using lung-cancer patient data collected under an IRB-approved protocol and informed consent. CT scans were produced by either a Siemens Somatom, Siemens Sensation-40, or Canon Aquilion Prime CT scanner. Each scan consisted of a series of 512×512 axial-plane sections, where section thickness=0.75 mm, section spacing=0.5 mm, axial-plane resolution $\Delta x=\Delta y<1.0$ mm. Thus far, we have tested the system in retrospective human studies and in controlled live studies using phantoms and animals (porcine model). We have also performed initial live lung-cancer patient feasibility/safety studies [69].

FIGS. 31A-31E give an example of the complete guidance protocol and the two-phase registration method for a controlled human phantom study. The figure illustrates the results after all guidance to the ROI is completed and the RP-EBUS probe was invoked. As is clear, the correspondence between the virtual guidance model and real data is strong. Overall, for the tests done with this case and ROI, the overall probe pose registration error between the real object and the ground truth $e_p^{\Theta_e}=1.11$ mm, while the corresponding angular direction difference in the pose $e_d^{\Theta_e}=3.53°$. Also, for a series of ROIs tested for two human phantoms, we achieved the results of Table 1. Details of these tests and other successful other experiments appears in reference [69].

TABLE 1

Summary of the RP-EBUS registration results over 5 ROIs for two human phantom cases.

| | | Scope Registration | | RP-EBUS Probe Registration | | | Global Registration | |
|---|---|---|---|---|---|---|---|---|
| Cases | ROIs | $e_p^{\Theta_b}$(mm) | $e_d^{\Theta_b}$ (°) | Seg. IOU | $e_p^{\Theta_{cb}}$ (mm) | $e_d^{\Theta_{eb}}$ (°) | $e_p^{\Theta_e}$ (mm) | $e_d^{\Theta_e}$ (°) |
| 2 | 5 | 1.45 ± 0.68 [0.36, 2.81] | 3.09 ± 1.20 [0.22, 5.60] | 0.94 ± 0.02 [0.90, 0.98] | 0.38 ± 0.27 [0.08, 1.52] | 2.24 ± 1.03 [0.30, 5.03] | 1.94 ± 1.11 [0.45, 4.93] | 3.74 ± 1.49 [0.22, 6.94] |

Figure 32:
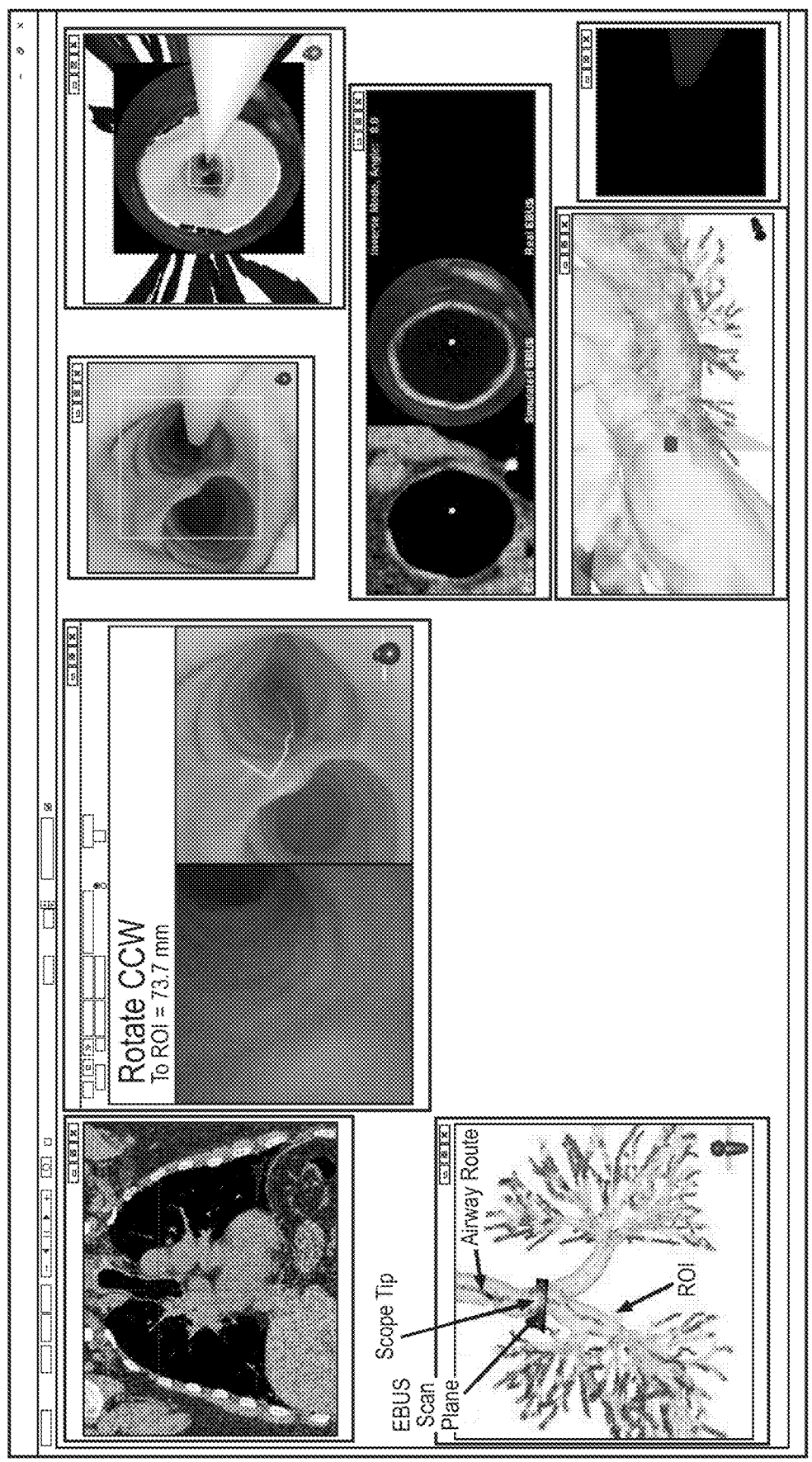
FIG. 32 shows the system at the initial state of the navigation phase during an image-guided bronchoscope; (The example is an ROI near the left inferior lobar bronchi from case 20349.3.48. The technician first initializes the system at the virtual trachea. The Peripheral 3D Surface Tool [bottom left] showed the target lesion (light blue) and the navigation route (dark blue). The can-shaped icon represents the scope tip and indicates the virtual bronchoscope's current position along the route. The Peripheral Multimodal CT-Video Match [top middle] depicts the endoluminal video view after distortion correction and the VB view (virtual "video" view))
Figure 33:
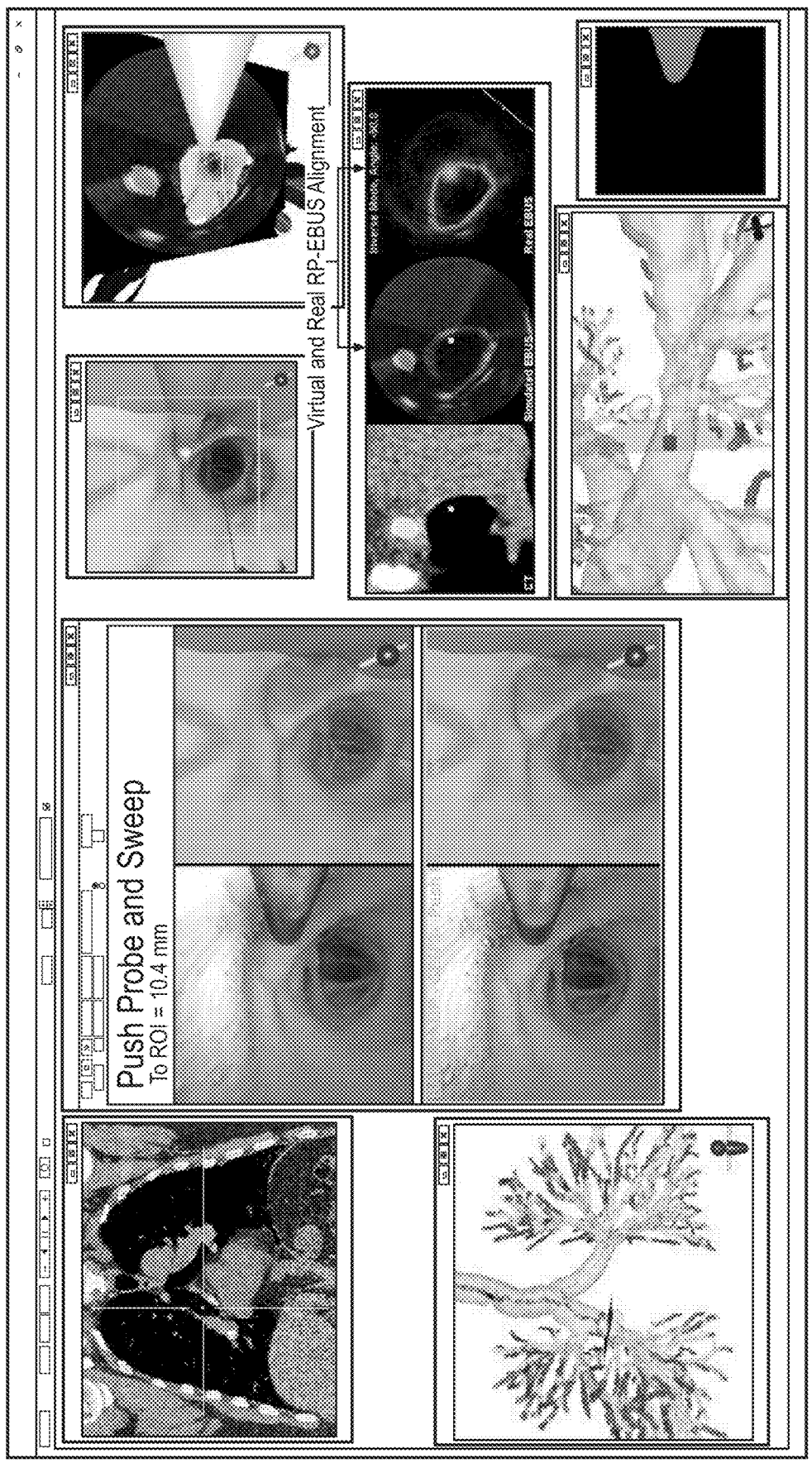
FIG. 33 shows the system shows current RP-EBUS video frame after the final alignment; (After the final virtual and real RP-EBUS view alignment, the physician has a known RP-EBUS probe pose before live ROI confirmation. The visualization tools in the system provide additional information for RP-EBUS invocation. The physician can expect to observe RP-EBUS findings resemble the "'Simulated EBUS' view in the Peripheral EBUS Match [center right])
Figure 34A:
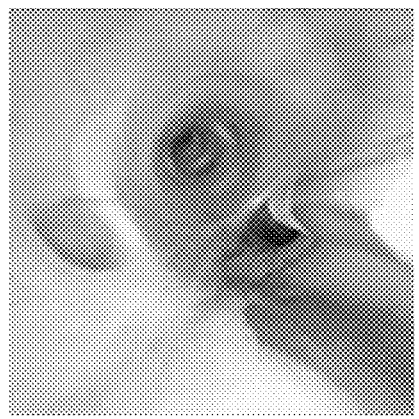
FIG. 34A shows a bronchoscopic video frame with visible RP-EBUS probe for two-phase RP-EBUS registration example for animal study PennVet Pig 2 ROI 4.
Figure 34B:
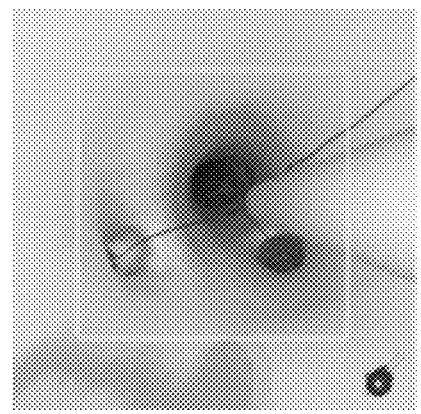
FIG. 34B shows a corresponding VB and virtual RP-EBUS probe for the example in FIG. 34A.
Figure 34C:
FIG. 34C shows a ground truth segmentation for the example in FIG. 34A.
Figure 34D:
FIG. 34D shows the semantic segmentation result for the example in FIG. 34A.
Figure 34E:
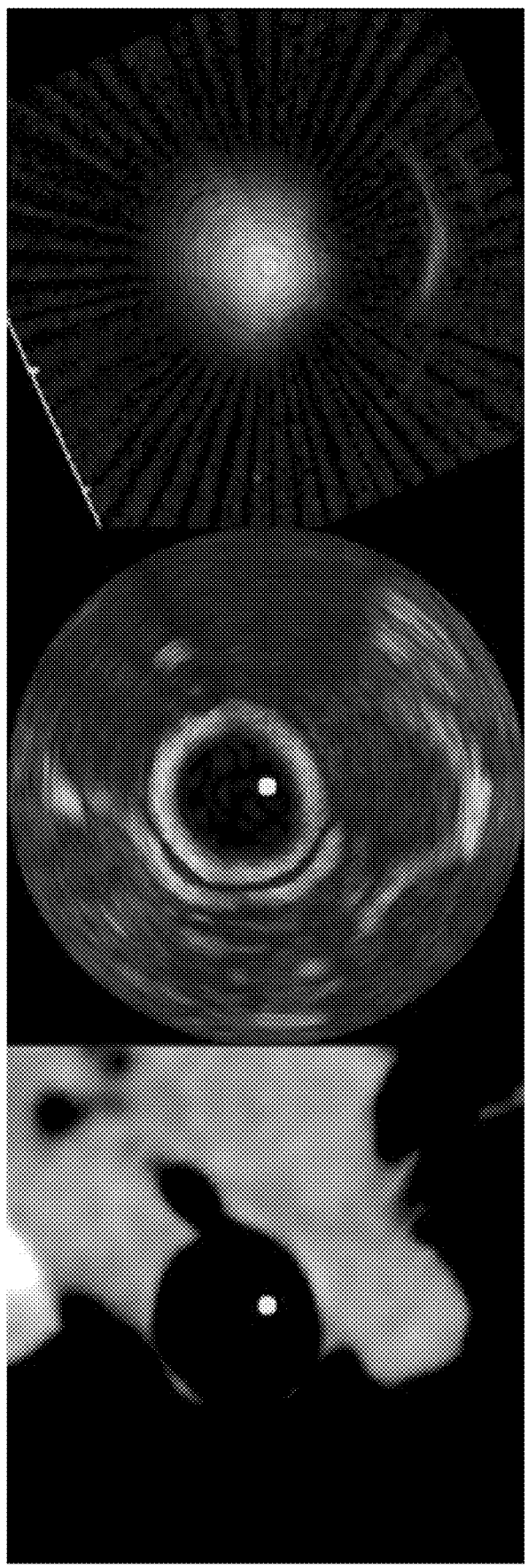
FIG. 34E shows a CT cross-section view at the registered RP-EBUS probe pose, CT-based RP-EBUS video simulation, and real RP-EBUS video at a nearby location.
Figure 35A:
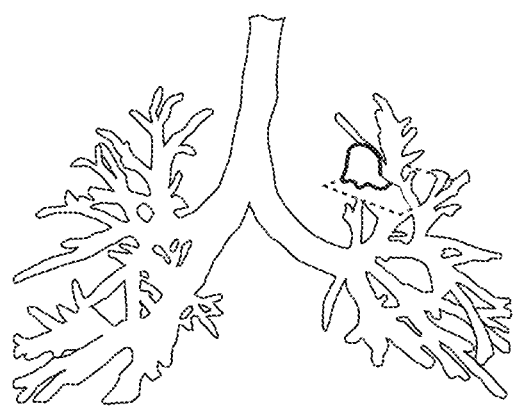
Figure 35B:
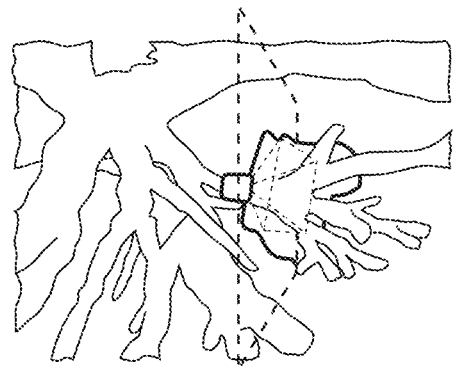
Figure 35C:
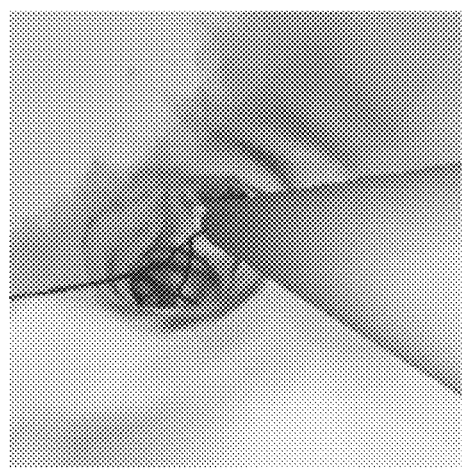
Figure 35D:

Next, FIGS. 32 and 33 illustrate guidance system results at initialization and final probe placement for phantom human case 20349.3.48 (the case used for Section 4 illustration). As another example, FIGS. 34A-34E give a result after guiding the physician toward an ROI in a live animal study. Both results show procedure success.

Finally, FIGS. 35A-35G give a human patient example for a left upper lobe lesion. Given the patient's chest CT scan, we first precompute a procedure plan, which gives an airway guidance route (blue line in 3D Airway Tree Rendering) leading to the lesion of interest [24, 67]. Next, during the live procedure, the guidance computer displays a series of graphical views used to guide the physician toward the preplanned lesion site. FIGS. 35A-35G show displayed views at the time the physician reaches the lesion site and performs RP-EBUS scanning. A two-phase registration process occurred prior to generating these views. First, the bronchoscope's position was synchronized to the guidance computer's virtual bronchoscope (VB) by registering the bronchoscope's "real" video view to the guidance system's VB view, shown in FIGS. 35C and 35D, as done by current image-guided bronchoscopy systems [39, 48]. Next, the virtual and real RP-EBUS probes, engaged in the working channels of the respective devices, underwent a second local registration operation to complete the synchronization of the real device to the preplanned location, shown in FIGS. 35E-35G. With this synchronization complete, the physician could now probe for and immediately locate the extraluminal lesion with confidence.

To recap, many endoscopic procedures draw on two separate complementary devices. For such a procedure, the endoscope navigates through a hollow organ system, such as the lung airways, toward a diagnostic site of interest (ROI) that is not visible in the hollow region. For the lungs, the primary example is a suspect lung cancer nodule. To effectively visualize and then manage this ROI (i.e., assess, biopsy, treat, monitor), the physician draws on a second device inserted into the endoscope's working channel. The second device provides the necessary visual confirmation of localizing the ROI in the complex organ system.

Unfortunately, physicians have considerable difficulty in coordinating the use of the two devices: 1. When should the physician use the second device? 2. Where should the physician scan the anatomy with this device?

This situation is analogous to the problem of trying to find a concealed object in one of the walls, floor, or ceiling, of a room in a large house. While the person might navigate through the house to the proper room correctly, the person then confronts the problem of not knowing which wall and where in the wall the concealed object (the ROI) is situated.

For the problem of lung cancer diagnosis and peripheral nodules, the physician uses a bronchoscope and an endobronchial ultrasound (EBUS) probe. For this problem, a methodology is provided in the present invention that solves this two-device problem, independent of physician skill (other than knowing how to use and interpret the devices). The second device may be any device inserted into the endoscope's working channel such as an EBUS.

More over, the present methodology could help drive a robotics system for such two-device procedures involving ROIs external to the hollow organ system, thereby assisting the physician in performing precise difficult procedures. Regarding other applications, the methodology could see utility in repeat airway exams of the two lungs for disease monitoring and follow-up over exams done at different times (e.g., monitoring lung tumor development or treatment impact).

Returning to the lung cancer problem, EBUS is a fast, inexpensive, safe, noninvasive method for imaging extraluminal sites. Regardless of a physician's confidence in maneuvering an EBUS probe toward a site, the extreme complexity of the 3D airway geometry and the 360° scope of the walls about an airway make it very difficult to know their precise scan location in the lungs—this is especially true in the peripheral airways, where it is well-known that a physician gets lost very quickly. Along this line, even a robot, despite its immunity to stress and time constraints, etc., cannot not know positively that a proper site is reached without a live in vivo confirmation by a second device, such as EBUS.

Adding to these points, the broad world-wide roll-out of CT-based lung cancer screening will greatly increase the patient population that will exhibit small, hard-to-find peripheral nodules that must be monitored and, as needed, treated as soon as its deemed vital to the patient's long-term survival. Accurate, timely bronchoscopy with EBUS—performed by many physicians, not just a few expert physicians—will be essentially to treat the large patient population.

In addition, other secondary endoscopic devices, such as OCT, offer related safe, noninvasive means for imaging extraluminal structures. Finally, the present methodology could see utility in other organ systems and associated endoscopic devices. Examples are the stomach, abdomen, bladder, and vasculature (kidney, etc.), relying laparoscopy, cystoscopy, colonoscopy, or angioscopy. Many of these procedures also draw on ultrasound or related devices.

The present invention has been described with reference to some embodiments. However, it is realized that variants and equivalents to the preferred embodiments may be provided without departing from the scope of the invention as defined in the accompanying claims. It is to be understood that both the foregoing general description and the following detailed description of the present invention are exemplary and explanatory and are intended to provide further explanation of the invention as claimed. It is not intended to be exhaustive or to limit embodiments to the precise form disclosed. As such, this disclosure should be interpreted broadly.

REFERENCES

[1] Abhinav Agrawal, D Kyle Hogarth, and Septimiu Murgu. Robotic bronchoscopy for pulmonary lesions: a review of existing technologies and clinical data. *J. Thorac. Dis.*, 12 (6): 3279 June 2020.

[2] Max Allan, Steve Thompson, Matthew J Clarkson, Sébastien Ourselin, David J Hawkes, John Kelly, and Danail Stoyanov. 2d-3d pose tracking of rigid instruments in minimally invasive surgery. In *International Conference on Information Processing in Computer-assisted Interventions*, pages 1-10. Springer, June 2014.

[3] F. Asano. Practical application of virtual bronchoscopic navigation. In A. Mehta and P. Jain, editors, *Interventional Bronchoscopy*, volume 10 of *Respir. Med.*, pages 121-140. Humana Press, 2013.

[4] Amalina Binte Ebrahim Attia, Ghayathri Balasundaram, Malini Olivo, et al. A review of clinical photoacoustic imaging: Current and future trends. *Photoacoustics*, 16:100144, 2019.

[5] S Bhushan, R R R Kortum, and S Anandasabapathy. Progress and challenges of global high-resolution endoscopy. *Int Arch Intern Med*, 4 (1): 1-14, 2020.

[6] Charles Bibby and Ian Reid. Robust real-time visual tracking using pixel-wise posteriors. In *Euro. Conf. Comput. Vision*, pages 831-844, October 2008.

[7] BlenderOnlineCommunity. Blender-a 3D modelling and rendering package, 2018.

[8] David Bouget, Max Allan, Danail Stoyanov, and Pierre Jannin. Vision-based and marker-less surgical tool detection and tracking: a review of the literature. *Medical image analysis*, 35:633-654, 2017.

[9] Alicia M Cano, Francisco Gayá, Pablo Lamata, Patricia Sánchez-González, and Enrique J Gómez. Laparoscopic tool tracking method for augmented reality surgical applications. In *International Symposium on Biomedical Simulation*, pages 191-196. Springer, 2008.

[10] Alicia M Cano, Pablo Lamata, Francisco Gayá, and Enrique J Gómez. New methods for video-based tracking of laparoscopic tools. In *International Symposium on Biomedical Simulation*, pages 142-149. Springer, Springer Berlin Heidelberg, 2006.

[11] Sharad Chandrika and Lonny Yarmus. Recent developments in advanced diagnostic bronchoscopy. *European Respiratory Review*, 29 (157): 1-11, September 2020.

[12] R. Cheirsilp, Bascom, T. W. Allen, and W. E. Higgins. Thoracic cavity definition for 3D PET/CT analysis and visualization. *Comp. Biol. Med.*, 62:222-238, July 2015.

[13] R. Cheirsilp and W. E. Higgins. Multimodal 3D PET/CT system for bronchoscopic procedure planning. In C. L. Novak and S. Aylward, editors, *SPIE Medical Imaging 2013: Computer-Aided Diagnosis*, volume 8670, pages 86702X-1-86702X-14, February 2013.

[14] Liang-Chieh Chen, Yukun Zhu, George Papandreou, Florian Schroff, and Hartwig Adam. Encoder-decoder with atrous separable convolution for semantic image segmentation. In *Euro. Conf. Comput. Vision*, pages 801-818, September 2018.

[15] Francois Chollet. Xception: Deep learning with depthwise separable convolutions. In *IEEE Comp. Vision and Pattern Recog.*, pages 1251-1258. IEEE, July 2017.

[16] Marius Cordts, Mohamed Omran, Sebastian Ramos, Timo Rehfeld, Markus Enzweiler, Rodrigo Benenson, Uwe Franke, Stefan Roth, and Bernt Schiele. The cityscapes dataset for semantic urban scene understanding. In *IEEE Comp. Vision and Pattern Recog.*, pages 3213-3223 June 2016.

[17] Duane Campbell Cornish. *Real-time Bronchoscopic Guidance System Based on Movement Measurements*. PhD thesis, School of Electrical Engineering and Computer Science, The Pennsylvania State University, State College, PA, USA, 2012.

[18] Gerard J Criner, Ralf Eberhardt, Sebastian Fernandez-Bussy, Momen M Wahidi, et al. Interventional bronchoscopy: State-of-the-art review. *Am. J. Respir. Crit. Care Med.*, (1): 29-50, July 2020.

[19] M. Davoudi, H. Colt, K. Osann, C. Lamb, and J Mullon. Endobronchial ultrasound skills and tasks assessment tool. *Am. J. Respir. Crit. Care Med.*, 186 (8): 773-779, July 2012.

[20] Armin Ernst and Felix J F Herth. *Endobronchial ultrasound: an atlas and practical guide*. Springer Science & Business Media, 2009.

[21] A. Ernst and F. J. F. Herth. *Endobronchial Ultrasound: An Atlas and Practical Guide*. Springer Verlag, New York, NY, USA, 2009.

[22] Mark Everingham, S M Ali Eslami, Luc Van Gool, Christopher K I Williams, John Winn, and Andrew Zisserman. The pascal visual object classes challenge: A retrospective. *Int. J. Comput. Vis.*, 111 (1): 98-136, June 2015.

[23] J Scott Ferguson and David A Sonetti. Surprised but not shaken: AQuIRE sheds new light on innovations in bronchoscopy. *Am. J. Respir. Crit. Care Med.*, 193 (1): 9-10, 1 Jan. 2016.

[24] J. D. Gibbs, M. W. Graham, R. Bascom, D. C. Cornish, R. Khare, and W. E. Higgins. Optimal procedure planning and guidance system for peripheral bronchoscopy. *IEEE Trans. Biomed. Engin.*, 61 (3): 638-657, March 2014.

[25] T. R. Gildea and J. Cicenia. Electromagnetic navigation bronchoscopy. In A. Mehta and P. Jain, editors, *Interventional Bronchoscopy*, volume 10 of *Respir. Med.*, pages 107-120. Humana Press, 2013.

[26] Michael K Gould, Jessica Donington, William R Lynch, et al. Evaluation of individuals with pulmonary nodules: When is it lung cancer? diagnosis and management of lung cancer, 3rd. ed. Chest, 143 (5_suppl): e93S-e120S, May 2013.

[27] M. W. Graham, J. D. Gibbs, and W. E. Higgins. Computer-based route-definition system for peripheral bronchoscopy. *J. Digital Imaging*, 25 (2): 307-317, April 2012.

[28] Felix J F Herth, Ralf Eberhardt, and Maren Schuhmann. Bronchoscopy in lung cancer: navigational modalities and their clinical use. *Exp. Rev. Respir. Med.*, 10 (8): 901-906, August 2016.

[29] Jonathan Hexner and Rami R. Hagege. 2D-3D pose estimation of heterogeneous objects using a region based approach. *Int. J. Comput. Vision*, 118 (1): 95-112, May 2016.

[30] R. Khare, R. Bascom, and W. E. Higgins. Hands-free system for bronchoscopy planning and guidance. *IEEE Trans. Biomed. Eng.*, 62 (12): 2794-2811 December 2015.

[31] Shawn Lankton and Allen Tannenbaum. Localizing region-based active contours. *IEEE Trans. Image Process.*, 17 (11): 2029-239 September 2008.

[32] Tsung-Yi Lin, Michael Maire, Serge Belongie, James Hays, Pietro Perona, Deva Ramanan, Piotr Dollár, and C. Lawrence Zitnick. Microsoft COCO: Common objects in context. In David Fleet, Tomas Pajdla, Bernt Schiele, and Tinne Tuytelaars, editors, *Euro. Conf. Comput. Vision*. Springer International Publishing, September 2014.

[33] Tasneem Lokhandwala, Marisa A Bittoni, Robert A Dann, et al. Costs of diagnostic assessment for lung cancer: a medicare claims analysis. *Clin. Lung Cancer*, 18 (1): e27-e34, January 2017.

[34] K. Lu and W. E. Higgins. Interactive segmentation based on the live wire for 3D CT chest image analysis. *Int. J. Computer Assisted Radiol. Surgery*, 2 (3-4): 151-167, December 2007.

[35] K. Lu and W. E. Higgins. Segmentation of the central-chest lymph nodes in 3D MDCT images. *Comp. Biol. Med.*, 41 (9): 780-789, 2011.

[36] K. Lu, P. Taeprasartsit, R. Bascom, R. P. M. Mahraj, and W. E. Higgins. Automatic definition of the central-chest lymph-node stations. *Int. J. Computer Assisted Radiol. Surgery*, 6 (4): 539-555, 2011.

[37] K. M. Lynch and F. C. Park. *Modern Robotics*. Cambridge University Press, Cambridge, United Kingdom, May 2017.

[38] Hanna C McGregor, Michael A Short, Annette McWilliams, Diana Ionescu, et al. Real-time endoscopic raman spectroscopy for in vivo early lung cancer detection. *J. Biophotonics*, 10 (1): 98-110, January 2017.

[39] S. A. Merritt, R. Khare, R. Bascom, and W. E. Higgins. Interactive CT-video registration for image-guided bronchoscopy. *IEEE Trans. Medical Imaging*, 32 (8): 1376-1396 August 2013.

[40] S. A. Merritt, J. D. Gibbs, K. C. Yu, V. Patel, L. Rai, D. C. Cornish, R. Bascom, and W. E. Higgins. Real-time image-guided bronchoscopy for peripheral lung lesions: A phantom study. *Chest*, 134 (5): 1017-126 November 2008.

[41] Roozbeh Mottaghi, Xianjie Chen, Xiaobai Liu, Nam-Gyu Cho, Seong-Whan Lee, Sanja Fidler, Raquel Urtasun, and Alan Yuille. The role of context for object detection and semantic segmentation in the wild. In *IEEE Comp. Vision and Pattern Recog.*, pages 891-898, June 2014.

[42] Therese Maria Henriette Naur, Philip Mørkeberg Nilsson, Pia Iben Pietersen, Paul Frost Clementsen, and Lars Konge. Simulation-based training in flexible bronchoscopy and endobronchial ultrasound-guided transbronchial needle aspiration (EBUS-TBNA): a systematic review. *Respiration*, 93 (5): 355-362, April 2017.

[43] OpenCV. The Open Source Computer Vision Library. 'opencv.org', 2020.

[44] Ignacio Oropesa, Patricia Sánchez-González, Magdalena K Chmarra, Pablo Lamata, Alvaro Fernández, Juan A Sánchez-Margallo, Frank Willem Jansen, Jenny Dankelman, Francisco M Sánchez-Margallo, and Enrique J Gómez. Eva: laparoscopic instrument tracking based on endoscopic video analysis for psychomotor skills assessment. *Surgical endoscopy*, 27 (3): 1029-139 October 2013.

[45] Stanley Osher and James A Sethian. Fronts propagating with curvature-dependent speed: algorithms based on hamilton-jacobi formulations. *Journal of Computational Physics*, 79 (1): 12-49, November 1988.

[46] David E Ost, Armin Ernst, Jennifer Toth, et al. Diagnostic yield and complications of bronchoscopy for peripheral lung lesions. results of the AQuIRE registry. *Am. J. Respir. Crit. Care Med.*, 193 (1): 68-77, 1 Jan. 2016.

[47] Victor A Prisacariu and Ian D Reid. Pwp3d: Real-time segmentation and tracking of 3d objects. *International Journal of Computer Vision*, 98 (3): 335-354, July 2012.

[49] P. J. Reynisson, H. O. Leira, T. N. Hernes, E. F. Hofstad, et al. Navigated bronchoscopy: a technical review. *J. Bronchology Interv. Pulmonol.*, 21 (3): 242-264, July 2014.

[49] M Patricia Rivera, Atul C Mehta, and Momen M Wahidi. Establishing the diagnosis of lung cancer: diagnosis and management of lung cancer: American College of Chest Physicians evidence-based clinical practice guidelines. *Chest*, 143 (5_suppl): e142S-e165S, May 2013.

[50] Olga Russakovsky, Jia Deng, Hao Su, Jonathan Krause, Sanjeev Satheesh, Sean Ma, Zhiheng Huang, Andrej Karpathy, Aditya Khosla, Michael Bernstein, et al. Imagenet large scale visual recognition challenge. *Int. J. Comput. Vis.*, 115 (3): 211-252, December 2015.

[51] Alejandro H Sardi and Shaheen Islam. Early lung cancer detection, mucosal, and alveolar imaging. *Curr. Opinion Pulm. Med.*, 22 (3): 271-280, May 2016.

[52] Simone Scarlata, Patrizio Palermo, Piero Candoli, Ariela Tofani, Tommasangelo Petitti, and Lorenzo Corbetta. EBUS-STAT subscore analysis to predict the efficacy and assess the validity of virtual reality simulation for EBUS-TBNA training among experienced bronchoscopists. J. *Bronchology Interv. Pulmonol.*, 24 (2): 110-116, April 2017.

[53] Wes Shepherd, H G Colt, and G Finlay. Image-guided bronchoscopy for biopsy of peripheral pulmonary lesions. *UpToDate*, September 2018.

[54] Rebecca L. Siegel, Kimberly D. Miller, and Ahmedin Jemal. Cancer statistics, 2020. *CA Cancer J. Clin.*, 70 (1): 7-30, January/February 2020.

[55] Gerard A Silvestri, Anil Vachani, Duncan Whitney, Michael Elashoff, et al. A bronchial genomic classifier for the diagnostic evaluation of lung cancer. *New Engl. J. Med.*, 373 (3): 243-251, 16 Jul. 2015.

[56] D. E. Spratt, A. J. Wu, V. Adeseye, et al. Recurrence patterns and second primary lung cancers after stereotactic body radiation therapy for early-stage nonâ€ "small-cell lung cancer: implications for surveillance. *Clin. Lung Cancer*, 17:177-183, May 2016.

[57] P. Taeprasartsit and W. E. Higgins. Robust method for extracting the pulmonary vascular trees from 3D MDCT images. *SPIE Medical Imaging* 2011: *Image Processing*, pages 796237-1-796237-17, 2011.

[58] Lynn T Tanoue, Nichole T Tanner, Michael K Gould, and Gerard A Silvestri. Lung cancer screening. *Am. J. Respir. Crit. Care Med.*, 191 (1): 19-33, 1 Jan. 2015.

[59] Henning Tjaden, Ulrich Schwanecke, Elmar SchÃ¶mer, and Daniel Cremers. A region-based gauss-newton approach to real-time monocular multiple object tracking. *IEEE Transactions on Pattern Analysis and Machine Intelligence*, 41 (8): 1797-1812 August 2019.

[60] Henning Tjaden. *Robust Monocular Pose Estimation of Rigid 3D Objects in Real-Time*. PhD thesis, Department 08—Physics, Mathematics und Computer Science, Johannes Gutenberg University Mainz, Germany, 2019.

[61] Robert A A van Boerdonk, Illaa Smesseim, Daniëlle A M Heideman, et al. Close surveillance with long-term follow-up of subjects with preinvasive endobronchial lesions. *Am. J. Respir. Crit. Care Med.*, 192 (12): 1483-1489, 15 Dec. 2015.

[62] Vitalii Vasyliev, Jennifer Toth, Rebecca Bascom, and William E Higgins. Autonomous planning and guidance for convex-probe endobronchial ultrasound bronchoscopy. In C. A. Linte and J. Siewerdsen, editors, *SPIE Medical Imaging* 2021: *Image-Guided Procedures*,

*Robotic Interventions, and Modeling*, volume 11598, pages 115980T-1-115980T-11, 2021.

[63] M. M. Wahidi, F. J. F. Herth, A. Chen, G. Cheng, and L. Yarmus. State of the art: Interventional pulmonology. *Chest*, 157 (3): 724-736, March 2020.

[64] Whittney A. Warren, Michal J. Sobieszczyk, Sy Sarkar, and William S. Krimsky. Endobronchial ultrasound bronchoscopy: current uses, innovations and future directions. *AME Med. J.*, 3 (1): 70, June 2018.

[65] Ann Chen Wu, James P. Kiley, Patricia J. Noel, et al. Current status and future opportunities in lung precision medicine research with a focus on biomarkers. *Am. J. Respir. Crit. Care Med.*, 198 (12): 1479-1489, 15 Dec. 2018.

[66] K. C. Yu, J. D. Gibbs, M. W. Graham, and W. E. Higgins. Image-based reporting for bronchoscopy. *J. Digital Imaging*, 23 (1): 39-50, February 2010.

[67] X. Zang, J. D. Gibbs, R. Cheirsilp, P. D. Byrnes, J. Toth, R. Bascom, and W. E. Higgins. Optimal route planning for image-guided EBUS bronchoscopy. *Comput. Biol. Med.*, 112 (7): 103361, September 2019.

[68] X. Zang. *EBUS/MDCT Fusion for Image-Guided Bronchoscopy*. PhD thesis, The Pennsylvania State University, Department of Computer Science and Engineering, 2016.

[69] Wennan Zhao. *Planning and Guidance Methods for Peripheral Bronchoscopy*. PhD thesis, The Pennsylvania State University, Department of Electrical Engineering, 2022.

The invention claimed is:

1. A two-phase method for guiding a live surgical procedure taking place in a hollow organ system that requires an endoscope and a second device used in tandem, where the second device is deployed through a working channel of the endoscope, the method comprising the steps of:

receiving a 3D pre-operative imaging scan;

precomputing a procedure plan based on the 3D pre-operative imaging scan, the procedure plan including a region of interest (ROI) located outside the hollow organ system and a guidance route traversing the hollow organ system and terminating at a target pose near the ROI; and performing a guidance protocol comprising the steps of:
a. providing simulated virtual video views inside the hollow organ system along the guidance route from a virtual endoscope defined within a 3D virtual space constructed based on the 3D pre-operative imaging scan;
b. displaying a plurality of live real video views of the hollow organ system from the endoscope, as an endoscope operator maneuvers the endoscope through the hollow organ system;
c. presenting a simulated virtual video view at an initial reference pose along the precomputed guidance route, which instructs the endoscope operator to move the endoscope close to the initial reference pose;
d. invoking a navigation method that presents a simulated virtual video view corresponding to a new reference pose further along the precomputed guidance route, which instructs the endoscope operator to move the endoscope close to the new reference pose;
e. repeating step d) a plurality of times until the navigation method presents a simulated virtual video view at a reference pose corresponding to the target pose near the ROI, with the simulated virtual video at the reference pose view depicting a virtual second device protruding into the hollow organ system, the virtual video view depicting the virtual second device representing the insertion of the virtual second device into the virtual endoscope's working channel; and instructing the endoscope operator to move the endoscope close to the target pose and then to insert the second device into the working channel of the endoscope until the second device appears in the live real video views;
f. receiving a frozen real video view of the endoscope, the frozen real video view depicting the second device protruding into the hollow organ system;
g. performing the guidance protocol including the steps of:
  i. performing a 3D alignment of the virtual endoscope and the endoscope by automatically registering the virtual video views of the virtual endoscope to the frozen real video view of the endoscope to give 3D transformation $T_e$;
  ii. using the 3D transformation $T_e$ as an initialization, performing a 3D alignment of the virtual second device to the second device by:
    i. registering a 3D model of the virtual second device to the 2D shape of the second device depicted in the frozen real video view to give 3D transformation $T_{de}$;
    ii. combining the two transformations to give final 3D alignment transformation $T_d = T_{de} \cdot T_e$ to align the virtual second device to the second device,
  whereby poses of the virtual endoscope and the virtual second device are synchronized to the endoscope and the second device.

2. The method according to claim 1, wherein the procedure plan includes suggested device instructions indicating:

how to maneuver the endoscope along the guidance route;

when to switch from maneuvering the endoscope to the second device; and/or when the target pose near the ROI is reached so that the second device can be inserted into the endoscope's working channel.

3. The method according to claim 1, wherein the hollow organ system is selected from the group consisting of lung airways, vasculature in a heart, brain, liver, kidney or hollow areas in a colon, stomach, bladder, and pelvis/abdomen.

4. The method according to claim 1, wherein the endoscope is a bronchoscope, colonoscope, laparascope, angioscope or cystoscope.

5. The method according to claim 1, wherein the ROI is a suspect tumor, suspect nodule, suspect early cancer lesion along an airway wall, optimal biopsy site, a site for anatomical, cytological, or histopathological examination, or a therapeutic site.

6. The method according to claim 1, wherein the second device is an EBUS probe, optical coherence tomography probe, confocal laser endomicroscope, radiofrequency ablation device, microwave ablation device, photodynamic therapy device, brachytherapy device, cryoablation device, vapor thermal ablation device, or a needle for direct therapeutic injection.

7. The method according to claim 1, wherein the ROI is examined by performing a visual assessment of the ROI, delivering treatment to the ROI, or collecting anatomical tissue for the ROI by the endoscope operator.

8. The method according to claim 1, wherein the step of registering a 3D model of the virtual second device to the 2D shape of the second device depicted in the frozen real video view to give 3D transformation $T_{de}$ comprises;

a. automatically segmenting the second device's shape in the endoscope's frozen real video view using a semantic segmentation method based on deep learning;
b. automatically registering the second device's shape to the 3D model of the virtual second device visible in the virtual views of the virtual endoscope using an optimization method drawing on level sets.

9. The method according to claim 1, wherein the endoscope operator is a physician or a robot.

10. A system for pre-operative planning and live guidance of a surgical procedure to examine a region of interest (ROI) situated outside a hollow organ system, comprising:

an endoscope operated to navigate through a hollow organ system and a second device that is deployed through a working channel of the endoscope and used in tandem with the endoscope;

a display device operative to display live, real endoscopic video images obtained by the endoscope, simulated images from a virtual space and cues and instructions for guidance of the endoscope and the second device;

a memory for storing a precomputed procedure plan;

a processor in communication with the memory and operable to execute the following:

receive a 3D pre-operative imaging scan;

precompute a procedure plan based on the 3D pre-operative imaging scan, the procedure plan including a region of interest (ROI) located outside the hollow organ system and a guidance route traversing the hollow organ system and terminating at a target pose near the ROI; and perform a guidance protocol comprising the steps of:
a. provide simulated virtual video views inside the hollow organ system along the guidance route from a virtual endoscope defined within a 3D virtual space constructed based on the 3D pre-operative imaging scan;
b. display a plurality of live real video views of the hollow organ system from the endoscope, as an endoscope operator maneuvers an endoscope through the hollow organ system;
c. present a simulated virtual video view at an initial reference pose along the precomputed guidance route, which instructs the endoscope operator to move the endoscope close to the initial reference pose;
d. invoke a navigation method that presents a simulated virtual video view corresponding to a new reference pose further along the precomputed guidance route, which instructs the endoscope operator to move the endoscope close to the new reference pose;
e. repeat step d) a plurality of times until the navigation method presents a simulated virtual video view at a reference pose corresponding to the target pose near the ROI, with this simulated virtual video at the reference pose view depicting a virtual second device protruding into the hollow organ system, the virtual video view depicting the virtual second device representing the insertion of the virtual second device into the virtual endoscope's working channel; and instruct the endoscope operator to move the endoscope close to the target pose and then to insert the second device into the working channel of the endoscope until the second device appears in the live real video views;
f. receive a frozen real video view of the endoscope, the frozen real video view depicting the second device protruding into the hollow organ system;
g. perform the guidance protocol including the steps of:
 i. perform a 3D alignment of the virtual endoscope and the endoscope by automatically registering the virtual video views of the virtual endoscope to the frozen real video view of the endoscope to give 3D transformation $T_e$;
 ii. use the 3D transformation $T_e$ as an initialization, performing a 3D alignment of the virtual second device to the second device by:
  1. register a 3D model of the virtual second device to the 2D shape of the second device depicted in the frozen real video view to give 3D transformation $T_{de}$;
  2. Combine the two transformations to give final 3D alignment transformation $T_d = T_{de} \cdot T_e$ to align the virtual second device to the second device, whereby poses of the virtual endoscope and the virtual second device are synchronized to the endoscope and the second device.

* * * * *